United States Patent
O'Dwyer

(10) Patent No.: US 10,906,951 B2
(45) Date of Patent: Feb. 2, 2021

(54) MODIFIED NATURAL KILLER CELLS AND NATURAL KILLER CELL LINES HAVING INCREASED CYTOTOXICITY

(71) Applicant: ONK THERAPEUTICS LIMITED, Galway (IE)

(72) Inventor: Michael Eamon Peter O'Dwyer, Galway (IE)

(73) Assignee: ONK THERAPEUTICS LIMITED, Galway (IE)

(*) Notice: Subject to any disclaimer, the term of this patent is extended or adjusted under 35 U.S.C. 154(b) by 130 days.

(21) Appl. No.: 15/885,301

(22) Filed: Jan. 31, 2018

(65) Prior Publication Data

US 2018/0201661 A1 Jul. 19, 2018

Related U.S. Application Data

(63) Continuation-in-part of application No. 15/405,163, filed on Jan. 12, 2017, now Pat. No. 10,034,925, which is a continuation of application No. PCT/EP2016/068001, filed on Jul. 28, 2016.

(30) Foreign Application Priority Data

| Jul. 29, 2015 | (EP) | 15178899 |
| Mar. 2, 2016 | (GB) | 1603655.0 |
| Mar. 31, 2016 | (GB) | 1605457.9 |
| Jun. 10, 2016 | (GB) | 1610164.4 |

(51) Int. Cl.
| C07K 14/52 | (2006.01) |
| A61K 35/17 | (2015.01) |
| A61K 38/19 | (2006.01) |
| C12N 5/0783 | (2010.01) |
| A61P 35/02 | (2006.01) |
| A61K 31/69 | (2006.01) |
| A61K 39/00 | (2006.01) |
| A61P 35/00 | (2006.01) |

(52) U.S. Cl.
CPC ............ *C07K 14/52* (2013.01); *A61K 31/69* (2013.01); *A61K 35/17* (2013.01); *A61K 38/19* (2013.01); *A61K 39/0011* (2013.01); *A61P 35/00* (2018.01); *A61P 35/02* (2018.01); *C12N 5/0646* (2013.01); *A61K 2039/5156* (2013.01); *A61K 2039/5158* (2013.01); *A61K 2039/572* (2013.01); *A61K 2039/804* (2018.08); *C12N 2510/00* (2013.01)

(58) Field of Classification Search
CPC ..................................................... C07K 14/52
See application file for complete search history.

(56) References Cited

U.S. PATENT DOCUMENTS

| 2003/0219419 A1 | 11/2003 | Shirwan |
| 2006/0165665 A1 | 7/2006 | Min et al. |
| 2011/0262455 A1* | 10/2011 | Samali ............ A61K 31/7105 424/158.1 |
| 2013/0129771 A1 | 5/2013 | Yarkoni et al. |
| 2015/0361396 A1 | 12/2015 | Regev et al. |
| 2018/0171298 A1* | 6/2018 | Duchateau .......... C12N 5/0646 |

FOREIGN PATENT DOCUMENTS

| EP | 1621550 A1 | 2/2006 |
| WO | WO 2006023148 A2 | 3/2006 |
| WO | WO 2006023148 A3 | 8/2006 |
| WO | WO 2009077857 A2 | 6/2009 |
| WO | WO 2015012145 A1 | 1/2015 |
| WO | WO 2015157252 A1 | 10/2015 |
| WO | WO 2015161276 A2 | 10/2015 |
| WO | WO 2016160721 A1 | 10/2016 |
| WO | WO 2017017184 A1 | 2/2017 |

OTHER PUBLICATIONS

Zamai et al. (J. Exp. Med. Dec. 21, 1998; 188(2): 2375-2380) (Year: 1998).*
Lundqvist et al. (J Cancer. 2011; 2: 383-385.) (Year: 2011).*
Szegezdi, E., et al., "Targeting AML through DR4 with a novel variant of rhTRAIL," *J. Cell. Mol. Med.* 15(10):2216-2231, Foundation for Cellular and Molecular Medicine/Blackwell Publishing, United States (2011).
Bodduluru et al., "Natural killer cells: the journey from puzzles in biology to treatment of cancer," Cancer Lett. 357(2):454-467 (2015).
Carlsten et al., "Genetic Manipulation of NK Cells for Cancer Immunotherapy: Techniques and Clinical Implications," Front Immunol 6:266 (2015).
Chan et al., "The receptors CD96 and CD226 oppose each other in the regulation of natural killer cell functions," Nat Immunol 15(5):431-438 (2014).
Duiker et al., "Enhanced Antitumor Efficacy of a DR5-Specific TRAIL Variant Over Recombinant Human TRAIL in a Bioluminescent Ovarian Cancer Xenograft Model," Clin Cancer Res 15(6):2048-2057 (2009).
Fehniger et al., "Acquisition of Murine NK Cell Cytotoxicity Requires the Translation of a Preexisting Pool of Granzyme B and Perforin mRNAs," Immunity 26(6):798-811 (2007).
Ferrara et al., "Acute myeloid leukaemia in adults," Lancet 381:485-495 (2013).
Fuchs et al., "Cutting edge: CD96 (tactile) promotes NK cell-target cell adhesion by interacting with the poliovirus receptor (CD155)," J Immunol 172(7):3994-3998 (2004).
Gallois et al., "Reversal of natural killer cell exhaustion by TIM-3 blockade," OncoImmunology 3:12, e946365 (2014).

(Continued)

*Primary Examiner* — Scott Long
(74) *Attorney, Agent, or Firm* — Sterne, Kessler, Goldstein & Fox P.L.L.C.

(57) ABSTRACT

NK cells and NK cell lines are modified to increase cytotoxicity, wherein the cells and compositions thereof have a use in the treatment of cancer. Production of modified NK cells and NK cell lines is via genetic modification to add mutant (variant) TRAIL ligand expression.

9 Claims, 20 Drawing Sheets

Specification includes a Sequence Listing.

(56) References Cited

OTHER PUBLICATIONS

Ghiringhelli et al., "Metronomic cyclophosphamide regimen selectively depletes CD4+CD25+ regulatory T cells and restores T and NK effector functions in end stage cancer patients," Cancer Immunol. Immunothe 56:641-648 (2007).
Gong et al., "Characterization of a human cell line (NK-92) with phenotypical and functional characteristics of activated natural killer cells," Leukemia 8(4):652-658 (1994).
Heidenreich et al., "Impact of the NK Cell Receptor LIR-1 (ILT-2/CD85j/LILRB1) on Cytotoxicity against Multiple Myeloma," Clin Dev Immunol 2012:652130 (2012).
Hodge et al., "Enhanced cytotoxic function of natural killer and natural killer T-like cells associated with decreased CD94 (Kp43) in the chronic obstructive pulmonary disease airway," Respirology 18(2):369-376 (2013).
Hurwitz et al., "Treatment of patients with acute myelogenous leukemia: review of clinical trials of the past decade," J Pediatr Hematol Oncol 17(3):185-197 (1995).
Jandus et al., "Interactions between Siglec-7/9 receptors and ligands influence NK cell-dependent tumor immunosurveillance," J Clin Invest 124(4):1810-1820 (2014).
Klingemann, "Are natural killer cells superior CAR drivers?" OncoImmunology 3:4:e28147 (2014).
Kobayashi et al., "A chimeric antigen receptor for TRAIL-receptor 1 induces apoptosis in various types of tumor cells," Biochem Biophys Res Commun 453(4):798-803 (2014).
Koh et al., "Augmentation of antitumor effects by NK cell inhibitory receptor blockade in vitro and in vivo," Blood 97(10):3132-3137 (2001).
Leong et al., "Human NK cells: SET to kill," Blood 117:2297-2298 (2011).
Lin et al., "TM4SF1: a new vascular therapeutic target in cancer," Angiogenesis 17(4):897-907 (2014).
Lowenberg et al., "Acute myeloid leukemia," N Engl J Med 341(14):1051-1062 (1999).
Lundqvist et al., "Bortezomib Treatment to Potentiate the Antitumor Immunity of Ex-vivo Expanded Adoptively Infused Autologous Natural Killer Cells," J Cancer 2:383-385 (2011).
Miller et al., "Successful adoptive transfer and in vivo expansion of human haploidentical NK cells in patients with cancer," Blood 105:3051-3057 (2005).
Minton et al., "Natural killer cells: a TACTILE restraint," Nat Rev Immunol 14(5):285 (2014).
Mirandola, P. et al., "Activated human NK and CD8$^+$T cells express both TNF-related apoptosis-inducing ligand (TRAIL) and TRAIL receptors but are resistant to TRAIL-mediated cytotoxicity," Blood 104:2418-2424 (Oct. 2004).
Moretta et al., "Unravelling natural killer cell function: triggering and inhibitory human NK Receptors," EMBO J 23:255-259 (2004).
Morvan et al., "NK cells and cancer: you can teach innate cells new tricks," Nat Rev Cancer 16(1):7-19 (2016).
Neeson et al., "Induction of potent NK cell-dependent anti-myeloma cytotoxic T cells in response to combined mapatumumab and bortezomib," Oncoimmunology 4(9):e1038011 (2015).
Nicoll et al., "Ganglioside GD3 expression on target cells can modulate NK cell cytotoxicity via siglec-7-dependent and -independent mechanisms," Eur J Immunol 33(6):1642-1648 (2003).
Nicoll et al., "Identification and characterization of a novel siglec, siglec-7, expressed by human natural killer cells and monocytes," J Biol Chem 274(48):34089-34095 (1999).
Onishi et al., "Forced Fucosylation With ASC-1 01 Enhances the Binding of Ex Vivo Expanded Human NK Cells to E-Selectin: A Novel Method to Improve the Homing of Adoptively Transferred NK Cells to the Bone Marrow in Patients With Hematological Malignancies," Adoptive Immunotherapy: Poster III. Abstract 4499 (2 pgs) (2013).
PCT/EP2016/068001 International Search Report and Written Opinion dated Oct. 18, 2016.
Pegram et al., "Adoptive Transfer of Gene-Modified Primary NK Cells Can Specifically Inhibit Tumor Progression In Vivo," J. Immunol 181:3449-3455 (2008).
Ribeiro et al., "Successive clinical trials for childhood acute myeloid leukemia at St Jude Children's Research Hospital, from 1980 to 2000," Leukemia 19:2125-2129 (2005).
Rubnitz et al., "Treatment outcome in older patients with childhood acute myeloid leukemia," Cancer 118(24):6253-6259 (2012).
Ruggeri et al., "Effectiveness of donor natural killer cell alloreactivity in mismatched hematopoietic transplants," Science 295(5562):2097-2100 (2002).
Ruggeri et al., "Effects of anti-NKG2A antibody administration on leukemia and normal hematopoietic cells," Haematologica 101(5):626-633 (2016).
Ruggeri et al., "Exploitation of alloreactive NK cells in adoptive immunotherapy of cancer," Curr Opin Immunol 17(2):211-217 (2005).
Savani et al., "Rapid natural killer cell recovery determines outcome after T-cell-depleted HLA-identical stem cell transplantation in patients with myeloid leukemias but not with acute lymphoblastic leukemia," Leukemia 21:2145-2152 (2007).
Seymour et al., "Phase 1 studies: Miscellaneous drugs & targets," Annals of Oncology 26(Supplement 2):ii3-ii5 (2015) (Abstract).
Shook et al., "Natural killer cell engineering for cellular therapy of cancer," Tissue Antigens 78(6):409-415 (2011).
Smyth et al., "Tumor necrosis factor-related apoptosis-inducing ligand (TRAIL) contributes to interferon gamma-dependent natural killer cell protection from tumor metastasis," J Exp Med 193(6):661-670 (2001).
Suck et al., "Irradiated KHYG-1 retains cytotoxicity: potential for adoptive immunotherapy with a natural killer cell line," Int J Radiat Biol 82(5):355-361 (2006).
Suck et al., "KHYG-1, a model for the study of enhanced natural killer cell cytotoxicity," Exp Hematol 33:1160-1171 (2005).
Swift et al., "Natural killer cell lines preferentially kill clonogenic multiple myeloma cells and decrease myeloma engraftment in a bioluminescent xenograft mouse model," Haematologica 97(7):1020-1028 (2012).
Swift, "Natural Killer Cell Line Therapy in Multiple Myeloma," Institute of Biomaterials and Biomedical Engineering, University of Toronto. Thesis (135 pgs) (2011).
Szegezdi et al., "Targeting AML through DR4 with a novel variant of rhTRAIL," J Cell Mol Med 15(10):2216-2231 (2011).
Tang et al., "Potential for enhanced therapeutic activity of biological cancer therapies with Doxycycline combination," Gene Therapy 20(7):770-778 (2013).
Trowsdale et al., "The genomic context of natural killer receptor extended gene families," Immunol Rev 181:20-38 (2001).
Truneh et al., "Temperature-sensitive differential affinity of TRAIL for its receptors. DR5 is the highest affinity receptor," J Biol Chem 275(30):23319-23325 (2000).
Van Der Sloot et al., "Designed tumor necrosis factor-related apoptosis-inducing ligand variants initiating apoptosis exclusively via the DR5 receptor," PNAS USA 103(23):8634-8639 (2006).
Van Dijk et al., "The Proteasome Inhibitor Bortezomib Sensitizes AML with Myelomonocytic Differentiation to TRAIL Mediated Apoptosis," Cancers (Basel) 3(1):1329-135SO (2011).
Wang et al., "Identification and molecular cloning of tactile. A novel human T cell activation antigen that is a member of the Ig gene superfamily," 148(8):2600-2608 (1992).
Yan et al., "Antileukemia activity of a natural killer cell line against human leukemias," Clin Cancer Res 4(11):2859-2868 (1998).
Zhang et al., "Characterization of interleukin-15 gene-modified human natural killer cells: implications for adoptive cellular immunotherapy," Haematologica 89(3):338-347 (2004).
Reis, C.R. et al. "Rapid and efficient cancer cell killing mediated by high-affinity death receptor homotrimerizing TRAIL variants," *Cell Death and Disease*, 1:e83 (2010).
Nakamura, K., et al., "NK-cell fratricide: Dynamic crosstalk between NK and cancer cells," *OncoImmunology* 2(11):e26529, Landes Bioscience, United States (2013).
Neumann, S., et al., "The transmembrane domains of TNF-related apoptosis-inducing ligand (TRAIL) receptors 1 and 2 co-regulate

(56) References Cited

OTHER PUBLICATIONS apoptotic signaling capacity," *PLoS One* 7(8):e42526, Public Library of Science, United States (2012).

Tam, Y.K., et al., "Ex vivo expansion of the highly cytotoxic human natural killer-92 cell-line under current good manufacturing practice conditions for clinical adoptive cellular immunotherapy," *Cytotherapy* 5(3):259-272, Elsevier Inc., United States (2003).

Tonn, T., et al., "Cellular immunotherapy of malignancies using the clonal natural killer cell line NK-92," *Journal of Hematotherapy & Stem Cell Research* 10(4):535-544, Mary Ann Liebert Inc., United States (2001).

Rosenstock, P., et al., "Siglec-7 expression is reduced on a natural killer (NK) cell subset of obese humans," *Immunol Res* 65:1017-1024, Humana Press, United States (2017).

Wang, Y., et al., "Fratricide of NK Cells in Daratumumab Therapy for Multiple Myeloma Overcome by Ex Vivo Expanded Autologous NK Cells," *Clin Cancer Res* 24(16):4006-4017, American Association for Cancer Research Inc., United States (2018).

\* cited by examiner

```
                        SEQUENCE LISTING

<160> NUMBER OF SEQ ID NOS: 14

<210> SEQ ID NO 1
<211> LENGTH: 9540
<212> TYPE: DNA
<213> ORGANISM: Homo sapiens

<400> SEQUENCE: 1
ctctggcctc tgttctttct tgtgagtccg tctacacttg gggtttccac atgtcttttt      60
ctgctcatga ccttgatact ctgggtattt cagaaatgct acacatacgt ttctccatta     120
cggtcagatg tgacatcttg agtggactca tcaatcacct acagaatgtg gagtccaaca     180
gcaagatcct ctcacgtccc aaagcctcag gtcttaccct ggtctggaaa tcaagcacaa     240
atgagcccct cccaatgtcc caggcaccac tgaccccaca accactgtga cgagtgggat     300
tcatgacaac aatctgcaaa ggaagaaact gaggctcagt gatgggacat acaaaccaa      360 ggtcacgtag gcagcggatg ataaccagtc atcaaataaa tatcaactcc ctcccccact     420
ccccaaatca aagctcaaac ataagtcatt gttcccaaaa tgttgaccag gaattgaggt     480
gcagagggac ggctaaggac gcaatgggca ccgaggaggc aggaaagact cagaggtttc     540
ttcccggggg ggagggagtg gacgctggag caaaaacatt taaaaagggg aagttaagag     600
gggactattt ggttgaaaga aaacccacaa tccagtgtca agaaagaagt caacttttct     660 tccctactt ccctgcattt ctcctctgtg ctcactgcca cacacagctc aacctggaca     720
gcacagccag aggcgagatg cttctctgct gatctgagtc tgcctgcagc atggacctgg     780
gtcttccctg aagcatctcc agggctggag ggacgactgc catggtaagg accccacaac     840
gctgtgctga tggatgggct gaaggaggga gggtgaccat gtgggaagct gtgagaagga     900 agggaagcc actgctaccc tcatcaggaa gggcagacac aagaagcacc agttctattt     960
gctgctacat cccggctctc ggtgagacga ggagaaacca gacagacagt ggctggggt      1020 caggaaagac cccattacag tctgaaatgt ctgcagaggg cccagtgcct gcccccacct    1080
cagctctaaa agaatgagag tcaggctcct gggagggcag ttccgcttct tgtgtggctg    1140
cagatgacaa caccccatga gaaggaccca gcctctgagt gtccacacag ggtgggaagg    1200 agggaggct atttctctct gtgtgtctct gtcccgccag caccgagggc tcatccatcc     1260
gcagagcagg gcagtgggag gagacgccat gaccccatc gtcacagtcc tgatctgtct    1320
cggtgagatt tgaagagaga ggggagcttc taacctagga gggacctcac cccacagcca     1380
aactctggtc cctaaggaga ccccaggggc tcacaaagat cccagggagg ggaggacctg    1440
ctcaggcttc aggggcaaa tccctcacag ggaactctct tccagggctg agtctgggcc      1500
ccaggacccg cgtgcagaca ggtgagtctg tccccagctc tcccaggtcc ctcctcctca    1560
```

```
ctggggacaa ggggccacct ccgtgcagct ggggatgggg attagaagtt ctggactgac    1620 tgatggggc atctggaggg tcctgggctg agagctgaga tctgttgggt gggaaatgac     1680
ttcgaatctg acctttgatt tccttccagg gaccatcccc aagcccaccc tgtgggctga    1740
gccagactct gtgatcaccc aggggagtcc cgtcaccctc agttgtcagg ggagccttga    1800
agcccaggag taccgtctat atagggagaa aaaatcagca tcttggatta cacggatacg    1860
accagagctt gtgaagaacg ccagttcca catcccatcc atcacctggg aacacacagg     1920
gcgatatggc tgtcagtatt acagccgcgc tcggtggtct gagctcagtg accccctggt    1980
gctggtgatg acaggtgaga ggacactcag ggatcccagc cccaggctct gccctcagga    2040
aggaggctct caggggtgtc tccctctcac agcccagccc tggggatgat gtgggaggtg    2100
ggagccccat ttaacacgat gcctccttct ctcctaggag cctacccaaa acccaccctc    2160
tcagcccagc ccagccctgt ggtgacctca ggaggaaggg tgaccctcca gtgtgagtca    2220
caggtggcat ttggcggctt cattctgtgt aaggaaggag aagatgaaca cccacaatgc    2280
ctgaactccc agccccatgc ccgtgggtcg tcccgcgcca tcttctccgt gggccccgtg    2340
agcccgaatc gcaggtggtc gcacaggtgc tatggttatg acttgaactc tccctatgtg    2400
tggtcttcac ccagtgatct cctggagctc ctggtcccag gtgagaaatt cacagcattg    2460
tctggagttc cctgagtctc cctgagtctc caggcaggtg gggagcagcc gtgtctcagg    2520
gcagttccag gtgggatgat gttggggcga gagggctcag gggtcctggg gccagagaca    2580
caggaagatc agcagtggtg aggcaccggg ggagagggag ggtttgtggg gaagcctgag    2640
ggtcggctcc tggaaaccat gagcaccttt tcccaggtgt ttctaagaag ccatcactct    2700
cagtgcagcc gggtcctgtc atggcccctg gggaaagcct gaccctccag tgtgtctctg    2760
atgtcggcta tgacagattt gttctgtaca aggaggggga acgtgacctt cgccagctcc    2820
ctggccggca gccccaggct gggctctccc aggccaactt caccctgggc cctgtgagcc    2880
gctcctacgg gggccagtac agatgctacg gtgcacacaa cctctcctct gagtgctcgg    2940
cccccagcga ccccctggac atcctgatca caggtgagga gcccagcggg ttcagtcagg    3000
gacccagact ctgcacaggc cctgccgggg gaatccaatt agtgatgcc aggatgaggc     3060 gggggtggt cccaagggag ggagagacag agagagagac aggggatggg tggggagggg     3120
aagactcaga gaaacagag acagaggctc tagagaggc ctggggaggt ctcagctcag      3180
agcaaggtgg ggcagcccct cacccatcct tcttctctcc aggacagatc cgtggcacac    3240
ccttcatctc agtgcagcca ggccccacag tggcctcagg agagaacgtg accctgctgt    3300
gtcagtcatg gcggcagttc cacactttcc ttctgaccaa ggcgggagca gctgatgccc    3360
cactccgtct aagatcaata cacgaatatc ctaagtacca ggctgaattc cccatgagtc    3420
ctgtgacctc agcccacgcg gggacctaca ggtgctacgg ctcactcaac tccgacccct    3480
acctgctgtc tcaccccagt gagccctgg agctcgtggt ctcaggtggg ggccttgacc     3540
ctgtcctctc tgagctcaaa ggctcagctc aggccctgcc ccccaggaga gctctgggct    3600
gggatggagt gagcgggggt ctgagcgggg ctcagccagt gggagactca ccctcagagg    3660
gaaggaggac aacaggccct cccaggcctg cgcacactca gcggcatcgc cagcatcatg    3720
gacaggagag gcgggtggag ggaggggcct ggggaggcca cagggcccat gtagagaaat    3780
ttggtttgag gtggagactt caggaaagcc ccagctcctc accctcctct cattctttca    3840
cccaggaccc tccatgggtt ccagcccccc acccaccggt cccatctcca cacctggtga    3900
gtccctgagg cctctggctc gaagggagcg cagcgacccc cagggcagct ttgagtgtcc    3960
```

```
aggaggatcc cattcccttc agggactcaa tcaagggctt ctgtccaggg agctgggcag   4020
agccagagga ggggccacag ggtccccagg gctctgaggc tgggctggtg aggggtgggg   4080
ggtcaaggca gagagaaatg ttggggccca gcctggggga ggagcagccg ggctgatgtg   4140
gggagcaggg cagccccagc cctcacctcc ccgtcctgac ccagcaggcc ctgaggacca   4200
gcccctcacc cccactgggt cggatcccca aagtggtgag tgagggctc tgagtgggag    4260 gtgggcgggt cccggggag gcaggggtgg gttctgtcct aggttcaggc tcctctggag    4320
gtggtgatgt agacaggctc ctcccctgcc tgggcctcag tttctccaag tgtaaggag    4380 agaggcctgc aggtgggaaa gttcctttca gctctcactc ccagctgtga cctcctggga   4440
gaggaggccc ctcagggaag actccaagac tcgattccgc gggggcctgt cccgtcccac   4500
ctgcagcaga gacggtgacc tggggcaggg gaggggagca gagtcgtggt tcaggacggt   4560
aaggctcttt ccctgcagct ccggggctcg gctctggtgc aggaacaagg gctgcaggtc   4620
agactcccag gctcccttcc cagctctgcc gcttcctggc tgggggcccg ggcaggcga    4680 ttcccctctc tgagcgtcag ttttcatct gtagagtggg tggggtggat gtttgtgtgc    4740
tgcacgactg ttgtgggggt tggaggtggt gaacagaagg tccagcagtc acctgcacac   4800
agtaggcgct catttcaatg acatcacccc catccctgac atcatcgtgc tcaaggtctg   4860
ggaaggcacc tgggggttgt gatcggcatc ttggtggccg tcgtcctact gctcctcctc   4920
ctcctcctcc tcttcctcat cctccgacat cgacgtcagg gcaaacactg gacatcgagt   4980
gagtagggaa ggggaaaccc tgtgggccga ccgagggtgg gctcagggca cagccaaaga   5040
gaatccaaac cactgggcaa atgcagcttt gagaaactgt tccagcattt ctcaccaggt   5100
gaatggagaa agcacttaac gtcagtccca tctacaaata taaagtgtcc tccgggctca   5160
gtcccatcta caaatgtaaa gtgtccttcg gactctgtcc atctcatgag gcatttggaa   5220
catggaggca ggagtgtttt taggtttcct tccttacctt cgagctgtgt gtgcagggca   5280
gggggctcca atgttcccag ggctgaggct ctgtccttct tcccccagcc cagagaaagg   5340
ctgatttcca acatcctgca ggggctgtgg ggcagagcc cacagacaga ggcctgcagt    5400
ggaggtaatt ctgcccgaag accccagact cccacctgct cgtggcccat acactgcccc   5460
taaagctccc attcctcccc caggtccagc ccagctgccg acgcccagga agaaaacctc   5520
tgtgagtgag aggaagaggt gaccagccag gaggagata ggggcccga agtttccgta    5580 gcaatgggga aaggggcacc ggctggaaag ggtctggggc tcagggtgag atcatctcac   5640
cccacactgt gggacctcag ggacattgca gcccctccct gcatctcagt agccccatct   5700
gggagcaggg caggggctgg caggactcag aggtcccagg gaaccttccc aagagacgaa   5760
ccccttgctc tgcccagca gatgctgccg tgaaggacac acagcctgaa gatgggtgg    5820 agatggacac tcgggtgaga ccccgccct gtcccaggca ccaaaggcct cctggtgcca    5880
gatctaatcc agcaggactt ctctgtcctc cttccccgg ctctcagcat cgtcacggtg    5940
gacccctcct tgtccagcac gctgcctccc gcctgctgtg acctcactct ctcctgctgt   6000
cctgggacct cgtgggcctc ctcccgggtc cccttcctgc tcctcatcct ctgtttggcc   6060
gtctggttgt tagagcgctc cccaggcctc tggaggatga ggaataaatg aaccacccccg  6120 gtccctgggg ctccccttca ttcattcaac cagtgagtgt tcccagggag ctcactgtgg   6180
atcaggctcc ccatgggagc tgcagacaca gcagggagca aagccgcccc cgcctcctga   6240
gctcacctca tggtgggaga caaaatgcaa ataaatgcgc catgtccagg agtgcaacgt   6300
```

```
gcttaaagga acatacacca gggaaagggc agagagtgtg gggcagtggg gccagtctga    6360
atggaagggg agggctgtct gctcagctgt catctgagaa gcctggacag agtggggcac    6420
acgatcctct aatggacgag cccctgcagg cagaggaaac agccgtgcaa aggccccgag    6480
gcagcagcga gctcttgcgg gaaggccat gaggctgcag ccaaatgggc aaggtcaaag     6540
tgaggagcag aggccagaac acaggaagg gagcggccag accctccacg gccttagggc     6600
gtccctgaga ttcatcggg aaagggatgt aatcggatca ccccgggaac agtgaggaaa     6660
attgactcca ggaggtcagg gggactcaag dacaccccc accactgtct ctctccagca     6720
gagcccacat gatgaagacc cccaggcagt gacatatgcc ccggtgaaac actccagacc    6780
taggagagaa atggcctctc ctccctcccc actgtccggg gaattcctgg acacaaagga    6840
cagacaggca gaagaggaca gacagatgga cactgagaga gtcctttcct ctccaggccc    6900
ccaggcctcc cccacccca ccacgttcct tacctctcac tctccccgc tgcaggctgc      6960
tgcatctgaa gcccccagg atgtgaccta cgcccagctg cacagcttga ccctcagacg    7020
gaaggcaact gagcctcctc catcccagga aagggaacct ccagctgagc ccagcatcta    7080
cgccaccctg gccatccact agcccggagg gtacgcagac tccacactca gtagaaggag    7140
actcaggact gctgaaggca cgggagctgc ccccagtgga caccaatgaa ccccagtcag    7200
cctggacccc taacaaagac catgaggaga tgctgggaac tttgggactc acttgattct    7260
gcagtcgaaa taactaatat ccctacattt tttaattaaa gcaacagact tctcaataat    7320
caatgagtta accgagaaaa ctaaaatcag aagtaagaat gtgctttaaa ctgaatcaca    7380
atataaatat tacacatcac acaatgaaat tgaaaaagta caaaccacaa atgaaaaaag    7440
tagaaacgaa aaaaaaaac taggaaatga atgacgttgg ctttcgtata aggaatttag     7500
aaaaagaata accaattatt ccaaatgaag gtgtaagaaa gggaataaga agaagaagag    7560
ttgctcatga ggaaaaacca aaacttgaaa attcaacaaa gccaatgaag ctcattcttg    7620
aaaatattaa ttacagtcat aaatcctaac tacattgagc aagagaaaga aagagcaggc    7680
acgcatttcc atatgggagt gagccagcag acagcccagc agatcctaca cacattttca    7740
caaactaacc ccagaacagg ctgcaaacct ataccaatat actagaaaat gcagattaaa    7800
tggatgaaat attcaaaact ggagtttaca taatgaacgt aagagtaatc agagaatctg    7860
actcatttta aatgtgtgtg tatgtgtgtg tatatatatg tgtgtgtgtg tgtgtgtgtg    7920
tgtgtgtgaa aaacattgac tgtaataaaa atgttcccat cgtatcaact ccagttcagg    7980
aagtttcact ggtgatttct tacaaatatt gacgcactaa tgaaacacac aaacacaccc    8040
agagcatcac aaatgtttct tgagaataga aaaagaggca atgtgcccgg gtgcggtggc    8100
tcacgcctgt aatctcaaca cctagggagg cagaggccac agattacttg aggccgggag    8160
ttcaagacca gcatggccaa caaggcaaaa ccccatctct actaaaaata caaaaattag    8220
ctggacatgg tggcgcacgc tgcaatccca gctacttggg aggcagaggc aggaggatca    8280
cttgaatgaa cccgggaggt ggaggttgaa gtgagcaaaa acaaccccc tacaattcag     8340
cctaggatat gtttattaaa tttacatttg tcttttgct taagattgct ttggtattca     8400
tcctcttttt ggttccatat gaattttagg atttttttct aattctgtga aaaaaatgat    8460
gttgatattt tgatgggaat tgcattgaac ctaaatattg ctttgggaag tgtgatcatt    8520
ttcacaatat tgattctgcc aatccatgag catgggatat attctatttt gctgtgtca    8580
tctacgattt ctttctgcag cattttgttg ttccttcttgt agagatcttt cacctcctca    8640
gttaggtata ttcttagata ttttttaattt tttgcaactg atgtacaagg gattgagttt    8700
```

```
tgcagcaacc tggatgagct ggaggccatt attcatgaca ccacatccag ctaattttg      8760 tatttcttgt agagatgagg ttttgccatg ttgcccaggc tggtcttgaa ctcctgggcc      8820
caagtgaccc gcccgccttg acctcccaaa gtgctgggac tgcaggcatg agccacggtg      8880
cctggcccat catagcactt tgatcatta ggataattcc ttctccttgt cattttgga       8940 cacatgcttc ccacatgcct catcttccag agagggtttc caccagggct gtgctgggag      9000
ttaaggctgg aaaagggag atggttccac ctgccagtgc cacatgagtc tactcagggc      9060
tgtaaccagc agggagggtc cagtgtgagc ctcagactcg catgtgggac agacgcccat      9120
gtgtgacaac gctgcagtga atctgtttca cacacatgga ggaggcggct cagggctgac      9180
catggacctg agtcaatgag cagagatatc ccagtgccat ccacaaacac aggggagaag      9240
gagccacaac ttcccacttt catccaaaac cccgacccct ccctgtctgt gagggccctg      9300
gggttctcct ctgtctcata cagaggcaga aacctccccc ttagtgaccc ccagctttgc      9360
aagtcaccag cagcccctcg gcgctggcat cttctgcttc ttaaggtttc ctgcctatga      9420
caggaagtct catttctcat tttcttcatt ggaccatggc tacatatttc agacacatta      9480
taagtaggtt ttcccagtgt taggagcaga tgtgggctgt tgagcacata agtcactcac      9540
```

<210> SEQ ID NO 2
<211> LENGTH: 101
<212> TYPE: PRT
<213> ORGANISM: Homo sapiens

<400> SEQUENCE: 2

```
Gly Ala Tyr Pro Lys Pro Thr Leu Ser Ala Gln Pro Ser Pro Val Val
1               5                   10                  15

Thr Ser Gly Gly Arg Val Thr Leu Gln Cys Glu Ser Gln Val Ala Phe
            20                  25                  30

Gly Gly Phe Ile Leu Cys Lys Glu Gly Glu Asp Glu His Pro Gln Cys
        35                  40                  45

Leu Asn Ser Gln Pro His Ala Arg Gly Ser Ser Arg Ala Ile Phe Ser
    50                  55                  60

Val Gly Pro Val Ser Pro Asn Arg Arg Trp Ser His Arg Cys Tyr Gly
65                  70                  75                  80

Tyr Asp Leu Asn Ser Pro Tyr Val Trp Ser Ser Pro Ser Asp Leu Leu
                85                  90                  95

Glu Leu Leu Val Pro
            100
```

<210> SEQ ID NO 3
<211> LENGTH: 23
<212> TYPE: DNA
<213> ORGANISM: Homo sapiens

<400> SEQUENCE: 3

```
gagtcacagg tggcatttgg cgg                                              23
```

<210> SEQ ID NO 4
<211> LENGTH: 23
<212> TYPE: DNA
<213> ORGANISM: Homo sapiens

<400> SEQUENCE: 4

```
cgaatcgcag gtggtcgcac agg                                              23
```

<210> SEQ ID NO 5
<211> LENGTH: 20
<212> TYPE: DNA
<213> ORGANISM: Homo sapiens

<400> SEQUENCE: 5
gggagcccca tttaacacga                                                  20

<210> SEQ ID NO 6
<211> LENGTH: 20
<212> TYPE: DNA
<213> ORGANISM: Homo sapiens

<400> SEQUENCE: 6
gggagactca gggaactcca                                                  20

<210> SEQ ID NO 7
<211> LENGTH: 7375
<212> TYPE: DNA
<213> ORGANISM: Homo sapiens

<400> SEQUENCE: 7
ctttggacct tcttcaactc tgttttgtct ctgttgagtt aaggctttta agaacacctg      60
aattctttcc ttctgcaaaa ccagaggcag cttcttttcc gcctattttc agtttatttc     120
ttgtgatttt agttttttttc tcttaaccaa atgctaaatg gatttaggag aaataaactt    180
atttgtaaag ctgtcaaggg accattagaa ggatggtgct tcacagatag aatacagttt    240
ttattaatga tgcctagaca aatcctgcca ttagcccaag ggctcagaaa gttagcagcc    300
tagtagtttt ggagttgtca atgaaatgaa ttggactgga tggttaagga tgcccagaag    360
attgaataaa attgggattt aggaggaccc ttgtactcca ggaaattctc caagtctcca    420
cttagttatc cagatcctca aagtgaacat gaagcttcag tttcaaattg aatacatttt    480
ccatccatgg attggcttgt tttgttcagt tgagtgcttg aggttgtctt ttcgacgtaa    540
cagctaaacc cacggcttcc tttctcgtaa aaccaaaaca aaaggctttt ctattcaagt    600
gccttctgtg tgtgcacatg tgtaatacat atctgggatc aaagctatct atataaagtc    660
cttgattctg tgtgggttca aacacatttc aaagcttcag gatcctgaaa ggttttgctc    720
tacttcctga agacctgaac accgctccca taaagccatg gcttgccttg gatttcagcg    780
gcacaaggct cagctgaacc tggctaccag gacctggccc tgcactctcc tgttttttct    840
tctcttcatc cctgtcttct gcaaaggtga gtgagacttt tggagcatga agatggagga    900
ggtgtttctc ctacctgggt ttcatttgtt tcagcagtca aaggcagtga tttatagcaa    960
agccagaagt taaaggtaaa actccaatct ggcttggctg gctctgtatt ccagggccag   1020
cagggagcag ttgggcggca gcaaataagg caaagagata gctcagaaca gagcgccagg   1080
tatttagtag gggcttcatg aatgcatgtg agttggttta gtagagagac acaggcaatt   1140
tcagaccctt ctatgagact ggaagtgatt taagagggaa aggatagcca tagtcctgaa   1200
tacatttgag ctgggtttca ggatgagctc acaagttcct ttaaaaaaaa ttgacttaag   1260
caaatcctgg gaagagtttt tttgctatac aattcaaggt tttaaggtcc tcggattcat   1320
atactttata aatgaattag ccagcttgtt taaaatgtag ggaaattgtg ggaagaatgc   1380
cttctttact taattcaagg ttttaaggtt ctcttaatca attctactag ctaattagcc   1440
aattatttaa aataaaaagt ttgaaattgc caaaaaaaaa agacaaggaa aaggaaagaa   1500
agaaagccac cagtctgttt ggcatacaat acttaattgt tgcctgacct acgtgtgggt   1560

```
ttcagatgca gatcctcagt tttcagctct tcagagactg acaccaggtt tgttacacgg    1620
cttaaaatga tgagtatatc cattgaatct caaccttatc tctctctaga ccttcttggt    1680
taagaaacca tgtagtttgt atgaagtagg tactcaaaag atatttgatg atttaatttt    1740
tactggagaa gaaatattca tatatgtttt cttatttta catgttttaa atatgtaaag    1800
attaaataaa cactcttaga agtatttaaa tttcctaaag taaatttatc tcaaccagta    1860
acaggaccct cccaatactg gaaagttgag tgtgaccgca tttagtggtg atgagtgtga    1920
gcttgcttgg ggagagggca ggacatttag gatttcttaa gcttagagtc aatacaataa    1980
agattattga gtgctcactt gggtgggcta aatcactgc tcacaggagt tcatgaacca    2040
caagtaaaag agtgaggaga tatgattagc tcacaaataa ctttaataca gagcagaaag    2100
taatgaacta ctgcaatgga gttatcacag tgctaaggat gctcagaggg catctctgat    2160
aggcagaggt gagggttagg gaaggaagct gtagtctagc tagctagagc tgctggaata    2220
gacatgacaa tggctgctgc caaactgttt tctcttctga ggacagatgt cccgtgcaag    2280
tggcttggtg gaagggacta gtgtctctaa tagggtgta tttataagca ggaaagtgtg    2340
tcctagaaat tcagaccaga gtgatagatt ggaattggat catgggggac tcattgaatg    2400
ttatttattg tatttgtttt tgcgatcagt gttagtaaag tgtcaaaggg attgagcaga    2460
tgagtgacat catgcaacac aagttttgag tttcacttgt cagactgact ggagaggggc    2520
ctggttagtt acaggaaggt aatttggcat gcagccacta ttttgagtt gatgcaagcc    2580 tctctgtatg gagagctggt ctcctttatc ctgtgggaaa agagaacaaa ggagcatggg    2640
agtgttcaag ggaaggagaa ataaagggca gagaggcagc ggtggtgtca ggggaagccc    2700
acaggagtta acagcagggt tgcctcaacc tagagaggaa gcgacctggt gccctcggct    2760
ctgtggcttc cttcatctaa caacatcttc cactctacaa caatgccagg gaaggcggag    2820
gctggtacag tgcatcaaga cacagctact cctgggtgac agaggttcag ggccagctca    2880
ctaagtaggc agaagttttt gacatatact ttgagagata aagcaagatt ctgtacctca    2940
accttcagaa tttcccctac cactcattat agttccggag ctatatagct cctatcattc    3000
tatcataacc ttagaatacc agagaacata tcatctcatc taattatctc ttactatatg    3060
tgaaaaaaat gaaggacatg ggggaagtgt gacttgcccc aaatcacata tttcatggta    3120
gagccaggtc ttctgtttgt catatcagtg ttcttcctgc cacaaccatc ttgaagaatc    3180
tatttctcag taagaaaata tctttatgga gagtagctgg aaaacagttg agagatggag    3240
gggaggctgg gggtgtggag aggggaaggg gtaagtgata gattcgttga agggggagga    3300
aaaggccgtg gggatgaagc tagaaggcag aagggcttgc ctgggcttgg ccatgaagga    3360
gcatgagttc actgagttcc ctttggcttt tccatgctag caatgcacgt ggcccagcct    3420
gctgtggtac tggccagcag ccgaggcatc gccagctttg tgtgtgagta tgcatctcca    3480
ggcaaagcca ctgaggtccg ggtgacagtg cttcggcagg ctgacagcca ggtgactgaa    3540
gtctgtgcgg caacctacat gatggggaat gagttgacct tcctagatga ttccatctgc    3600
acgggcacct ccagtggaaa tcaagtgaac ctcactatcc aaggactgag ggccatggac    3660 acggactct acatctgcaa ggtggagctc atgtacccac cgccatacta cctgggcata    3720
ggcaacggaa cccagattta tgtaattggt gagcaaagcc atttcactga gttgacacct    3780
gttgcattgc agtcttctat gcacaaaaac agttttgttc cttaatttca ggaggtttac    3840
ttttaggact gtggacattc tctttaagag ttctgtacca catggtagcc ttgcttattg    3900
tgggtggcaa ccttaatagc attctgactg taaaataaaa tgatttgggg aagttgggc    3960
```

```
tctcgctctg gagtgctaac catcatgacg tttgatctgt acttttgata tgatatgatg    4020
ctcctgggga agtagtccca aatagccaaa cctattggtg ggctacccat gcaatttagg    4080
ggtggacctc aaggcctgga agctctaatg tccttttttc accaatgttg gggagtagag    4140
ccctagagtt taaaactgtc tcagggaggc tctgctttgt tttctgttgc agatccagaa    4200
ccgtgcccag attctgactt cctcctctgg atccttgcag cagttagttc ggggttgttt    4260
ttttatagct ttctcctcac agctgtttct ttgagcaaaa tggtgagtgt ggtgctgatg    4320
gtgcaccatg tctgatgggg atacctttag tggtatcaac tggccaaaag atgatgttga    4380
gtttagtgtt cttgagatga gatgaggcaa taaatgaaga ggaaggacag tggtaaagaa    4440
cgcactagaa ccgtaggcat tggcatttga ggtttcagaa tgactaatat tttagatgaa    4500
tttgtttgac attgaatgtt catgtgcttc tgagcagggt ttcaatttga gtaaccgttg    4560
caataacatg gggcagctgt tttgctcttt gtcttcatga caactgtact taagctaaca    4620
gccctgaaac atgagattag ctgggcagaa atgctgctag agaggaccac ttggatggtc    4680
tttattctcc ttctccatgt ccctctccat cacctggaag tcacctctgg gtgccactct    4740
ggtgccttcc ttgtcgaagc tgtagctgct cacatgacac ctatccctgt tatccagttt    4800
gcttgactgg gacgttttgc cttccccttc agccaggaag tgaaagtccc agttttattt    4860
tatcacaggt gttggtattg gtggtagaag aggtagaatt atggaatcag gcctcctgtc    4920
aggatttctt tttgacagtc cctctcagac acctctgcct aaggccagct tgccattac    4980 aaactctccc ttctccctct ctcccttctt ctcttcctct tccttcttct cgctcttct    5040 ctctctctct ttctccctct ctgtctctta tacacataca caaagatata ctctattcca    5100
acatcctcta cccaacctga cagagatgtc ctttgctgta ggttcagcag tggggatgag    5160
aaatacagct ctcaaacagg ataactaaag cttattatct tatcaagctt gttcccttgc    5220
agacaagatt gatcaattat cataggcttt ctgggtgttc tttctgaagc tttctcaaag    5280
tctctttctc ctatcttcca ttcaaggcaa atgattgcca tttaacatca aaatcacagt    5340
tatttatcta aaataaattt taatagctga atcaagaaaa tctcctgagg tttataattc    5400
tgtatgctgt gaacattcat ttttaaccag ctagggaccc aatatgtgtt gagttctatt    5460
atggttagaa gtggcttccg tattcctcag tagtaattac tgtttctttt tgtgtttgac    5520
agctaaagaa aagaagccct cttacaacag gggtctatgt gaaaatgccc ccaacagagc    5580
cagaatgtga aaagcaattt cagccttatt ttattcccat caattgagaa accattatga    5640
agaagagagt ccatatttca atttccaaga gctgaggcaa ttctaacttt tttgctatcc    5700
agctattttt atttgtttgt gcatttgggg ggaattcatc tctctttaat ataaagttgg    5760
atgcggaacc caaattacgt gtactacaat ttaaagcaaa ggagtagaaa acagagctg     5820 ggatgtttct gtcacatcag ctccactttc agtgaaagca tcacttggga ttaatatggg    5880
gatgcagcat tatgatgtgg gtcaaggaat taagttaggg aatggcacag cccaaagaag    5940
gaaaaggcag ggagcgaggg agaagactat attgtacaca ccttatattt acgtatgaga    6000
cgtttatagc cgaaatgatc ttttcaagtt aaatttatg cctttattt cttaaacaaa     6060 tgtatgatta catcaaggct tcaaaaatac tcacatggct atgttttagc cagtgatgct    6120
aaaggttgta ttgcatatat acatatatat atatatatat atatatat atatatatat     6180 atatatatat atatatattt taatttgata gtattgtgca tagagccacg tatgtttttg    6240
tgtatttgtt aatggtttga atataaacac tatatggcag tgtctttcca ccttgggtcc    6300
```

```
caggaagtt ttgtggagga gctcaggaca ctaatacacc aggtagaaca caaggtcatt      6360
tgctaactag cttggaaact ggatgaggtc atagcagtgc ttgattgcgt ggaattgtgc      6420
tgagttggtg ttgacatgtg ctttggggct tttacaccag ttcctttcaa tggtttgcaa      6480
ggaagccaca gctggtggta tctgagttga cttgacagaa cactgtcttg aagacaatgg      6540
cttactccag gagacccaca ggtatgacct tctaggaagc tccagttcga tgggcccaat      6600
tcttacaaac atgtggttaa tgccatggac agaagaaggc agcaggtggc agaatggggt      6660
gcatgaaggt ttctgaaaat taacactgct tgtgttttta actcaatatt ttccatgaaa      6720
atgcaacaac atgtataata ttttaattta aataaaaatc tgtggtggtc gttttccgga      6780 gttgtctttta tcatccttgc atttgaatat tgtgttcaaa ttttttgattg attcattcag      6840 tatctggtgg agtctccaat attagaaata ctggaaacaa actgaaaaac cacaaaagga      6900
caaataatgc ttcatgagtc agctttgcac cagccattac ctgcaagtca ttcttggaag      6960
gtatccatcc tctttccttt tgatttcttc accactattt gggatataac gtgggttaac      7020
acagacatag cagtccttta taaatcaatt ggcatgctgt ttaacacagg ttcttcacct      7080
cccctttctt accgcctgct ttctcagctc aactatcaca ggcattacag ttgtcatggc      7140
aaccccaatg ttggcaacca cgtcccttgc agccattttg atctgccttc ctgaaatata      7200
gagcttttcc ctgtggcttc caaatgaact attttgcaaa tgtggggaaa acacacacct      7260 gtggtccctat gttgctatca gctggcacac ctaggcctgg cacactaagc cctctgtgat      7320
tcttgcttaa ccaatgtata gtctcagcac atttggtttc cacttaaggt ttcct           7375

<210> SEQ ID NO 8
<211> LENGTH: 36
<212> TYPE: PRT
<213> ORGANISM: Homo sapiens

<400> SEQUENCE: 8

Met Ala Cys Leu Gly Phe Gln Arg His Lys Ala Gln Leu Asn Leu Ala
1               5                   10                  15

Thr Arg Thr Trp Pro Cys Thr Leu Leu Phe Phe Leu Leu Phe Ile Pro
            20                  25                  30

Val Phe Cys Lys
        35

<210> SEQ ID NO 9
<211> LENGTH: 23
<212> TYPE: DNA
<213> ORGANISM: Homo sapiens

<400> SEQUENCE: 9
cactcacctt tgcagaagac agg                                              23

<210> SEQ ID NO 10
<211> LENGTH: 23
<212> TYPE: DNA
<213> ORGANISM: Homo sapiens

<400> SEQUENCE: 10
ccttgtgccg ctgaaatcca agg                                              23

<210> SEQ ID NO 11
<211> LENGTH: 29
<212> TYPE: DNA
<213> ORGANISM: Homo sapiens
```

<400> SEQUENCE: 11
aggacccttg tactccagga aattctcca                                              29

<210> SEQ ID NO 12
<211> LENGTH: 26
<212> TYPE: DNA
<213> ORGANISM: Homo sapiens

<400> SEQUENCE: 12
agccccract aaatacctgg cgctct                                                 26

<210> SEQ ID NO 13
<211> LENGTH: 846
<212> TYPE: DNA
<213> ORGANISM: Homo sapiens

<400> SEQUENCE: 13

```
atggctatga tggaggtcca gggggaccc agcctgggac agacctgcgt gctgatcgtg      60
atcttcacag tgctcctgca gtctctctgt gtggctgtaa cttacgtgta ctttaccaac     120
gagctgaagc agatgcagga caagtactcc aaaagtggca ttgcttgttt cttaaaagaa     180
gatgacagtt attgggaccc caatgacgaa gagagtatga cagcccctg ctggcaagtc     240
aagtggcaac tccgtcagct cgttagaaag atgattttga acctctga ggaaaccatt      300
tctacagttc aagaaaagca acaaatatt tctcccctag tgagagaaag aggtcctcag     360
agagtagcag ctcacataac tgggaccaga ggaagaagca acacattgtc ttctccaaac    420
tccaagaatg aaaaggctct gggccgcaaa ataaactcct gggaatcatc aaggagtggg    480
cattcattcc tgagcaactt gcacttgagg aatggtgaac tggtcatcca tgaaaaaggg    540
ttttactaca tctattccca acatactttt cgatttcagg aggaaataaa agaaaacaca    600
aagaacgaca acaaatggt ccaatatatt tacaaataca caagttatcc tgaccctata    660
ttgttgatga aaagtgctag aaatagttgt tggtctaaag atgcagaata tggactctat    720
tccatctatc aaggggaat atttgagctt aaggaaaatg acagaatttt tgtttctgta    780
acaaatgagc acttgataga catggaccat gaagccagtt ttttcgggc cttttttagtt    840
ggctaa                                                               846
```

<210> SEQ ID NO 14
<211> LENGTH: 846
<212> TYPE: DNA
<213> ORGANISM: Homo sapiens

<400> SEQUENCE: 14

```
atggctatga tggaggtcca gggggaccc agcctgggac agacctgcgt gctgatcgtg      60
atcttcacag tgctcctgca gtctctctgt gtggctgtaa cttacgtgta ctttaccaac     120
gagctgaagc agatgcagga caagtactcc aaaagtggca ttgcttgttt cttaaaagaa     180
gatgacagtt attgggaccc caatgacgaa gagagtatga cagcccctg ctggcaagtc     240
aagtggcaac tccgtcagct cgttagaaag atgattttga acctctga ggaaaccatt      300
tctacagttc aagaaaagca acaaatatt tctcccctag tgagagaaag aggtcctcag     360
agagtagcag ctcacataac tgggaccaga cgaagaagca acacattgtc ttctccaaac    420
tccaagaatg aaaaggcct gggcatcaaa ataaactcct gggaatcatc aaggagaggg    480
cattcattcc tgagcaactt gcacttgagg aatggtgaac tggtcatcca tgaaaaaggg    540
ttttactaca tctattccca acatactttt cgatttcagg aggaaataaa agaaaacaca    600
```

-continued

```
aagaacgaca aacaaatggt ccaatatatt tacaaataca cagactatcc tgaccctata    660
ttgttgatga aaagtgctag aaatagttgt tggtctaaag atgcagaata tggactctat    720
tccatctatc aaggggaat atttgagctt aaggaaaatg acagaatttt tgtttctgta     780
acaaatgagc acttgataga catggaccat gaagccagtt ttttcggggc cttttagtt    840 ggctaa                                                                846
```

MODIFIED NATURAL KILLER CELLS AND NATURAL KILLER CELL LINES HAVING INCREASED CYTOTOXICITY

INTRODUCTION

The present invention relates to the modification of natural killer (NK) cells and NK cell lines to produce derivatives thereof with a more cytotoxic phenotype. Furthermore, the present invention relates to methods of producing modified NK cells and NK cell lines, compositions containing the cells and cell lines and uses of said compositions in the treatment of cancer.

BACKGROUND TO THE INVENTION

Typically, immune cells require a target cell to present antigen via major histocompatibility complex (MHC) before triggering an immune response resulting in the death of the target cell. This allows cancer cells not presenting MHC class I to evade the majority of immune responses.

NK cells are able, however, to recognize cancer cells in the absence of MHC class I expression. Hence they perform a critical role in the body's defence against cancer.

On the other hand, in certain circumstances, cancer cells demonstrate an ability to dampen the cytotoxic activity of NK cells, through expression of ligands that bind inhibitory receptors on the NK cell membrane. Resistance to cancer can involve a balance between these and other factors.

Cytotoxicity, in this context, refers to the ability of immune effector cells, e.g. NK cells, to induce cancer cell death, e.g. by releasing cytolytic compounds or by binding receptors on cancer cell membranes and inducing apoptosis of said cancer cells. Cytotoxicity is affected not only by signals that induce release of cytolytic compounds but also by signals that inhibit their release. An increase in cytotoxicity will therefore lead to more efficient killing of cancer cells, with less chance of the cancer cell dampening the cytotoxic activity of the NK, as mentioned above.

Genetic modification to remove inhibitory receptor function on NK cells has been suggested as a method for increasing the cytotoxicity of NK cells against cancer cells that lack MHC class I expression but are able to dampen NK cytotoxicity (Bodduluru et al. 2012). NKG2A has been established as an inhibitory receptor worth silencing under these circumstances, as certain cancer cells are known to express MICA which binds NKG2A and inhibits NK cell cytotoxicity in the absence of MHC class I expression (Shook et al. 2011; WO 2006/023148).

Another method of downregulating NKG2A expression has been shown in NK-92 cells, in which transfection with a gene encoding IL-15 was shown to be associated with a reduction in NKG2A expression (Zhang et al. 2004). However, despite an observed increase in the cytotoxicity of the NK cells, the increase was likely a result of a concomitant increase in expression of the activating receptor NKG2D. This is supported by the observation that blocking NKG2A receptors on NK-92 cells was not associated with an increase in cytotoxicity against multiple myeloma cells (Heidenreich et al. 2012). Nevertheless, it is worth noting that the NK-92 cell line is a highly cytotoxic cell line with very low expression of inhibitory receptors. Therefore, any increase in cytotoxicity associated with decreased NKG2A expression might have been too trivial to detect.

Similar studies have been carried out in mice. For example, mice express a receptor called Ly49 on NK cells, which is analogous to human inhibitory KIR receptors. It has been shown that by blocking the Ly49 receptor with antibody fragments, NK cells are more cytotoxic and capable of killing murine leukemia cells in vitro and in vivo (Koh et al. 2001).

It is a consequence of reducing inhibitory receptor function, however, that 'normal' cells in the body also become more susceptible to attack by modified NK cells, as the modified NK cells become less capable of distinguishing between 'normal' cells and cancer cells. This is a significant disadvantage of reducing 'classical' inhibitory receptor function.

Another way in which NK cells are known to kill cancer cells is by expressing TRAIL on their surface. TRAIL ligand is able to bind TRAIL receptors on cancer cells and induce apoptosis of said cancer cells. One speculative approach describes overexpressing TRAIL on NK cells, in order to take advantage of this anti-cancer mechanism (EP1621550). Furthermore, IL-12 has been reported to upregulate TRAIL expression on NK cells (Smyth et al. 2001).

Nevertheless, cancer cells have developed evasive and protective mechanisms for dealing with NK cells expressing TRAIL. Decoy TRAIL receptors are often expressed on cancer cell membranes, and binding of TRAIL to these decoy receptors is unable to induce apoptosis; methods of overcoming such mechanisms have not yet been pursued.

Acute myeloid leukemia (AML) is a hematopoietic malignancy involving precursor cells committed to myeloid development, and accounts for a significant proportion of acute leukemias in both adults (90%) and children (15-20%) (Hurwitz, Mounce et al. 1995; Lowenberg, Downing et al. 1999). Despite 80% of patients achieving remission with standard chemotherapy (Hurwitz, Mounce et al. 1995; Ribeiro, Razzouk et al. 2005), survival remains unsatisfactory because of high relapse rates from minimal residual disease (MRD). The five-year survival is age-dependent; 60% in children (Rubnitz 2012), 40% in adults under 65 (Lowenberg, Downing et al. 1999) and 10% in adults over 65 (Ferrara and Schiffer 2013). These outcomes can be improved if patients have a suitable hematopoietic cell donor, but many do not, highlighting the need for an alternative approach to treatment.

Natural killer (NK) cells are cytotoxic lymphocytes, with distinct phenotypes and effector functions that differ from e.g. natural killer T (NK-T) cells. For example, while NK-T cells express both CD3 and T cell antigen receptors (TCRs), NK cells do not. NK cells are generally found to express the markers CD16 and CD56, wherein CD16 functions as an Fc receptor and mediates antibody dependent cell-mediated cytotoxicity (ADCC) which is discussed below. KHYG-1 is a notable exception in this regard. Despite NK cells being naturally cytotoxic, NK cell lines with increased cytotoxicity have been developed. NK-92 and KHYG-1 represent two NK cell lines that have been researched extensively and show promise in cancer therapeutics (Swift et al. 2011; Swift et al. 2012).

Adoptive cellular immunotherapy for use in cancer treatment commonly involves administration of natural and modified T cells to a patient. T cells can be modified in various ways, e.g. genetically, so as to express receptors and/or ligands that bind specifically to certain target cancer cells. Transfection of T cells with high-affinity T cell receptors (TCRs) and chimeric antigen receptors (CARs), specific for cancer cell antigens, can give rise to highly reactive cancer-specific T cell responses. A major limitation of this immunotherapeutic approach is that T cells must either be obtained from the patient for autologous ex vivo expansion or MHC-matched T cells must be used to avoid immunological eradication immediately following transfer of the cells to the patient or, in some cases, the onset of graft-vs-host disease (GVHD). Additionally, successfully transferred T cells often survive for prolonged periods of time in the circulation, making it difficult to control persistent side-effects resulting from treatment.

In haplotype transplantation, the graft-versus-leukemia effect is believed to be mediated by NK cells when there is a KIR inhibitory receptor-ligand mismatch, which can lead to improved survival in the treatment of AML (Ruggeri, Capanni et al. 2002; Ruggeri, Mancusi et al. 2005). Furthermore, rapid NK recovery is associated with better outcome and a stronger graft-vs-leukemia (GVL) effect in patients undergoing haplotype T-depleted hematopoietic cell transplantation (HCT) in AML (Savani, Mielke et al. 2007). Other trials have used haploidentical NK cells expanded ex vivo to treat AML in adults (Miller, Soignier et al. 2005) and children (Rubnitz, Inaba et al. 2010).

Several permanent NK cell lines have been established, and the most notable is NK-92, derived from a patient with non-Hodgkin's lymphoma expressing typical NK cell markers, with the exception of CD16 (Fc gamma receptor III). NK-92 has undergone extensive preclinical testing and exhibits superior lysis against a broad range of tumours compared with activated NK cells and lymphokine-activated killer (LAK) cells (Gong, Maki et al. 1994). Cytotoxicity of NK-92 cells against primary AML has been established (Yan, Steinherz et al. 1998).

Another NK cell line, KHYG-1, has been identified as a potential contender for clinical use (Suck et al. 2005) but has reduced cytotoxicity so has received less attention than NK-92. KHYG-1 cells are known to be pre-activated. Unlike endogenous NK cells, KHYG-1 cells are polarized at all times, increasing their cytotoxicity and making them quicker to respond to external stimuli. NK-92 cells have a higher baseline cytotoxicity than KHYG-1 cells.

It is therefore clear that current adoptive immunotherapy protocols are affected by donor variability in the quantity and quality of effector cells, variables that could be eliminated if effective cell lines were available to provide more standardized therapy.

A considerable amount of research into NK cell cytotoxicity has been performed using mouse models. One example is the finding that perforin and granzyme B mRNA are constitutively transcribed in mouse NK cells, but minimal levels of protein are detected until stimulation or activation of the NK cells (Fehniger et al, 2007). Although this work and other work using mouse NK cells is of interest, it cannot be relied upon as conclusive evidence for NK cell cytotoxicity in humans. In contrast to the above example, human NK cells express high levels of perforin and granzyme B protein prior to stimulation (Leong et al, 2011). The result being that when either mouse or human NK cells are freshly isolated in culture, the mouse NK cells have weak cytolytic activity, whereas the human NK cells exhibit strong cytolytic capabilities.

Mouse and human NK cells also vary greatly in their expression markers, signalling cascades and tissue distribution. For example, CD56 is used as a marker for human NK cells, whereas mouse NK cells do not express this marker at all. Furthermore, a well-established mechanism for regulating NK cell cytotoxicity is via ligand binding NK activation and inhibitory receptors. Two of the most prominent human NK activation receptors are known to be NKp30 and NKp44, neither of which are expressed on mouse NK cells. With regards to NK inhibitory receptors, whilst human NK cells express KIRs that recognise MHC class I and dampen cytotoxic activity, mouse NK cells do not express KIRs at all but, instead, express Ly49s (Trowsdale et al, 2001). All in all, despite mouse NK cells achieving the same function as human NK cells in their natural physiological environment, the mechanisms that fulfil this role vary significantly between species.

Thus there exists a need for alternative and preferably improved human NK cells and human NK cell lines, e.g. with a more cytotoxic profile.

An object of the invention is to provide NK cells and NK cell lines with a more cytotoxic phenotype. A further object is to provide methods for producing modified NK cells and NK cell lines, compositions containing the cells or cell lines and uses of said compositions in the treatment of cancers. More particular embodiments aim to provide treatments for identified cancers, e.g. blood cancers, such as leukemias. Specific embodiments aim at combining two or more modifications of NK cells and NK cell lines to further enhance the cytotoxicity of the modified cells.

SUMMARY OF THE INVENTION

There are provided herein modified NK cells and NK cell lines with a more cytotoxic phenotype, and methods of making the cells and cell lines. Also provided are compositions of modified NK cells and NK cell lines, and uses of said compositions for treating cancer.

The invention provides methods of modifying NK cells and NK cell lines using, for example, genetic engineering to knock out genes encoding inhibitory receptors, express genes encoding TRAIL ligands and variants, and express genes encoding chimeric antigen receptors (CARs) and/or Fc receptors.

Furthermore, compositions of the invention include NK cells and NK cell lines in which two or more modifications are provided, wherein multiple modifications further enhance the cytotoxic activity of the composition.

According to the invention, there are further provided methods of treating cancer, e.g. blood cancer, using modified NK cell lines, e.g. derivatives of KHYG-1 cells, wherein the modified NK cell lines are engineered to lack expression of checkpoint inhibitory receptors, express TRAIL ligand variants and/or express CARs and/or Fc receptors.

Diseases particularly treatable according to the invention include cancers, blood cancers, leukemias and specifically acute myeloid leukemia. Tumours and cancers in humans in particular can be treated. References to tumours herein include references to neoplasms.

Details of the Invention

Accordingly, the present invention provides a natural killer (NK) cell or NK cell line that has been genetically modified to increase its cytotoxicity.

As described in detail below in examples, NK cells and NK cell lines have been genetically modified so as to increase their cytotoxic activity against cancer.

Together, the NK cells and NK cell lines of the invention will be referred to as the NK cells (unless the context requires otherwise).

In certain embodiments of the invention NK cells are provided having reduced or absent checkpoint inhibitory receptor function. Thus in examples below, NK cells are produced that have one or more checkpoint inhibitory receptor genes knocked out. Preferably, these receptors are specific checkpoint inhibitory receptors. Preferably still, these checkpoint inhibitory receptors are one or more or all of CD96 (TACTILE), CD152 (CTLA4), CD223 (LAG-3), CD279 (PD-1), CD328 (SIGLEC7), SIGLEC9, TIGIT and/or TIM-3.

In other embodiments, NK cells are provided in which one or more inhibitory receptor signaling pathways are knocked out or exhibit reduced function—the result again being reduced or absent inhibitory receptor function. For example, signaling pathways mediated by SHP-1, SHP-2 and/or SHIP are knocked out by genetic modification of the cells.

The resulting NK cells exhibit improved cytotoxicity and are of greater use therefore in cancer therapy, especially blood cancer therapy, in particular treatment of leukemias and multiple myeloma.

In an embodiment, the genetic modification occurs before the cell has differentiated into an NK cell. For example, pluripotent stem cells (e.g. iPSCs) can be genetically modified to lose the capacity to express one or more checkpoint inhibitory receptors. The modified iPSCs are then differentiated to produce genetically modified NK cells with increased cytotoxicity.

It is preferred to reduce function of checkpoint inhibitory receptors over other inhibitory receptors, due to the expression of the former following NK cell activation. The normal or 'classical' inhibitory receptors, such as the majority of the KIR family, NKG2A and LIR-2, bind MHC class I and are therefore primarily involved in reducing the problem of self-targeting. Preferably, therefore, checkpoint inhibitory receptors are knocked out. Reduced or absent function of these receptors according to the invention prevents cancer cells from suppressing immune effector function (which might otherwise occur if the receptors were fully functional). Thus a key advantage of these embodiments of the invention lies in NK cells that are less susceptible to suppression of their cytotoxic activities by cancer cells; as a result they are useful in cancer treatment.

As used herein, references to inhibitory receptors generally refer to a receptor expressed on the plasma membrane of an immune effector cell, e.g. a NK cell, whereupon binding its complementary ligand resulting intracellular signals are responsible for reducing the cytotoxicity of said immune effector cell. These inhibitory receptors are expressed during both 'resting' and 'activated' states of the immune effector cell and are often associated with providing the immune system with a 'self-tolerance' mechanism that inhibits cytotoxic responses against cells and tissues of the body. An example is the inhibitory receptor family 'KIR' which are expressed on NK cells and recognize MHC class I expressed on healthy cells of the body.

Also as used herein, checkpoint inhibitory receptors are usually regarded as a subset of the inhibitory receptors above. Unlike other inhibitory receptors, however, checkpoint inhibitory receptors are expressed at higher levels during prolonged activation and cytotoxicity of an immune effector cell, e.g. a NK cell. This phenomenon is useful for dampening chronic cytotoxicity at, for example, sites of inflammation. Examples include the checkpoint inhibitory receptors PD-1, CTLA-4 and CD96, all of which are expressed on NK cells.

The invention hence also provides a NK cell lacking a gene encoding a checkpoint inhibitory receptor selected from CD96 (TACTILE), CD152 (CTLA4), CD223 (LAG-3), CD279 (PD-1), CD328 (SIGLEC7), SIGLEC9, TIGIT and TIM-3.

A NK cell lacking a gene can refer to either a full or partial deletion, mutation or otherwise that results in no functional gene product being expressed. In embodiments, the NK cell lacks genes encoding two or more of the inhibitory receptors.

More specific embodiments comprise a NK cell lacking a gene encoding a checkpoint inhibitory receptor selected from CD96 (TACTILE), CD152 (CTLA4) and CD279 (PD-1). Preferred embodiments comprise a NK cell being a derivative of KHYG-1.

In examples described below, the inventors have reliably shown the cytotoxic effects of using siRNA to knock down expression of the checkpoint inhibitory receptor CD96 in KHYG-1 cells. CD96 knockdown (KD) KHYG-1 cells demonstrated enhanced cytotoxicity against leukemia cells at a variety of effector:target (E:T) ratios.

In other embodiments of the invention NK cells are provided that express a TRAIL ligand or, preferably, a mutant (variant) TRAIL ligand. As further described in examples below, cytotoxicity-enhancing modifications of NK cells hence also include increased expression of both TRAIL ligand and/or mutated TRAIL ligand variants.

The resulting NK cells exhibit increased binding to TRAIL receptors and, as a result, increased cytotoxicity against cancers, especially blood cancers, in particular leukemias.

The mutants/variants preferably have lower affinity (or in effect no affinity) for 'decoy' receptors, compared with the binding of wild type TRAIL to decoy receptors. Such decoy receptors represent a class of TRAIL receptors that bind TRAIL ligand but do not have the capacity to initiate cell death and, in some cases, act to antagonize the death signaling pathway. Mutant/variant TRAIL ligands may be prepared according to WO 2009/077857.

The mutants/variants may separately have increased affinity for TRAIL receptors, e.g. DR4 and DR5. Wildtype TRAIL is typically known to have a $K_D$ of >2 nM for DR4, >5 nM for DR5 and >20 nM for the decoy receptor DcR1 (WO 2009/077857; measured by surface plasmon resonance), or around 50 to 100 nM for DR4, 1 to 10 nM for DR5 and 175 to 225 nM for DcR1 (Truneh, A. et al. 2000; measured by isothermal titration calorimetry and ELISA). Therefore, an increased affinity for DR4 is suitably defined as a $K_D$ of <2 nM or <50 nM, respectively, whereas an increased affinity for DR5 is suitably defined as a $K_D$ of <5 nM or <1 nM, respectively. A reduced affinity for decoy receptor DcR1 is suitably defined as a $K_D$ of >50 nM or >225 nM, respectively. In any case, an increase or decrease in affinity exhibited by the TRAIL variant/mutant is relative to a baseline affinity exhibited by wildtype TRAIL. The affinity is preferably increased at least 10%, at least 25%, at least 50%, more preferably at least 100% compared with that exhibited by wildtype TRAIL.

The TRAIL variant preferably has an increased affinity for DR5 as compared with its affinity for DR4, DcR1 and DcR2. Preferably, the affinity is at least 1.5-fold, 2-fold, 5-fold, 10-fold, 100-fold, or even 1,000-fold or greater for DR5 than for one or more of DR4, DcR1 and DcR2. More preferably, the affinity is at least 1.5-fold, 2-fold, 5-fold, 10-fold, 100-fold, or even 1,000-fold or greater for DR5 than for at least two, and preferably all, of DR4, DcR1 and DcR2.

The TRAIL variant preferably has an increased affinity for one or both of DR4 and DR5 as compared with its affinity for wildtype TRAIL. Preferably, the affinity is at least 1.5-fold, 2-fold, 5-fold, 10-fold, 100-fold, or even 1,000-fold or greater for DR4 and/or DR5 than for wildtype TRAIL.

A key advantage of these embodiments of the invention lies in NK cells that have greater potency in killing cancer cells.

Further specific embodiments comprise a NK cell expressing a mutant TRAIL ligand that has reduced or no affinity for TRAIL decoy receptors. Preferably, this NK cell is a derivative of KHYG-1. Further specific embodiments comprise a NK cell expressing a mutant TRAIL ligand that has reduced or no affinity for TRAIL decoy receptors and increased affinity for DR4 and/or DR5.

In certain embodiments, the TRAIL variant comprises at least one amino acid substitution at a position selected from the group consisting of 131, 149, 159, 160, 189, 191, 193, 195, 199, 200, 201, 203, 204, 212, 213, 214, 215, 218, 240, 251, 261, 264, 266, 267, 269, and 270.

In certain embodiments, the TRAIL variant comprises at least one substitution selected from the group consisting of G131R, G131K, R149I, R149M, R149N, R149K, S159R, G160E, Y189A, Y189Q, R191K, Q193H, Q193K, Q193S, Q193R, E195R, N199V, N199R, N199H, T200H, K201R, K201H, D203A, K204E, K204D, K204Y, K212R, Y213W, T214R, S215D, S215E, S215H, S215K, S215D, D218H, D218A, Y240A, K251D, K251E, K251Q, T261L, H264R, I266L, D267Q, D269A, D269H, and H270D.

In certain embodiments, the TRAIL variant comprises at least two substitutions selected from the group consisting of G131R, G131K, R149I, R149M, R149N, R149K, S159R, G160E, Y189A, Y189Q, R191K, Q193H, Q193K, Q193S, Q193R, E195R, N199V, N199R, N199H, T200H, K201R, K201H, D203A, K204E, K204D, K204Y, K212R, Y213W, T214R, S215D, S215E, S215H, S215K, S215D, D218H, D218A, Y240A, K251D, K251E, K251Q, T261L, H264R, I266L, D267Q, D269A, D269H, and H270D.

In certain embodiments, the TRAIL variant comprises at least three substitutions selected from the group consisting of G131R, G131K, R149I, R149M, R149N, R149K, S159R, G160E, Y189A, Y189Q, R191K, Q193H, Q193K, Q193S, Q193R, E195R, N199V, N199R, N199H, T200H, K201R, K201H, D203A, K204E, K204D, K204Y, K212R, Y213W, T214R, S215D, S215E, S215H, S215K, S215D, D218H, D218A, Y240A, K251D, K251E, K251Q, T261L, H264R, I266L, D267Q, D269A, D269H, and H270D.

In certain embodiments, amino acid substitution of the TRAIL variant is selected from the group consisting of G131R, G131K, R149I, R149M, R149N, R149K, S159R, G160E, Y189A, Y189Q, R191K, Q193H, Q193K, Q193S, Q193R, E195R, N199V, N199R, N199H, T200H, K201R, K201H, D203A, K204E, K204D, K204Y, K212R, Y213W, T214R, S215D, S215E, S215H, S215K, S215D, D218H, D218A, Y240A, K251D, K251E, K251Q, T261L, H264R, I266L, D267Q, D269A, D269H, H270D, T214R/E195R, T214R/D269H, Y189A/Q193S/N199V/K201R/Y213W/S215D, Y213W/S215D, N199R/K201H, N199H/K201R, G131R/N199R/K201H, G131R/N199R/K201H/R149I/S159R/S215D, G131R/R149I/S159R/S215D, G131R/N199R/K201H/R149I/S159R/S215D, G131R/D218H, Y189Q/R191K/Q193R/H264R/I266L/D267Q, T261L/G160E, T261L/H270D, T261L/G160E/H270D, and T261L/G160E/H270D/T200H (use of "/" indicates multiple amino acid substitutions).

In certain embodiments, amino acid substitution of the TRAIL variant is selected based on the variant having an increased affinity for DR5; a substitution of this kind may be selected from the group consisting of D269H, E195R, T214R, D269H/E195R, T214R/E195R, T214R/D269H, N199V, Y189A/Q193S/N199V/K201R/Y213W/S215D, Y213W/S215D, D269A and Y240A.

In certain embodiments, amino acid substitution of the TRAIL variant is selected based on the variant having an increased affinity for DR4; a substitution of this kind may be selected from the group consisting of G131R, G131K, R149I, R149M, R149N, R149K, S159R, Q193H, W193K, N199R, N199R/K201H, N199H/K201R, G131R/N199R/K201H, G131R/N199R/K201H, G131R/N199R/K201H/R149I/S159R/S215D, G131R/R149I/S159R/S215D, G131R/D218H, K201R, K201H, K204E, K204D, K204L, K204Y, K212R, S215E, S215H, S215K, S215D, D218H, K251D, K251E, K251Q and Y189Q/R191K/Q193R/H264R/I266L/D267Q.

In certain embodiments, amino acid substitution of the TRAIL variant is selected based on the variant having a decreased affinity for TRAIL decoy receptors; a substitution of this kind may be selected from the group consisting of T261L, H270D, T200H, T261L/G160E, T261L/H270D, T261L/G160E/H270D, T261L/G160E/H270D/T200H, D203A and D218A.

In examples of the invention, described in more detail below, NK cells were genetically modified to express a mutant TRAIL. Modified KHYG-1 cells expressed mutant TRAIL, and NK-92 expressed a mutant TRAIL. The modified KHYG-1 cells exhibited improved cytotoxicity against cancer cell lines in vitro. KHYG-1 cells express TRAIL receptors (e.g. DR4 and DR5), but at low levels. Other preferred embodiments of the modified NK cells express no or substantially no TRAIL receptors, or do so only at a low level—sufficiently low that viability of the modified NK cells is not adversely affected by expression of the mutant TRAIL.

In an optional embodiment, treatment of a cancer using modified NK cells expressing TRAIL or a TRAIL variant is enhanced by administering to a patient an agent capable of upregulating expression of TRAIL death receptors on cancer cells. This agent may be administered prior to, in combination with or subsequently to administration of the modified NK cells. It is preferable, however, that the agent is administered prior to administering the modified NK cells.

In a preferred embodiment the agent upregulates expression of DR5 on cancer cells. The agent may optionally be a chemotherapeutic medication, e.g. Bortezomib, and administered in a low dose capable of upregulating DR5 expression on the cancer.

The invention is not limited to any particular agents capable of upregulating DR5 expression, but examples of DR5-inducing agents include Bortezomib, Gefitinib, Piperlongumine, Doxorubicin, Alpha-tocopheryl succinate and HDAC inhibitors.

According to a preferred embodiment of the invention, the mutant/variant TRAIL ligand is linked to one or more NK cell costimulatory domains, e.g. 41BB/CD137, CD3zeta/CD247, DAP12 or DAP10. Binding of the variant to its receptor on a target cell thus promotes apoptotic signals within the target cell, as well as stimulating cytotoxic signals in the NK cell.

According to further preferred embodiments of the invention, NK cells are provided that both have reduced checkpoint inhibitory receptor function and also express a mutant TRAIL ligand, as described in more detail above in relation to these respective NK cell modifications. In even more preferred embodiments, a NK cell expressing a mutant TRAIL ligand that has reduced or no affinity for TRAIL decoy receptors and may be a derivative of KHYG-1, further lacks a gene encoding a checkpoint inhibitory receptor selected from CD96 (TACTILE), CD152 (CTLA4), CD223 (LAG-3), CD279 (PD-1), CD328 (SIGLEC7), SIGLEC9, TIGIT and TIM-3.

The present invention also provides NK cells and NK cell lines, preferably KHYG-1 cells and derivatives thereof, modified to express one or more CARs.

Suitably for cancer therapy uses, the CARs specifically bind to one or more ligands on cancer cells, e.g. CS1 (SLAMF7) on myeloma cells. For use in treating specific cancers, e.g. multiple myeloma, the CAR may bind CD38. For example, the CAR may include the binding properties of e.g. variable regions derived from, similar to, or identical with those from the known monoclonal antibody daratumumab. Such NK cells may be used in cancer therapy in combination with an agent that inhibits angiogenesis, e.g. lenalidomide. For use in therapy of cancers, especially leukemias and AML in particular, the CAR may bind to CLL-1.

The CAR-NKs may be bispecific, wherein their affinity is for two distinct ligands/antigens. Bispecific CAR-NKs can be used either for increasing the number of potential binding sites on cancer cells or, alternatively, for localizing cancer cells to other immune effector cells which express ligands specific to the NK-CAR. For use in cancer therapy, a bispecific CAR may bind to a target tumour cell and to an effector cell, e.g. a T cell, NK cell or macrophage. Thus, for example, in the case of multiple myeloma, a bispecific CAR may bind a T cell antigen (e.g. CD3, etc.) and a tumour cell marker (e.g. CD38, etc.). A bispecific CAR may alternatively bind to two separate tumour cell markers, increasing the overall binding affinity of the NK cell for the target tumour cell. This may reduce the risk of cancer cells developing resistance by downregulating one of the target antigens. An example in this case, in multiple myeloma, would be a CAR binding to both CD38 and CS-1/SLAMF7. Another tumour cell marker suitably targeted by the CAR is a "don't eat me" type marker on tumours, exemplified by CD47.

Optional features of the invention include providing further modifications to the NK cells and NK cell lines described above, wherein, for example, a Fc receptor (which can be CD16, CD32 or CD64, including subtypes and derivatives) is expressed on the surface of the cell. In use, these cells can show increased recognition of antibody-coated cancer cells and improve activation of the cytotoxic response.

Further optional features of the invention include adapting the modified NK cells and NK cell lines to better home to specific target regions of the body. NK cells of the invention may be targeted to specific cancer cell locations. In preferred embodiments for treatment of blood cancers, NK effectors of the invention are adapted to home to bone marrow. Specific NK cells are modified by fucosylation and/or sialylation to home to bone marrow. This may be achieved by genetically modifying the NK cells to express the appropriate fucosyl-transferase and/or sialyltransferase, respectively. Increased homing of NK effector cells to tumour sites may also be made possible by disruption of the tumour vasculature, e.g. by metronomic chemotherapy, or by using drugs targeting angiogenesis (Melero et al, 2014) to normalize NK cell infiltration via cancer blood vessels.

Yet another optional feature of the invention is to provide modified NK cells and NK cell lines with an increased intrinsic capacity for rapid growth and proliferation in culture. This can be achieved, for example, by transfecting the cells to overexpress growth-inducing cytokines IL-2 and IL-15. Moreover, this optional alteration provides a cost-effective alternative to replenishing the growth medium with cytokines on a continuous basis.

The invention further provides a method of making a modified NK cell or NK cell line, comprising genetically modifying the cell or cell line as described herein so as to increase its cytotoxicity. This genetic modification can be a stable knockout of a gene, e.g. by CRISPR, or a transient knockdown of a gene, e.g. by siRNA.

In a preferred embodiment, a stable genetic modification technique is used, e.g. CRISPR, in order to provide a new NK cell line with increased cytotoxicity, e.g. a derivative of KHYG-1 cells.

In embodiments, the method is for making a NK cell or NK cell line that has been modified so as to reduce inhibitory receptor function. Preferably, these inhibitory receptors are checkpoint inhibitory receptors.

More specific embodiments comprise a method for making a NK cell or NK cell line with reduced inhibitory receptor function, wherein the checkpoint inhibitory receptors are selected from CD96 (TACTILE), CD152 (CTLA4), CD223 (LAG-3), CD279 (PD-1), CD328 (SIGLEC7), SIGLEC9, TIGIT and TIM-3.

In preferred embodiments, the method comprises modifying the NK cells to reduce function of two or more of the inhibitory receptors.

The invention still further provides a method of making a modified NK cell or NK cell line comprising genetically modifying the cell or cell line to express TRAIL ligand or mutant TRAIL (variant) ligand.

In embodiments, the method comprises modifying a NK cell or NK cell line to express mutant TRAIL ligand that has an increased affinity for TRAIL receptors. Preferably, the TRAIL receptors are DR4 and/or DR5. Preferred embodiments provide a method of modifying the NK cells or NK cell lines to express a mutant TRAIL ligand that has a reduced affinity for decoy TRAIL receptors.

In further preferred embodiments, the method comprises modifying a NK cell or NK cell line to remove function of a checkpoint inhibitory receptor and also to express a mutant TRAIL ligand with reduced or no binding affinity for decoy TRAIL receptors.

Further typical embodiments provide a method for making a NK cell or NK cell line, in which function of one or more checkpoint inhibitory receptors has been removed and/or a mutant TRAIL ligand is expressed, which has reduced or no binding affinity for decoy TRAIL receptors, and the cell is further modified to express a CAR or bispecific CAR. The properties of the CAR are optionally as described above.

In embodiments, the method comprises making a NK cell or NK cell line, in which function of one or more checkpoint inhibitory receptors has been removed and/or a mutant TRAIL ligand is expressed, which has reduced or no binding affinity for decoy TRAIL receptors, and the cell is optionally modified to express a CAR or bispecific CAR, and the cell is further modified to express one or more Fc receptors. Suitable Fc receptors are selected from CD16 (FcRIII), CD32 (FcRII) and CD64 (FcRI).

Preferred embodiments of all the above comprise a method of making NK cells and NK cell lines being a derivative of KHYG-1.

As per the objects of the invention, the modified NK cell, NK cell line or composition thereof with increased cytotoxicity are for use in treating cancer in a patient, especially blood cancer.

In preferred embodiments, the modified NK cell, NK cell line or composition is for use in treating blood cancers including acute lymphocytic leukemia (ALL), acute myeloid leukemia (AML), chronic lymphocytic leukemia (CLL), chronic myeloid leukemia (CML), Hodgkin's lymphoma, non-Hodgkin's lymphoma, including T-cell lymphomas and B-cell lymphomas, asymptomatic myeloma, smoldering multiple myeloma (SMM), active myeloma or light chain myeloma.

In even more preferred embodiments, the invention is a NK cell line obtained as a derivative of KYHG-1 by reducing checkpoint inhibitory receptor function in a KHYG-1 cell or expressing a mutant TRAIL ligand in a KHYG-1 cell, or both, for use in treating blood cancer.

Modified NK cells, NK cell lines and compositions thereof described herein, above and below, are suitable for treatment of cancer, in particular cancer in humans, e.g. for treatment of cancers of blood cells or solid cancers. The NK cells and derivatives are preferably human NK cells. For human therapy, human NK cells are preferably used.

Various routes of administration will be known to the skilled person to deliver active agents and combinations thereof to a patient in need. Embodiments of the invention are for blood cancer treatment. Administration of the modified NK cells and/or NK cell lines can be systemic or localized, such as for example via the intraperitoneal route.

In other embodiments, active agent is administered more directly. Thus administration can be directly intratumoural, suitable especially for solid tumours.

NK cells in general are believed suitable for the methods, uses and compositions of the invention. As per cells used in certain examples herein, the NK cell can be a NK cell obtained from a cancer cell line. Advantageously, a NK cell, preferably treated to reduce its tumourigenicity, for example by rendering it mortal and/or incapable of dividing, can be obtained from a blood cancer cell line and used in methods of the invention to treat blood cancer.

To render a cancer-derived cell more acceptable for therapeutic use, it is generally treated or pre-treated in some way to reduce or remove its propensity to form tumours in the patient. Specific modified NK cell lines used in examples are safe because they have been rendered incapable of division; they are irradiated and retain their killing ability but die within about 3-4 days. Specific cells and cell lines are hence reduced of proliferation, e.g. as a result of irradiation. Treatments of potential NK cells for use in the methods herein include irradiation to prevent them from dividing and forming a tumour in vivo and genetic modification to reduce tumourigenicity, e.g. to insert a sequence encoding a suicide gene that can be activated to prevent the cells from dividing and forming a tumour in vivo. Suicide genes can be turned on by exogenous, e.g. circulating, agents that then cause cell death in those cells expressing the gene. A further alternative is the use of monoclonal antibodies targeting specific NK cells of the therapy. CD52, for example, is expressed on KHYG-1 cells and binding of monoclonal antibodies to this marker can result in antibody-dependent cell-mediated cytotoxicity (ADCC) and KHYG-1 cell death.

As discussed in an article published by Suck et al, 2006, cancer-derived NK cells and cell lines are easily irradiated using irradiators such as the Gammacell 3000 Elan. A source of Cesium-137 is used to control the dosing of radiation and a dose-response curve between, for example, 1 Gy and 50 Gy can be used to determine the optimal dose for eliminating the proliferative capacity of the cells, whilst maintaining the benefits of increased cytotoxicity. This is achieved by assaying the cells for cytotoxicity after each dose of radiation has been administered.

There are significant benefits of using an irradiated NK cell line for adoptive cellular immunotherapy over the well-established autologous or MHC-matched T cell approach. Firstly, the use of a NK cell line with a highly proliferative nature means expansion of modified NK cell lines can be achieved more easily and on a commercial level. Irradiation of the modified NK cell line can then be carried out prior to administration of the cells to the patient. These irradiated cells, which retain their useful cytotoxicity, have a limited life span and, unlike modified T cells, will not circulate for long periods of time causing persistent side-effects.

Additionally, the use of allogeneic modified NK cells and NK cell lines means that MHC class I expressing cells in the patient are unable to inhibit NK cytotoxic responses in the same way as they can to autologous NK cytotoxic responses. The use of allogeneic NK cells and cell lines for cancer cell killing benefits from the previously mentioned GVL effect and, unlike for T cells, allogeneic NK cells and cell lines do not stimulate the onset of GVHD, making them a much preferred option for the treatment of cancer via adoptive cellular immunotherapy.

As set out in the claims and elsewhere herein, the invention provides the following embodiments:

1. A natural killer (NK) cell or NK cell line that has been genetically modified to increase its cytotoxicity.

2. A NK cell or NK cell line according to embodiment 1, modified to have reduced function of one or more inhibitory receptors.

3. A NK cell or NK cell line according to embodiment 2, wherein the inhibitory receptors are checkpoint inhibitory receptors.

4. A NK cell or NK cell line according to embodiment 3, wherein the checkpoint inhibitory receptors are selected from CD96 (TACTILE), CD152 (CTLA4), CD223 (LAG-3), CD279 (PD-1), CD328 (SIGLEC7), SIGLEC9, TIGIT and TIM-3.

5. A NK cell or NK cell line according to any of embodiments 2 to 4, modified to have reduced function of two or more inhibitory receptors.

6. A NK cell or NK cell line according to any of embodiments 1 to 5, modified to express TRAIL ligand.

7. A NK cell or NK cell line according to embodiment 6, wherein the TRAIL ligand is a mutant TRAIL ligand.

8. A NK cell or NK cell line according to embodiment 7, wherein the mutant TRAIL ligand has an increased affinity for TRAIL receptors, e.g. DR4 and/or DR5.

9. A NK cell or NK cell line according to any of embodiments 7 to 8, wherein the mutant TRAIL ligand has reduced affinity for decoy TRAIL receptors.

10. A NK cell or NK cell line according to any preceding embodiment, modified to remove function of a checkpoint inhibitory receptor and also modified to express a mutant TRAIL ligand with reduced or no binding affinity for decoy TRAIL receptors.

11. A NK cell or NK cell line according to any preceding embodiment, expressing a chimeric antigen receptor (CAR).

12. A NK cell or NK cell line according to embodiment 11, wherein the CAR is a bispecific CAR.

13. A NK cell or NK cell line according to embodiment 12, wherein the bispecific CAR binds two ligands on one cell type.

14. A NK cell or NK cell line according to embodiment 12, wherein the bispecific CAR binds one ligand on each of two distinct cell types.

15. A NK cell or NK cell line according to embodiments 11 and 12, wherein the ligand(s) for the CAR or bispecific CAR are expressed on a cancer cell.

16. A NK cell or NK cell line according to embodiment 13, wherein the ligands for the bispecific CAR are both expressed on a cancer cell.

17. A NK cell or NK cell line according to embodiment 14, wherein the ligands for the bispecific CAR are expressed on a cancer cell and an immune effector cell.

18. A NK cell or NK cell line according to any preceding embodiment, modified to express one or more Fc receptors.

19. A NK cell or NK cell line according to embodiment 18, wherein the Fc receptors are selected from CD16 (FcRIII), CD32 (FcRII) and CD64 (FcRI).

20. A NK cell or NK cell line according to any preceding embodiment, wherein the cell line is a derivative of the KHYG-1 cell line.

21. A NK cell lacking a gene encoding a checkpoint inhibitory receptor selected from CD96 (TACTILE), CD152 (CTLA4), CD223 (LAG-3), CD279 (PD-1), CD328 (SIGLEC7), SIGLEC9, TIGIT and TIM-3.

22. A NK cell according to embodiment 21, lacking genes encoding two or more checkpoint inhibitory receptors selected from CD96 (TACTILE), CD152 (CTLA4), CD223 (LAG-3), CD279 (PD-1), CD328 (SIGLEC7), SIGLEC9, TIGIT and TIM-3.

23. A NK cell according to embodiment 21 or 22, wherein the checkpoint inhibitory receptor is selected from CD96 (TACTILE), CD152 (CTLA4) and CD279 (PD-1).

24. A NK cell according to any of embodiments 21 to 23, being a derivative of KHYG-1.

25. A NK cell expressing a mutant TRAIL ligand that has reduced or no affinity for TRAIL decoy receptors.

26. A NK cell according to embodiment 25, being a derivative of KHYG-1.

27. A NK cell according to embodiment 25 or 26, lacking a gene encoding a checkpoint inhibitory receptor selected from CD96 (TACTILE), CD152 (CTLA4), CD223 (LAG-3), CD279 (PD-1), CD328 (SIGLEC7), SIGLEC9, TIGIT and TIM-3.

28. A NK cell or cell line according to any preceding embodiment, incapable of proliferation, e.g. as a result of irradiation.

29. A method of making a modified NK cell or NK cell line, comprising genetically modifying the cell or cell line so as to increase its cytotoxicity.

30. A method according to embodiment 29, wherein the NK cell or NK cell line is modified so as to reduce inhibitory receptor function.

31. A method according to embodiment 30, wherein the inhibitory receptors are checkpoint inhibitory receptors.

32. A method according to embodiment 31, wherein the checkpoint inhibitory receptors are selected from CD96 (TACTILE), CD152 (CTLA4), CD223 (LAG-3), CD279 (PD-1), CD328 (SIGLEC7), SIGLEC9, TIGIT and TIM-3.

33. A method according to any of embodiments 29 to 32, comprising modifying the NK cells to reduce function of two or more of the inhibitory receptors.

34. A method according to any of embodiments 29 to 33, comprising modifying the NK cell or NK cell line to express TRAIL ligand or mutant TRAIL ligand.

35. A method according to embodiment 34, wherein the mutant TRAIL ligand has an increased affinity for TRAIL receptors.

36. A method according to embodiment 35, wherein the TRAIL receptors are DR4 and/or DR5.

37. A method according to any of embodiments 34 to 36, wherein the mutant TRAIL ligand has a reduced affinity for decoy TRAIL receptors.

38. A method according to any of embodiments 29 to 37, wherein the NK cell or NK cell line is modified to remove function of a checkpoint inhibitory receptor and also modified to express a mutant TRAIL ligand with reduced or no binding affinity for decoy TRAIL receptors.

39. A method according to embodiment 38, wherein the NK cell or NK cell line is modified to express a CAR or bispecific CAR.

40. A method according to embodiment 39, wherein the bispecific CAR binds two ligands on one cell type.

41. A method according to embodiment 39, wherein the bispecific CAR binds one ligand on each of two distinct cell types.

42. A method according to embodiment 39, wherein the ligand(s) for the CAR or bispecific CAR are expressed on a cancer cell.

43. A method according to embodiment 40, wherein the ligands for the bispecific CAR are both expressed on a cancer cell.

44. A method according to embodiment 41, wherein the ligands for the bispecific CAR are expressed on a cancer cell and an immune effector cell.

45. A method according to any of embodiments 29 to 44, wherein the NK cell or NK cell line is modified to express one or more Fc receptors.

46. A method according to embodiment 45, wherein the Fc receptors are selected from CD16 (FcRIII), CD32 (FcRII) and CD64 (FcRI).

47. A method according to any of embodiments 29 to 46, wherein the cell line is a derivative of the KHYG-1 cell line.

48. A NK cell or NK cell line obtained by a method according to any of embodiments 29 to 47.

49. A KHYG-1 derivative obtained by a method according to any of embodiments 29 to 48.

50. A modified NK cell, NK cell line or composition thereof with increased cytotoxicity for use in treating cancer in a patient.

51. A NK cell or NK cell line according to any of embodiments 1 to 28, or obtained according to any of embodiments 29 to 49, for use according to embodiment 50.

52. A modified NK cell, NK cell line or composition for use according to embodiment 50 or 51, wherein the cancer is a blood cancer.

53. A modified NK cell, NK cell line or composition for use according to embodiment 52, wherein the blood cancer is acute lymphocytic leukemia (ALL), acute myeloid leukemia (AML), chronic lymphocytic leukemia (CLL), chronic myeloid leukemia (CML), Hodgkin's lymphoma, non-Hodgkin's lymphoma, including T-cell lymphomas and B-cell lymphomas, asymptomatic myeloma, smoldering multiple myeloma (SMM), active myeloma or light chain myeloma.

54. A NK cell line obtained as a derivative of KYHG-1 by reducing checkpoint inhibitory receptor function in a KHYG-1 cell or expressing a mutant TRAIL ligand in a KHYG-1 cell, or both, for use in treating blood cancer.

EXAMPLES

The present invention is now described in more and specific details in relation to the production of NK cell line KHYG-1 derivatives, modified to exhibit more cytotoxic activity and hence ability to cause leukemia cell death in humans.

The invention is now illustrated in specific embodiments with reference to the accompanying drawings in which.

DNA, RNA and amino acid sequences are referred to below, in which:

SEQ ID NO: 1 is the full LIR2 DNA sequence;
SEQ ID NO: 2 is the LIR2 amino acid sequence;
SEQ ID NO: 3 is the LIR2 g9 gRNA sequence;
SEQ ID NO: 4 is the LIR2 g18 gRNA sequence;
SEQ ID NO: 5 is the LIR2 forward primer sequence;
SEQ ID NO: 6 is the LIR2 reverse primer sequence;
SEQ ID NO: 7 is the full CTLA4 DNA sequence;
SEQ ID NO: 8 is the CTLA4 amino acid sequence;
SEQ ID NO: 9 is the CTLA4 g7 gRNA sequence;
SEQ ID NO: 10 is the CTLA4 g15 gRNA sequence;
SEQ ID NO: 11 is the CTLA4 forward primer sequence;
SEQ ID NO: 12 is the CTLA4 reverse primer sequence;
SEQ ID NO: 13 is the wildtype TRAIL DNA sequence; and
SEQ ID NO: 14 is the 4C9 mutant TRAIL DNA sequence.

Example 1—Knockout of Inhibitory Receptor Function

CRISPR/Cas9

Cells were prepared as follows, having inhibitory receptor function removed. gRNA constructs were designed and prepared to target genes encoding the 'classical' inhibitory receptor LIR2 and the 'checkpoint' inhibitory receptor CTLA4 in the human genome of NK cells. CRISPR/Cas9 genome editing was then used to knock out the LIR2 and CTLA4 target genes.

Figure 1:
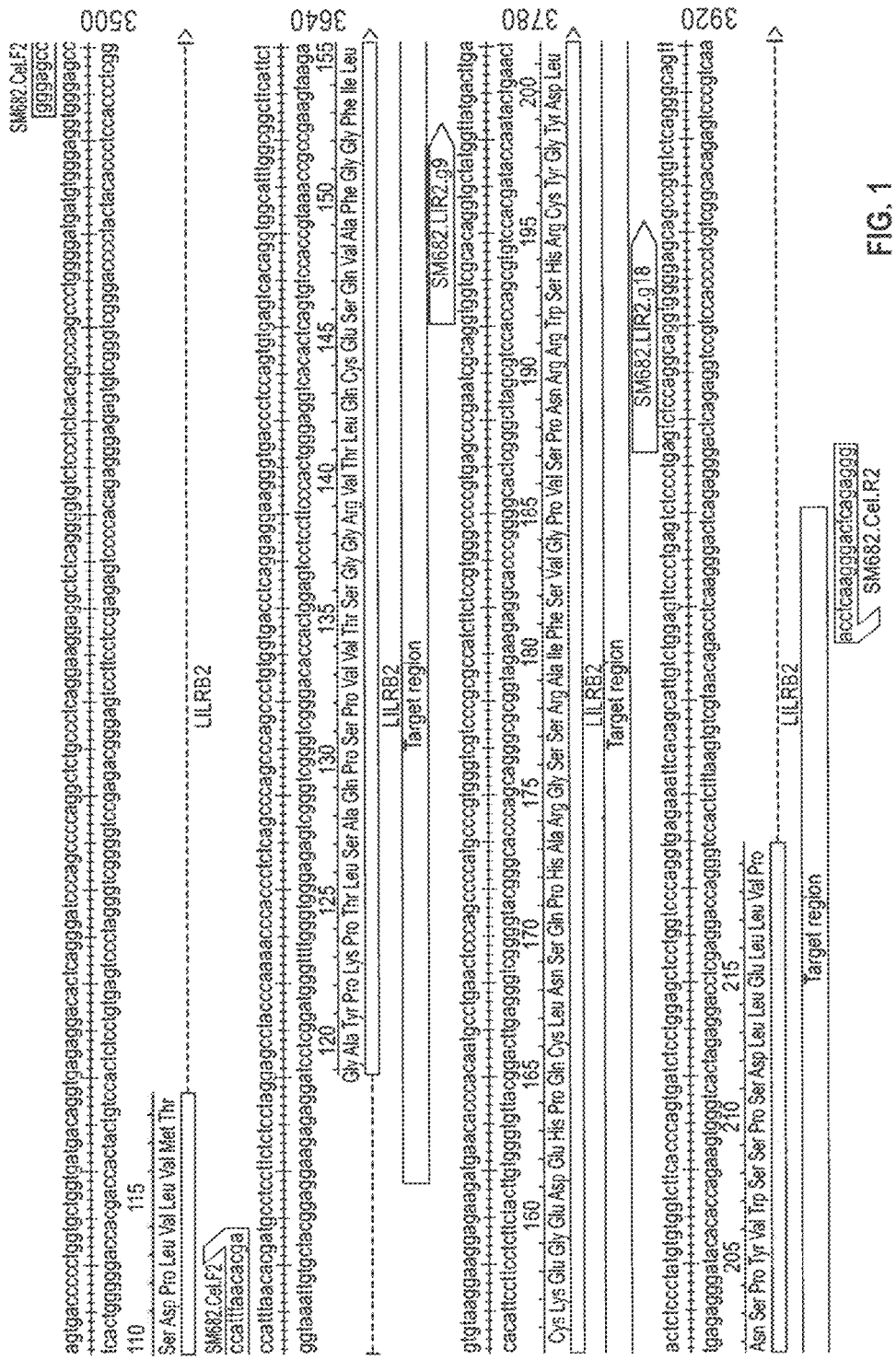
FIG. 1 shows the DNA sequence of the LIR2 gene target region and marks the gRNA flanking regions.
Figure 2:
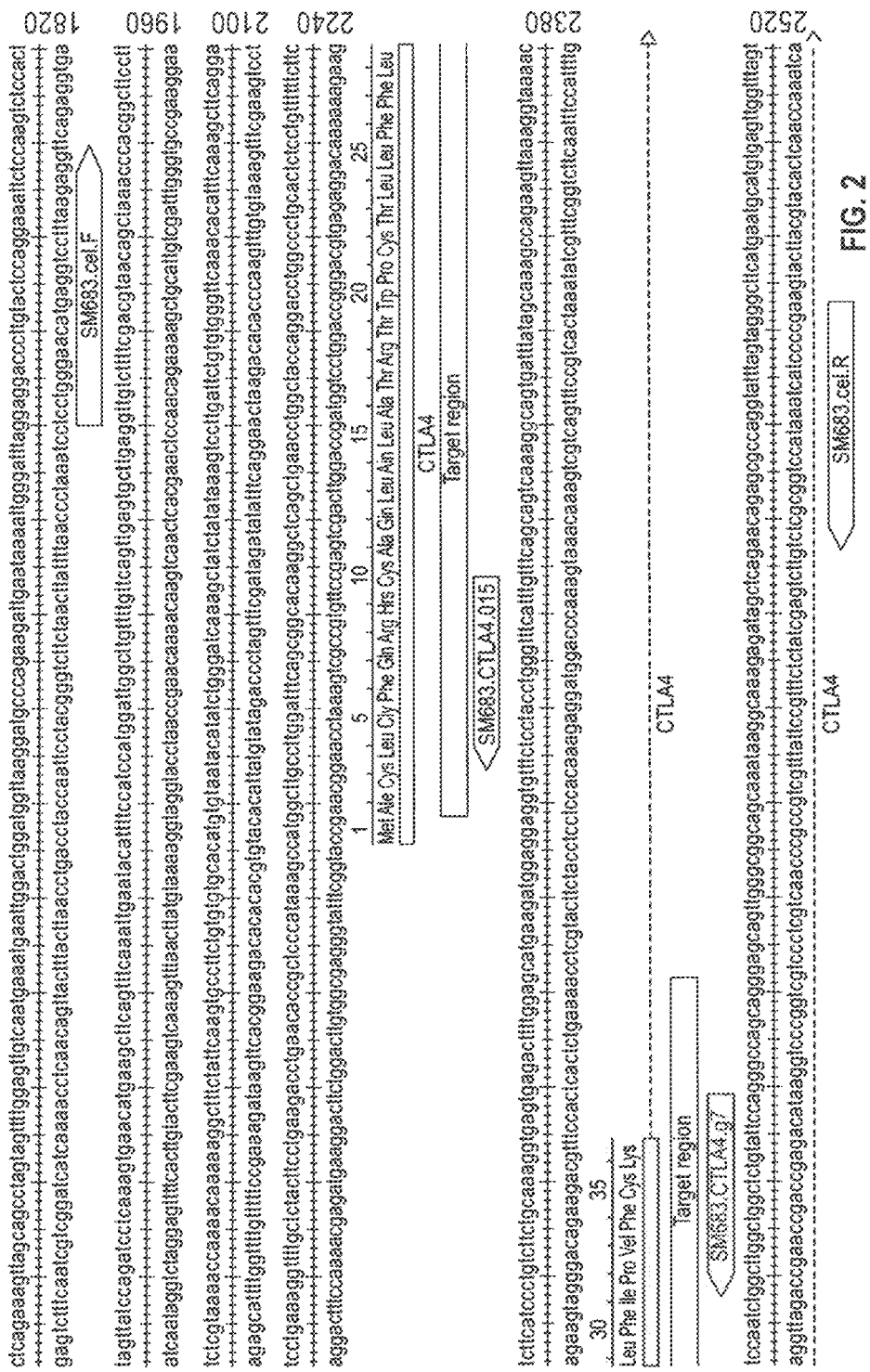
FIG. 2 shows the DNA sequence of the CTLA4 gene target region and marks the gRNA flanking regions.

Two gRNA candidates were selected for each target gene and their cleavage efficacies in K562 cells determined. The sequences of the gRNA candidates are shown in Table 1 and the Protospacer Adjacent Motif (PAM) relates to the last 3 bases of the sequence. The flanking regions of the gRNA sequences on the LIR2 gene (SEQ ID NO: 1) and the CTLA4 gene (SEQ ID NO: 7) are shown in FIGS. 1 and 2, respectively.

TABLE 1 gRNA candidates and sequences

| Gene | Plasmid Name | Sequence |
| --- | --- | --- |
| hLIR2 | SM682.LIR2.g9 | GAGTCACAGGTGGCATTTGGCGG (SEQ ID NO: 3) |
| | SM682.LIR2.g18 | CGAATCGCAGGTGGTCGCACAGG (SEQ ID NO: 4) |
| hCTLA4 | SM683.CTLA4.g7 | CACTCACCTTTGCAGAAGACAGG (SEQ ID NO: 9) |
| | SM683.CTLA4.g15 | CCTTGTGCCGCTGAAATCCAAGG (SEQ ID NO: 10) |

Figure 3:
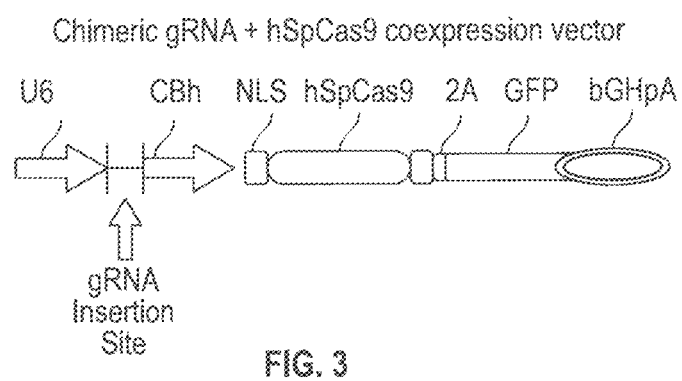
FIG. 3 shows the gRNA construct (expression vector) used for transfection.

K562 cells were transfected with the prepared gRNA constructs (FIG. 3) and subsequently harvested for PCR amplification. The presence of GFP expression was used to report successful incorporation of the gRNA construct into the K562 cells. This confirmed expression of the Cas9 gene and therefore the ability to knock out expression of the LIR2 and CTLA4 genes.

The cleavage activity of the gRNA constructs was determined using an in vitro mismatch detection assay. T7E1 endonuclease I recognises and cleaves non-perfectly matched DNA, allowing the parental LIR2 and CTLA4 genes to be compared to the mutated genes following CRISPR/Cas9 transfection and non-homologous end joining (NHEJ).

Figure 4:
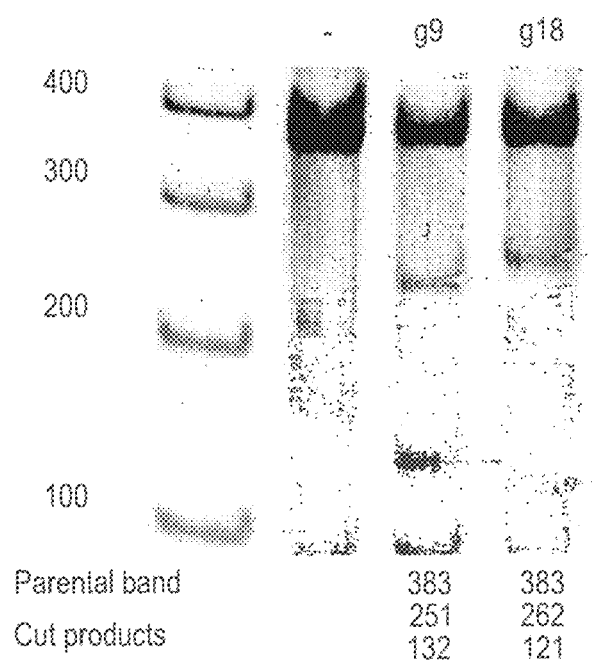
FIG. 4 shows gel electrophoresis bands for parental and mutated LIR2 DNA, before and after transfection.

FIG. 4 shows the resulting bands following agarose gel electrophoresis after knockout of the LIR2 gene with the g9 and g18 gRNA sequences. The three bands corresponding to each mutation relate to the parental gene and the two resulting strands following detection of a mismatch in the DNA sequence after transfection. The g9 gRNA sequence resulted in an 11% success rate of transfection, whereas the g18 gRNA resulted in 10%.

Figure 5:
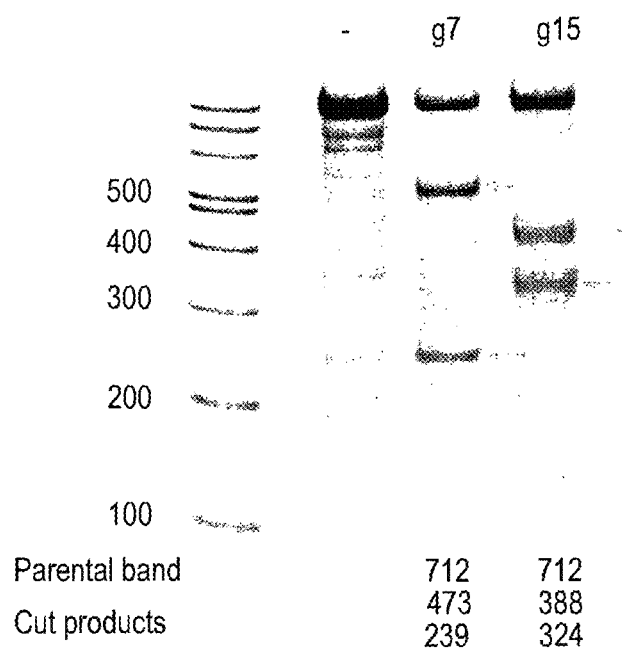
FIG. 5 shows gel electrophoresis bands for parental and mutated CTLA4 DNA, before and after transfection.

FIG. 5 shows the resulting bands following agarose gel electrophoresis after knockout of the CTLA4 gene with the g7 and g15 gRNA sequences. The g7 gRNA sequence resulted in a 32% success rate of transfection, whereas the g15 gRNA resulted in 26%.

Following the successful knockout of LIR2 and CTLA4 in K562 cells, KHYG-1 cells were transfected with gRNA constructs.

KHYG-1 derivative clones having homozygous deletions were selected. A Cas9/puromycin acetyltransferase (PAC) expression vector was used for this purpose. Successfully transfected cells were selected, based on their resistance to the antibiotic puromycin.

Cas9 RNP

Another protocol used for knockout of checkpoint inhibitory receptors in NK cells was that of Cas9 RNP transfection. An advantage of using this protocol was that similar transfection efficiencies were achievable but with significantly lower toxicity compared to using the DNA plasmids of the CRISPR/Cas9 protocol.

$1\times10^6$ KHYG1 cells were harvested for each transfection experiment. The cells were washed with PBS and spun down in a centrifuge. The supernatant was then discarded. The CRISPR RNP (RNA binding protein) materials were then prepared as follows:

(1) a 20 μM solution of the required synthesized crRNA and tRNA (purchased from Dharmacon) was prepared.

(2) 4 μl of crRNA (20 μM) and 4 μl of tRNA (20 μM) were mixed together.

(3) The mixture was then added to 2 μl Cas9 protein (5 μg/μl).

(4) All of the components were mixed and incubated at room temperature for 10 minutes.

Following the Neon® Transfection System, the cells were mixed with Cas9 RNP and electroporation was performed using the following parameters:

Voltage: 1450v
Pulse width: 30 ms
Pulse number: 1

The cells were then transferred to one well of a 12-well plate containing growth medium (inc. IL-2 and IL-15).

The cells were harvested after 48-72 hours to confirm gene editing efficiency by T7 endonuclease assay and/or Sanger sequencing. The presence of indels were confirmed, indicating successful knockout of CTLA4, PD1 and CD96 in KHYG1 cells.

Site-Specific Nucleases

Another protocol used for knockout of checkpoint inhibitory receptors in NK cells was that of XTN TALEN transfection. An advantage of using this protocol was that a particularly high level of specificity was achievable compared to wildtype CRISPR.

Step 1: Preparation of Reagents

KHYG-1 cells were assayed for certain attributes including transfection efficiency, single cell cloning efficiency and karyotype/copy number. The cells were then cultured in accordance with the supplier's recommendations.

Depending on the checkpoint inhibitory receptor being knockout out, nucleases were prepared by custom-design of at least 2 pairs of XTN TALENs. The step of custom-design includes evaluation of gene locus, copy number and functional assessment (i.e. homologs, off-target evaluation).

Step 2: Cell Line Engineering

The cells were transfected with the nucleases of Step 1; this step was repeated up to 3 times in order to obtain high levels of cutting and cultures were split and intermediate cultures maintained prior to each transfection.

Initial screening occurred several days after each transfection; the pools of cells were tested for cutting efficiency via the Cel-1 assay. Following the level of cutting reaching acceptable levels or plateaus after repeated transfections, the cells were deemed ready for single cell cloning.

The pooled cells were sorted to one cell per well in a 96-well plate; the number of plates for each pool was dependent on the single cell cloning efficiency determined in Step 1. Plates were left to incubate for 3-4 weeks.

Step 3—Screening and Expansion

Once the cells were confluent in the 96-well plates, cultures were consolidated and split into triplicate 96-well plates; one plate was frozen as a backup, one plate was re-plated to continue the expansion of the clones and the final plate was used for genotype confirmation.

Each clone in the genotype plate was analyzed for loss of qPCR signal, indicating all alleles had been modified. Negative clones were PCR amplified and cloned to determine the nature of the indels and lack of any wildtype or in-frame indels.

Clones with the confirmed knockout were consolidated into no more than one 24-well plate and further expanded; typically 5-10 frozen cryovials containing $1\times10^6$ cells per vial for up to 5 individual clones were produced per knockout.

Step 4—Validation

Cells were banked under aseptic conditions.

Basic release criteria for all banked cells included viable cell number (pre-freeze and post-thaw), confirmation of identity via STR, basic sterility assurance and mycoplasma testing; other release criteria were applied when necessary (karyotype, surface marker expression, high level sterility, knockout evaluation of transcript or protein, etc).

Example 2—Knockdown of Checkpoint Inhibitory Receptor CD96 Function Via RNAi siRNA knockdown of CD96 in KHYG-1 cells was performed by electroporation. The Nucleofection Kit T was used, in conjunction with the Amaxa Nucleofector II, from Lonza, as it is appropriate for use with cell lines and can successfully transfect both dividing and non-dividing cells and achieves transfection efficiencies of up to 90%.

Control siRNA (catalog number: sc-37007) and CD96 siRNA (catalog number: sc-45460) were obtained from Santa Cruz Biotechnology. Antibiotic-free RPMI-1640 containing 10% FBS, 2 mM L-glutamine was used for post-Nucleofection culture. Mouse anti-human CD96-APC (catalog number: 338409) was obtained from Biolegend for staining.

A 20 μM of siRNA stock solution was prepared. The lyophilized siRNA duplex was resuspended in 33 μl of the RNAse-free water (siRNA dilution buffer: sc-29527) to FITC-control/control-siRNA, in 165 μl of the RNAse-free water for the target gene siRNA (siRNA CD96). The tube was heated to 90° C. for 1 minute and then incubated at 37° C. for 60 minutes. The siRNA stock was then stored at −20° C. until needed.

The KHYG-1 cells were passaged one to two days before Nucleofection, as the cells must be in logarithmic growth phase.

The Nucleofector solution was warmed to room temperature (100 ul per sample). An aliquot of culture medium containing serum and supplements was also pre-warmed at 37° C. in a 50 ml tube. 6-well plates were prepared by adding 1.5 ml of culture medium containing serum and supplements. The plates were pre-incubated in a humidified 37° C./5% $CO_2$ incubator.

$2 \times 10^6$ cells in 100 µl Nucleofection solution was mixed gently with 4 µl 20 µM siRNA solution (1.5 µg siRNA). Air bubbles were avoided during mixing. The mixture was transferred into Amaxa certified cuvettes and placed into the Nucleofector cuvette holder and program U-001 selected.

The program was allowed to finish, and the samples in the cuvettes were removed immediately. 500 µl pre-equilibrated culture medium was then added to each cuvette. The sample in each cuvette was then gently transferred to a corresponding well of the prepared 6-well plate, in order to establish a final volume of 2 ml per well.

Figure 6A:
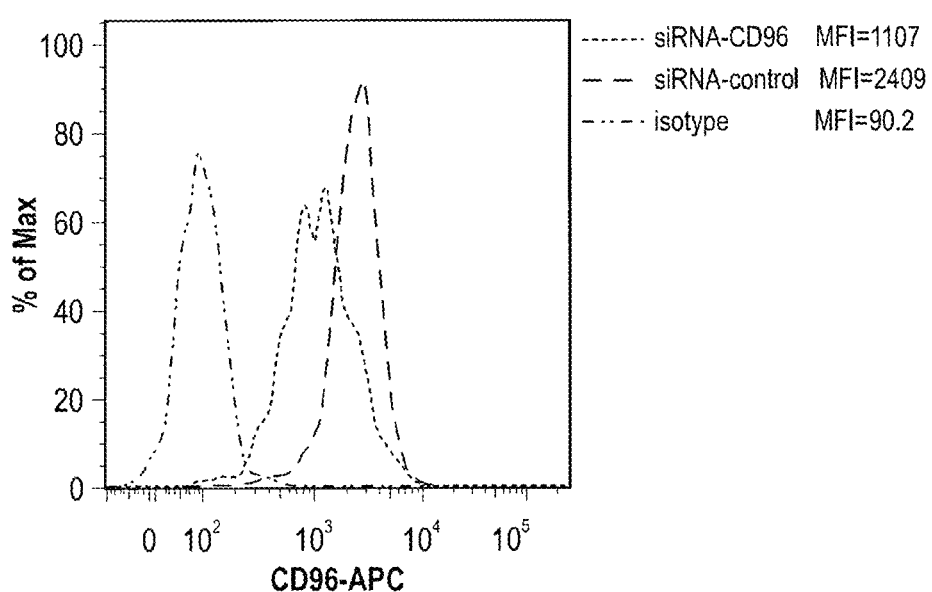
FIG. 6A is a FACS plot showing successful CD96 knockdown using electroporation.
Figure 6B:
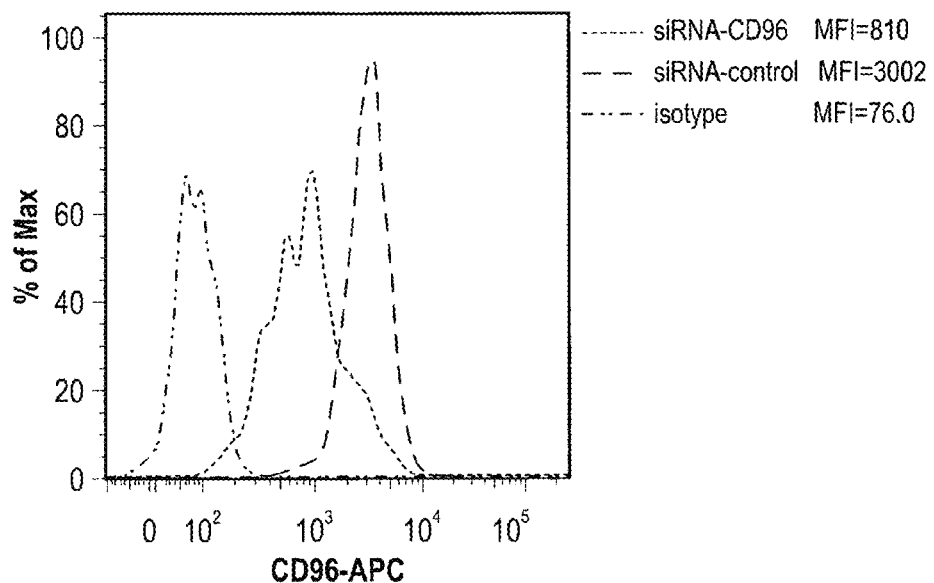
FIG. 6B is a FACS plot showing successful CD96 knockdown using electroporation.

The cells were then incubated in a humidified 37° C./5% $CO_2$ incubator until transfection analysis was performed. Flow cytometry analysis was performed 16-24 hours after electroporation, in order to measure CD96 expression levels. This electroporation protocol was carried out multiple times and found to reliably result in CD96 knockdown in KHYG-1 cells (see e.g. FIGS. 6A and 6B).

Example 3—Enhanced Cytotoxicity of NK Cells with a CD96 Knockdown

KHYG-1 cells with and without the CD96 knockdown were co-cultured with K562 cells at different effector:target (E:T) ratios.

Cytotoxicity was measured 4 hours after co-culture, using the DELFIA EuTDA Cytotoxicity Kit from PerkinElmer (Catalog number: AD0116).

Target cells K562 were cultivated in RPMI-1640 medium containing 10% FBS, 2 mM L-glutamine and antibiotics. 96-well V-bottom plates (catalog number: 83.3926) were bought from SARSTEDT. An Eppendorf centrifuge 5810R (with plate rotor) was used to spin down the plate. A VARIOSKAN FLASH (with Scanit software 2.4.3) was used to measure the fluorescence signal produced by lysed K562 cells.

K562 cells were washed with culture medium and the number of cells adjusted to $1 \times 10^6$ cells/mL with culture medium. 2-4 mL of cells were added to 5 µl of BATDA reagent and incubated for 10 minutes at 37° C. Within the cell, the ester bonds are hydrolysed to form a hydrophilic ligand, which no longer passes through the membrane. The cells were centrifuged at 1500 RPM for 5 mins to wash the loaded K562 cells. This was repeated 3-5 times with medium containing 1 mM Probenecid (Sigma P8761). After the final wash the cell pellet was resuspended in culture medium and adjusted to about $5 \times 10^4$ cells/mL.

Wells were set up for detection of background, spontaneous release and maximum release. 100 µL of loaded target cells (5,000 cells) were transferred to wells in a V-bottom plate and 100 µL of effector cells (KHYG-1 cells) were added at varying cell concentrations, in order to produce effector to target ratios ranging from 1:1 to 20:1. The plate was centrifuged at 100×g for 1 minute and incubated for 4 hours in a humidified 5% $CO_2$ atmosphere at 37° C. For maximum release wells 10 µL of lysis buffer was added to each well 15 minutes before harvesting the medium. The plate was centrifuged at 500×g for 5 minutes.

20 µL of supernatant was transferred to a flat-bottom 96 well plate 200 µL of pre-warmed Europium solution added. This was incubated at room temperature for 15 mins using a plate shaker. As K562 cells are lysed by the KHYG-1 cells, they release ligand into the medium. This ligand then reacts with the Europium solution to form a fluorescent chelate that directly correlates with the amount of lysed cells.

The fluorescence was then measured in a time-resolved fluorometer by using VARIOSKAN FLASH. The specific release was calculated using the following formula:

% specific release=Experiment release−Spontaneous release/Maximum release−Spontaneous release Statistical analysis was performed using Graphpad Prism 6.04 software. A paired t test was used to compare the difference between siRNA CD96 knockdown KHYG-1 cells and control groups (n=3).

Figure 7:
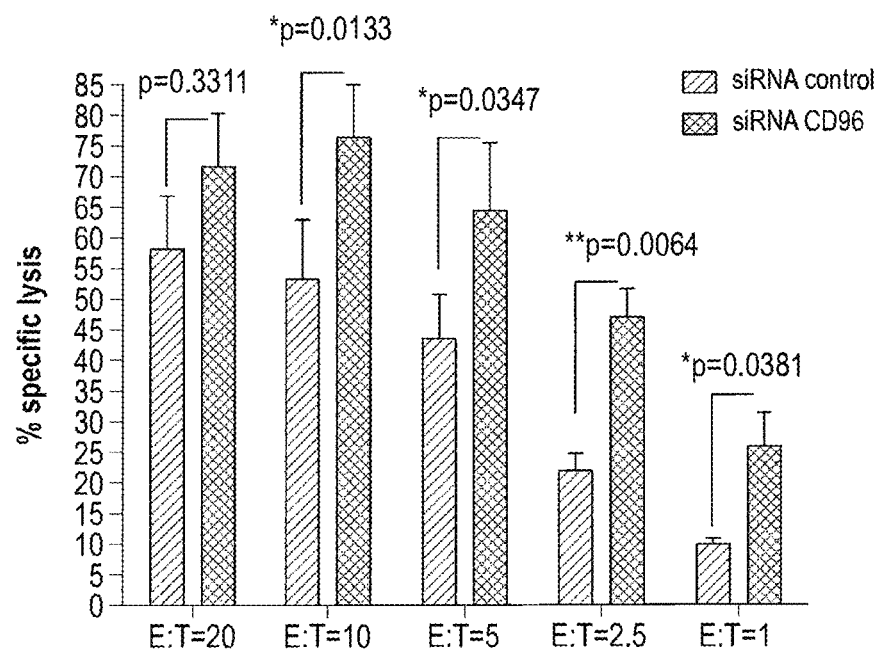
FIG. 7 is a bar chart showing increased cytotoxicity of CD96 knockdown KHYG-1 cells against K562 cells at various E:T ratios.

The specific release was found to be significantly increased in co-cultures containing the CD96 knockdown KHYG-1 cells. This was the case at all E:T ratios (see FIG. 7).

As fluorescence directly correlates with cell lysis, it was confirmed that knocking down CD96 expression in KHYG-1 cells resulted in an increase in their ability to kill K562 cancer target cells.

Example 4—Enhanced Cytotoxicity of NK Cells with a CD328 (Siglec-7) Knockdown

SiRNA-Mediated Knock-Down of CD328 in NK-92 Cells
Materials, Reagents and Instruments Control siRNA (catalog number: sc-37007) and CD328 siRNA (catalog number: sc-106757) were bought from Santa Cruz Biotechnology. To achieve transfection efficiencies of up to 90% with high cell viability (>75%) in NK-92 cells with the Nucleofector™ Device (Nucleofector II, Lonza), a Nucleofector™ Kit T from Lonza was used. RPMI-1640 containing 10% FBS, 2 mM L-glutamine, antibiotics free, was used for post-Nucleofection culture. Mouse anti-human CD328-APC (catalog number: 339206) was bought from Biolegend.

Protocol
    To make 10 µM of siRNA stock solution
    Resuspend lyophilized siRNA duplex in 66 µl of the RNAse-free water (siRNA dilution buffer: sc-29527) to FITC-control/control-siRNA, in 330 µl of the RNAse-free water for the target gene siRNA (siRNA CD328).
    Heat the tube to 90° C. for 1 minute.
    Incubate at 37° C. for 60 minutes.
    Store siRNA stock at −20° C. if not used directly.
    One Nucleofection sample contains (for 100 µl standard cuvette)
    Cell number: $2 \times 10^6$ cells
    siRNA: 4 µl of 10 µM stock
    Nucleofector solution: 100 µl Nucleofection
    Cultivate the required number of cells. (Passage one or two day before Nucleofection, cells must be in logarithmic growth phase).
    Prepare siRNA for each sample.
    Pre-warm the Nucleofector solution to room temperature (100 µl per sample).
    Pre-warm an aliquot of culture medium containing serum and supplements at 37° C. in a 50 ml tube. Prepare 6-well plates by filling with 1.5 ml of cullture medium containing serum and supplements and pre-incubate plates in a humidified 37° C./5% CO2 incubator.
    Take an aliquot of cell culture and count the cells to determine the cell density.

Centrifuge the required number of cells at 1500 rpm for 5 min. Discard supernatant completely so that no residual medium covers the cell pellet.

Resuspend the cell pellet in room temperature Nucleofector Solution to a final concentration of $2\times10^6$ cells/100 µl. Avoid storing the cell suspension longer than 15-20 min in Nucleofector Solution, as this reduces cell viability and gene transfer efficiency.

Mix 100 µl of cell suspension with siRNA.

Transfer the sample into an amaxa certified cuvette. Make sure that the sample covers the bottom of the cuvette, avoid air bubbles while pipetting. Close the cuvette with the blue cap.

Select the appropriate Nucleofector program (A-024 for NK-92 cells). Insert the cuvette into the cuvette holder (Nucleofector II: rotate the carousel clockwise to the final position) and press the "x" button to start the program.

To avoid damage to the cells, remove the samples from the cuvette immediately after the program has finished (display showing "OK"). Add 500 µl of the pre-warmed culture medium into the cuvette and transfer the sample into the prepared 6-well plate.

Incubate cells in a humidified 37° C./5% $CO_2$ incubator. Perform flow cytometric analysis and cytotoxicity assay after 16-24 hours.

Figure 8:
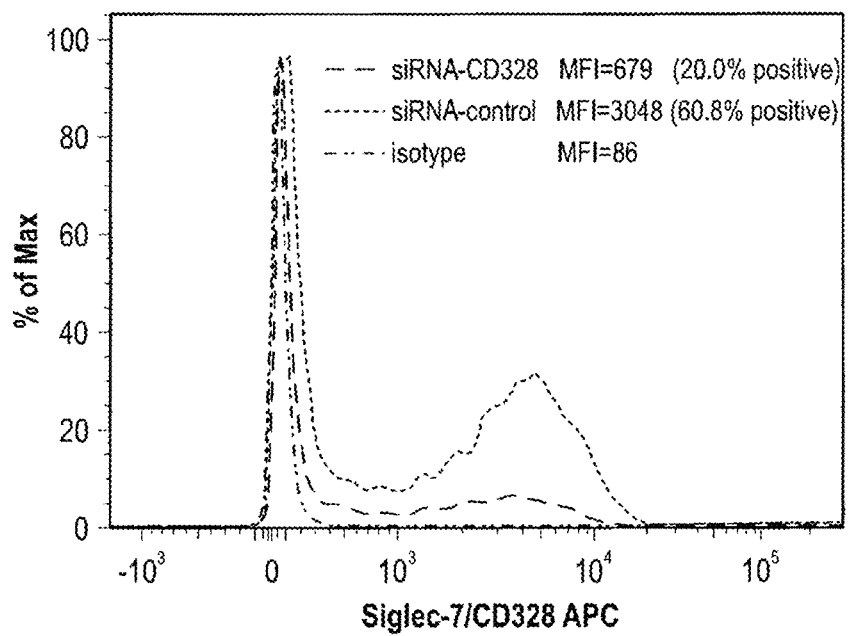
FIG. 8 shows knockdown of CD328 (Siglec-7) in NK-92 cells.

Results: we followed the above protocol and performed flow cytometry analysis of CD328 expression level in NK-92 cells. The results of one representative experiment is shown in FIG. 8, confirming successful knockdown.

Knocking Down CD328 Enhances Cytotoxicity

Materials, Reagents and Instruments

DELFIA EuTDA cytotoxicity kit based on fluorescence enhancing ligand (Catalog number: AD0116) was bought from PerkinElmer. Target cells K562 were cultivated in RPMI-1640 medium containing 10% FBS, 2 mM L-glutamine and antibiotics. 96-well V-bottom plates (catalog number: 83.3926) were bought from SARSTEDT. Eppendrof centrifuge 5810R (with plate rotor) was used to spin down the plate. VARIOSKAN FLASH (with Scanit software 2.4.3) was used to measure the fluorescence signal produced by lysed K562 cells.

Protocol

Load target K562 cells with the fluorescence enhancing ligand DELFIA BATDA reagent Wash K562 cells with medium, adjust the number of cells to $1\times10^6$ cells/mL with culture medium. Add 2-4 mL of cells to 5 µl of BATDA reagent, incubate for 10 minutes at 37° C.

Spin down at 1500 RPM for 5 minutes to wash the loaded K562 cells for 3-5 times with medium containing 1 mM Probenecid (Sigma P8761).

After the final wash resuspend the cell pellet in culture medium and adjust to about $5\times10^4$ cells/m L.

Cytotoxicity Assay

Set up wells for detection of background, spontaneously release and maximum release.

Pipette 100 µL of loaded target cells (5,000 cells) to a V-bottom plate.

Add 100 µL of effector cells (NK-92) of varying cell concentrations. Effector to target ratio ranges from 1:1 to 20:1.

Spin down the plate at 100×g of RCF for 1 minute.

Incubate for 2 hours in a humidified 5% CO2 atmosphere at 37° C. For maximum release wells, add 10 µL of lysis buffer to each well 15 minutes before harvesting the medium.

Spin down the plate at 500×g for 5 minutes.

Transfer 20 µL of supernatant to a flat-bottom 96 well plate, add 200 µL of pre-warmed Europium solution, incubate at room temperature for 15 minutes using plateshaker.

Figure 9:
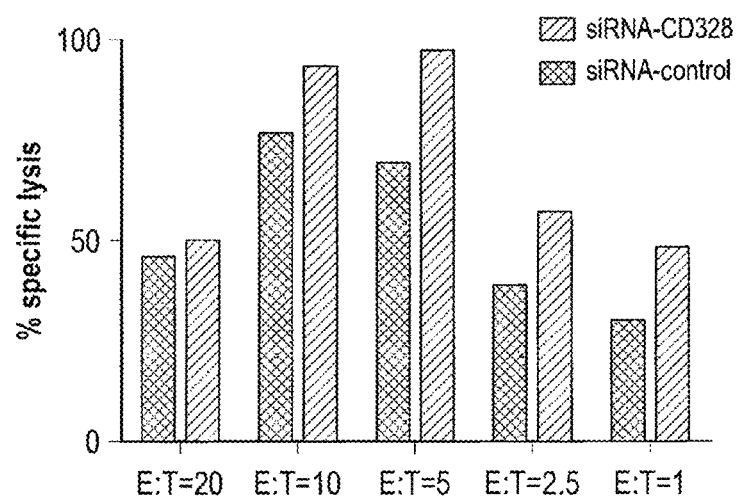
FIG. 9 shows enhanced cytotoxicity of NK Cells with the CD328 (Siglec-7) knockdown.

Measure the fluorescence in a time-resolved fluorometer by using VARIOSKAN FLASH. The specific release was calculated using the following formula:

% specific release=Experiment release−Spontaneous release/Maximum release−Spontaneous release Results: we followed the above to determine the effect on cytotoxicity of the CD328 knockdown. The results of one representative experiment are shown in FIG. 9. As seen, cytotoxicity against target cells was increased in cells with the CD328 knockdown.

Example 5—Protocol for Blood Cancer Therapy by Knockdown/Knockout of Checkpoint Inhibitory Receptors As demonstrated in the above Examples, checkpoint inhibitory receptor function can be knocked down or knocked out in a variety of ways. The following protocol was developed for use in treating patients with blood cancer:

Following diagnosis of a patient with a cancer suitably treated with the invention, an aliquot of modified NK cells can be thawed and cultured prior to administration to the patient.

Alternatively, a transient mutation can be prepared using e.g. siRNA within a day or two, as described above. The MaxCyte Flow Electroporation platform offers a suitable solution for achieving fast large-scale transfections in the clinic.

The removal of certain checkpoint inhibitory receptors may be more beneficial than others. This is likely to depend on the patient and the cancer. For this reason, the cancer is optionally biopsied and the cancer cells are grown in culture ex vivo. A range of NK cells with different checkpoint inhibitory receptor modifications can thus be tested for cytotoxicity against the specific cancer. This step can be used to select the most appropriate NK cell or derivative thereof for therapy.

Following successful modification, the cells are resuspended in a suitable carrier (e.g. saline) for intravenous and/or intratumoural injection into the patient.

Example 6—KHYG-1 Knock-in of TRAIL/TRAIL Variant

KHYG-1 cells were transfected with both TRAIL and TRAIL variant, in order to assess their viability and ability to kill cancer cells following transfection.

The TRAIL variant used is that described in WO 2009/077857. It is encoded by the wildtype TRAIL gene containing the D269H/E195R mutation. This mutation significantly increases the affinity of the TRAIL variant for DR5, whilst reducing the affinity for both decoy receptors (DcR1 and DcR2).

Baseline TRAIL Expression

Baseline TRAIL (CD253) expression in KHYG-1 cells was assayed using flow cytometry.

Mouse anti-human CD253-APC (Biolegend catalog number: 308210) and isotype control (Biolegend catalog number: 400122) were used to stain cell samples and were analyzed on a BD FACS Canto II flow cytometer.

KHYG-1 cells were cultured in RPMI 1640 medium containing 10% FBS, 2 mM L-glutamine, penicillin (100 U/mL)/streptomycin (100 mg/mL) and IL-2 (10 ng/mL). 0.5-1.0×10$^6$ cells/test were collected by centrifugation (1500 rpm×5 minutes) and the supernatant was aspirated. The cells (single cell suspension) were washed with 4 mL ice cold FACS Buffer (PBS, 0.5-1% BSA, 0.1% NaN3 sodium azide). The cells were re-suspended in 100 µL ice cold FACS Buffer, add 5 uL antibody was added to each tube and incubated for 30 minutes on ice. The cells were washed 3 times by centrifugation at 1500 rpm for 5 minutes. The cells were then re-suspended in 500 µL ice cold FACS Buffer and temporarily kept in the dark on ice.

The cells were subsequently analyzed on the flow cytometer (BD FACS Canto II) and the generated data were processed using FlowJo 7.6.2 software.

Figure 10:
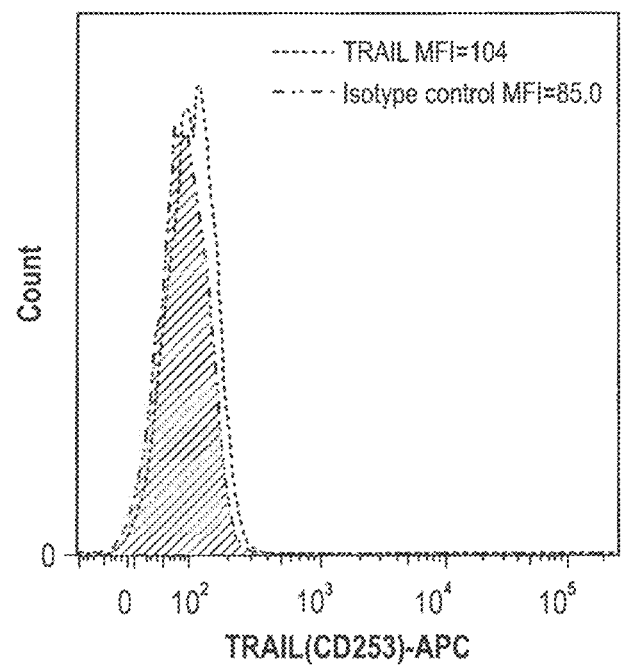
FIG. 10 shows a FACS plot of the baseline expression of TRAIL on KHYG-1 cells.

As can be seen in FIG. 10, FACS analysis showed weak baseline expression of TRAIL on the KHYG-1 cell surface.

TRAIL/TRAIL Variant Knock-in by Electroporation

Wildtype TRAIL mRNA and TRAIL variant (D269H/195R) mRNA was synthesized by TriLink BioTechnologies, aliquoted and stored as −80° C. Mouse anti-human CD253-APC (Biolegend catalog number: 308210) and isotype control (Biolegend catalog number: 400122), and Mouse anti-human CD107a-PE (eBioscience catalog number: 12-1079-42) and isotype control (eBioscience catalog number: 12-4714) antibodies were used to stain cell samples and were analyzed on a BD FACS Canto II flow cytometer. DNA dye SYTOX-Green (Life Technologies catalog number: S7020; 5 mM Solution in DMSO) was used. To achieve transfection efficiencies of up to 90% with high cell viability in KHYG-1 cells with the Nucleofector™ Device (Nucleofector II, Lonza), a Nucleofector™ Kit T from Lonza was used. Antibiotics-free RPMI 1640 containing 10% FBS, L-glutamine (2 mM) and IL-2 (10 ng/mL) was used for post-Nucleofection culture.

KHYG-1 and NK-92 cells were passaged one or two days before Nucleofection, as the cells must be in the logarithmic growth phase. The Nucleofector solution was pre-warmed to room temperature (100 µl per sample), along with an aliquot of culture medium containing serum and supplements at 37° C. in a 50 mL tube. 6-well plates were prepared by filling with 1.5 mL culture medium containing serum and supplements and pre-incubated in a humidified 37° C./5% CO$_2$ incubator. An aliquot of cell culture was prepared and the cells counted to determine the cell density. The required number of cells was centrifuged at 1500 rpm for 5 min, before discarding the supernatant completely. The cell pellet was re-suspended in room temperature Nucleofector Solution to a final concentration of 2×10$^6$ cells/100 µl (maximum time in suspension=20 minutes). 100 µl cell suspension was mixed with 10 µg mRNA (volume of RNA<10 µL). The sample was transferred into an Amaxa-certified cuvette (making sure the sample covered the bottom of the cuvette and avoiding air bubbles). The appropriate Nucleofector program was selected (i.e. U-001 for KHYG-1 cells). The cuvettes were then inserted into the cuvette holder. 500 µl pre-warmed culture medium was added to the cuvette and the sample transferred into a prepared 6-well plate immediately after the program had finished, in order to avoid damage to the cells. The cells were incubated in a humidified 37° C./5% CO$_2$ incubator. Flow cytometric analysis and cytotoxicity assays were performed 12-16 hours after electroporation. Flow cytometry staining was carried out as above.

Figure 11:
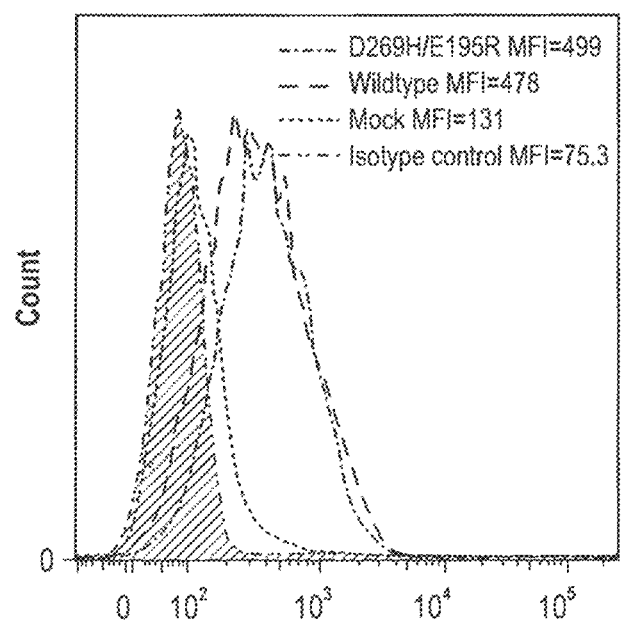
FIG. 11 shows a FACS plot of the expression of TRAIL and TRAIL variant after transfection of KHYG-1 cells.
Figure 12:
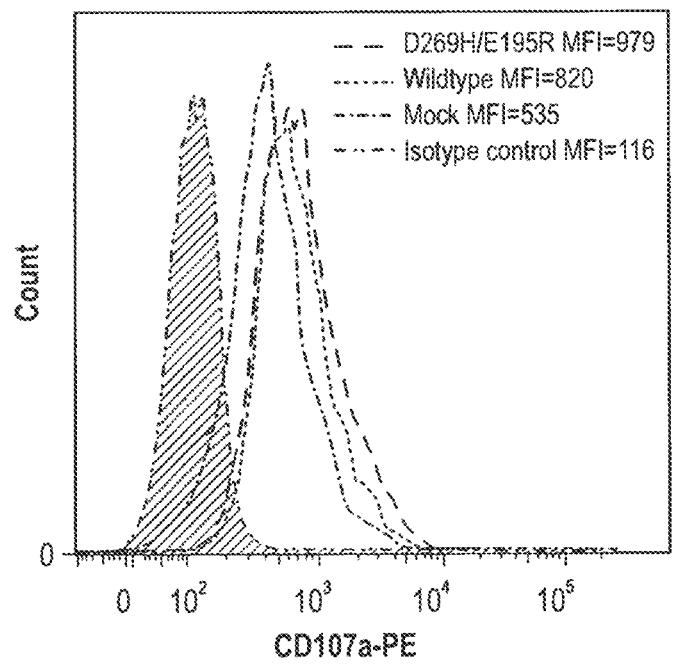
FIG. 12 shows a FACS plot of the expression of CD107a after transfection of KHYG-1 cells.

As can be seen in FIGS. 11 and 12, expression of TRAIL/TRAIL variant and CD107a (NK activation marker) increased post-transfection, confirming the successful knock-in of the TRAIL genes into KHYG-1 cells.

Figure 13:
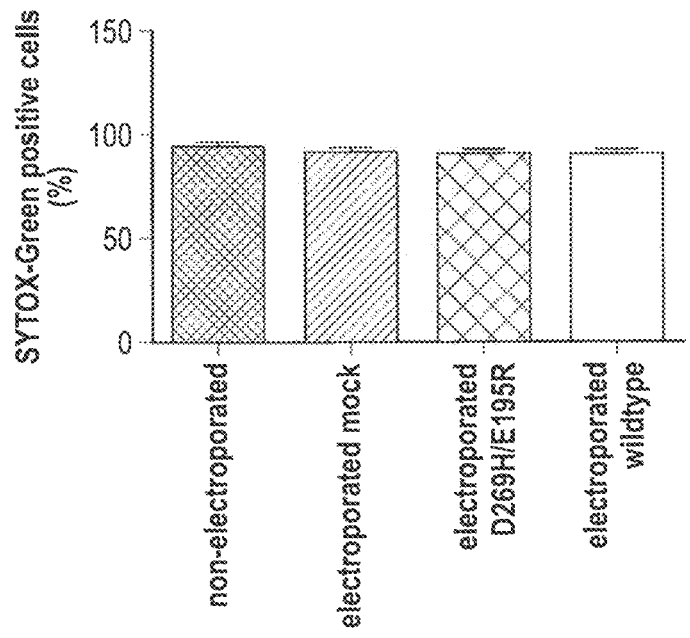
FIG. 13 shows the effects of transfecting KHYG-1 cells with TRAIL and TRAIL variant on cell viability.
Figure 14:
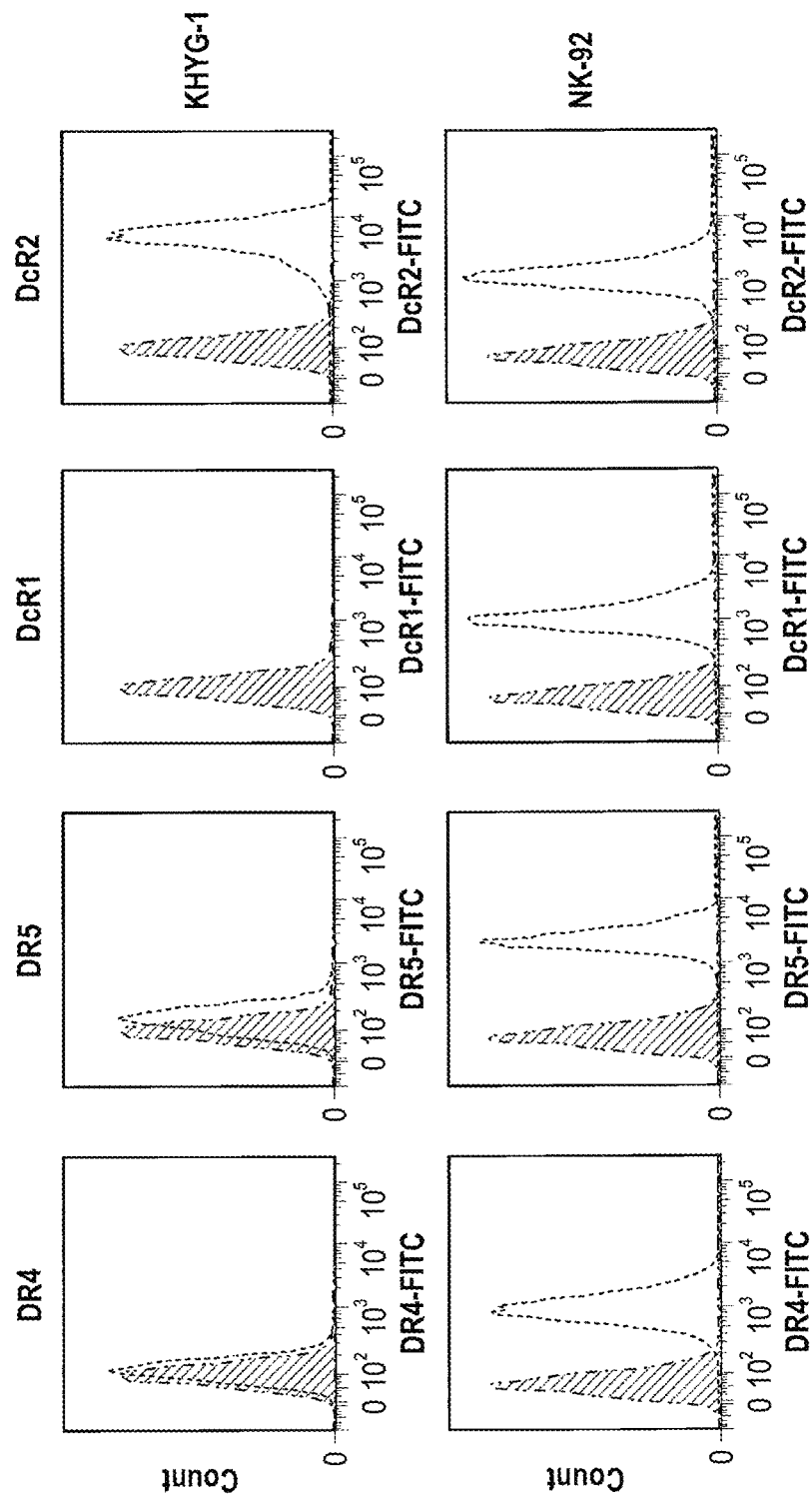
FIG. 14 shows a FACS plot of the baseline expression of DR4, DR5, DcR1 and DcR2 on both KHYG-1 cells and NK-92 cells.

FIG. 13 provides evidence of KHYG-1 cell viability before and after transfection via electroporation. It can be seen that no statistically significant differences in cell viability are observed following transfection of the cells with TRAIL/TRAIL variant, confirming that the expression of wildtype or variant TRAIL is not toxic to the cells. This observation contradicts corresponding findings in NK-92 cells, which suggest the TRAIL variant gene knock-in is toxic to the cells (data not shown). Nevertheless, this is likely explained by the relatively high expression levels of TRAIL receptors DR4 and DR5 on the NK-92 cell surface (see FIG. 14).

Effects of TRAIL/TRAIL Variant on KHYG-1 Cell Cytotoxicity

Mouse anti-human CD2-APC antibody (BD Pharmingen catalog number: 560642) was used. Annexin V-FITC antibody (ImmunoTools catalog number: 31490013) was used. DNA dye SYTOX-Green (Life Technologies catalog number: S7020) was used. A 24-well cell culture plate (SARSTEDT AG catalog number: 83.3922) was used. Myelogenous leukemia cell line K562, multiple myeloma cell line RPM18226 and MM1.S were used as target cells. K562, RPM18226, MM1.S were cultured in RPMI 1640 medium containing 10% FBS, 2 mM L-glutamine and penicillin (100 U/mL)/streptomycin (100 mg/mL).

As explained above, KHYG-1 cells were transfected with TRAIL/TRAIL variant.

The target cells were washed and pelleted via centrifugation at 1500 rpm for 5 minutes. Transfected KHYG-1 cells were diluted to 0.5×10$^6$/mL. The target cell density was then adjusted in pre-warmed RPMI 1640 medium, in order to produce effector:target (E:T) ratios of 1:1.

0.5 mL KHYG-1 cells and 0.5 mL target cells were then mixed in a 24-well culture plate and placed in a humidified 37° C./5% CO$_2$ incubator for 12 hours. Flow cytometric analysis was then used to assay KHYG-1 cell cytotoxicity; co-cultured cells (at different time points) were washed and then stained with CD2-APC antibody (5 µL/test), Annexin V-FITC (5 µL/test) and SYTOX-Green (5 µL/test) using Annexin V binding buffer.

Data were further analyzed using FlowJo 7.6.2 software. CD2-positive and CD2-negative gates were set, which represent KHYG-1 cell and target cell populations, respectively. The Annexin V-FITC and SYTOX-Green positive cells in the CD2-negative population were then analyzed for TRAIL-induced apoptosis.

Figure 15:
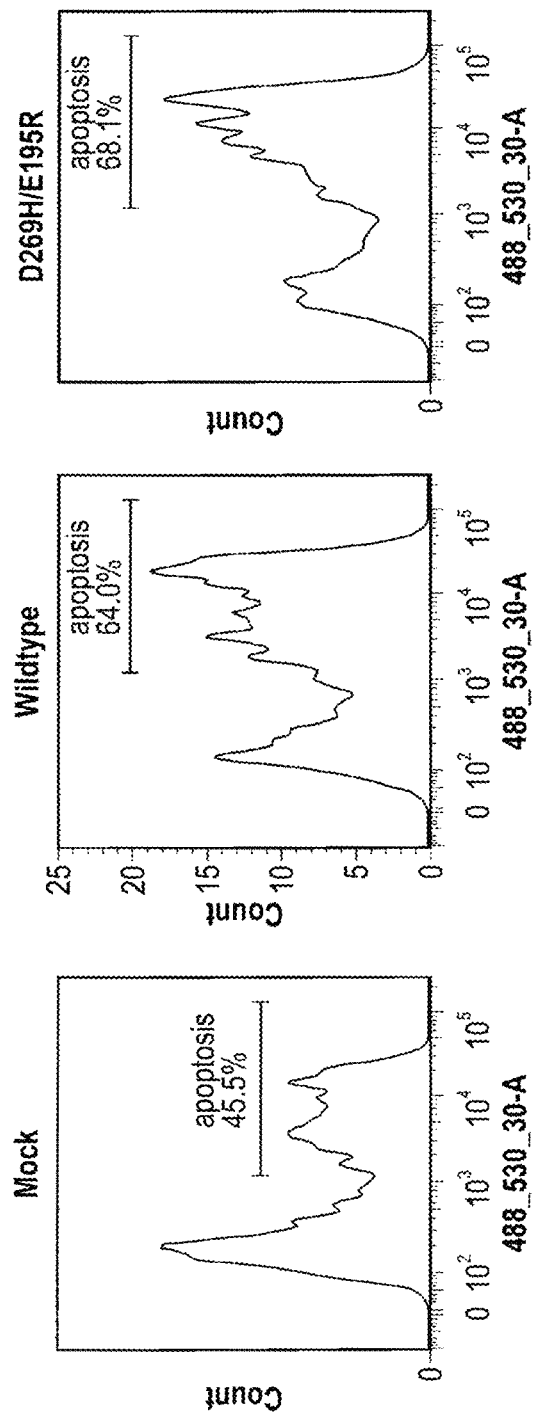
FIGS. 15, 16 and 17 show the effects of expressing TRAIL or TRAIL variant in KHYG-1 cells on apoptosis of three target cell populations: K562, RPMI8226 and MM1.S, respectively.
Figure 16:
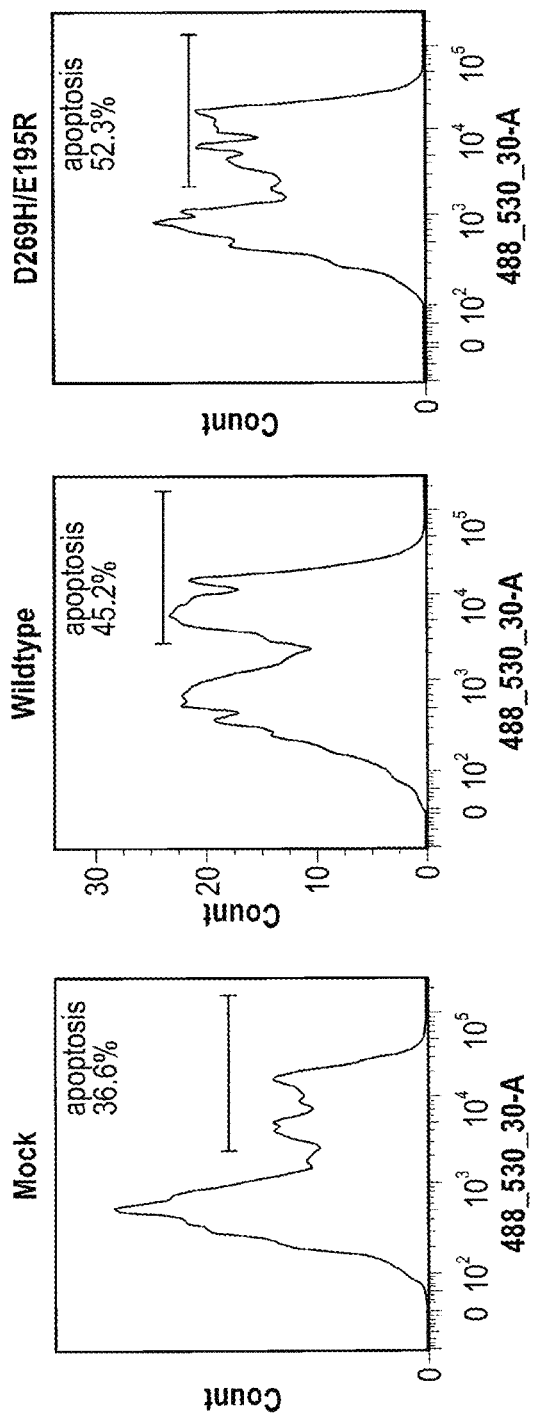
Figure 17:
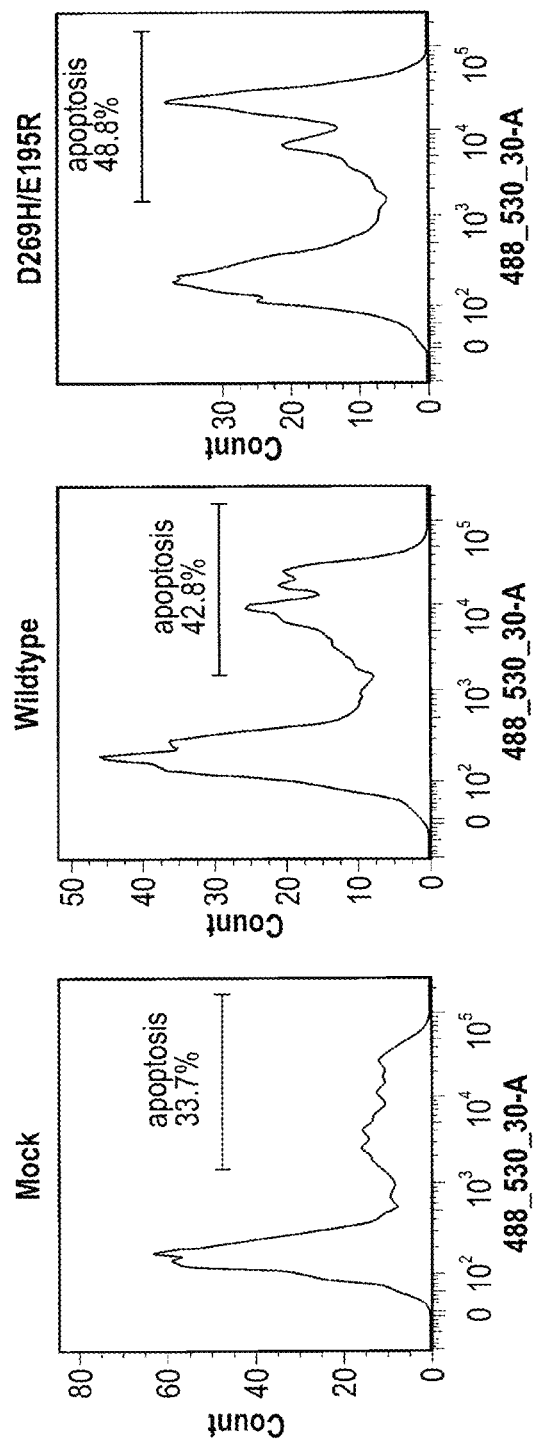

FIGS. 15, 16 and 17 show the effects of both KHYG-1 cells expressing TRAIL or TRAIL variant on apoptosis for the three target cell lines: K562, RPM18226 and MM1.S, respectively. It is apparent for all target cell populations that TRAIL expression on KHYG-1 cells increased the level of apoptosis, when compared to normal KHYG-1 cells (not transfected with TRAIL). Moreover, TRAIL variant expression on KHYG-1 cells further increased apoptosis in all target cell lines, when compared to KHYG-1 cells transfected with wildtype TRAIL.

Cells of the invention, expressing the TRAIL variant, offer a significant advantage in cancer therapy, due to exhibiting higher affinities for the death receptor DR5. When challenged by these cells of the invention, cancer cells are prevented from developing defensive strategies to circumvent death via a certain pathway. Thus cancers cannot effectively circumvent TRAIL-induced cell death by upregulating TRAIL decoy receptors, as cells of the invention are modified so that they remain cytotoxic in those circumstances.

Example 7—Protocol for Blood Cancer Therapy Using NK Cells with TRAIL Variants Knocked-in KHYG-1 cells were transfected with TRAIL variant, as described above in Example 6. The following protocol was developed for use in treating patients with blood cancer:

Following diagnosis of a patient with a cancer suitably treated with the invention, a DR5-inducing agent, e.g. Bortezomib, is administered, prior to administration of the modified NK cells, and hence is used at low doses to upregulate expression of DR5 on the cancer, making modified NK cell therapy more effective.

An aliquot of modified NK cells is then thawed, cultured and administered to the patient.

Since the TRAIL variant expressed by the NK cells used in therapy has a lower affinity for decoy receptors than wildtype TRAIL, there is increased binding of death receptors on the cancer cell surface, and hence more cancer cell apoptosis as a result.

Another option, prior to implementation of the above protocol, is to biopsy the cancer and culture cancer cells ex vivo. This step can be used to identify those cancers expressing particularly high levels of decoy receptors, and/or low levels of death receptors, in order to help determine whether a DR5-inducing agent is appropriate for a given patient. This step may also be carried out during therapy with the above protocol, as a given cancer might be capable of adapting to e.g. reduce its expression of DR5, and hence it may become suitable to treat with a DR5-inducing agent part-way through therapy.

Example 8—Low Dose Bortezomib Sensitizes Cancer Cells to NK Cells Expressing TRAIL Variant Bortezomib (Bt) is a proteasome inhibitor (chemotherapy-like drug) useful in the treatment of Multiple Myeloma (MM). Bortezomib is known to upregulate DR5 expression on several different types of cancer cells, including MM cells.

KHYG-1 cells were transfected with TRAIL variant, as described above in Example 6, before being used to target MM cells with or without exposure to Bortezomib.

Bortezomib-Induced DR5 Expression

Bortezomib was bought from Millennium Pharmaceuticals. Mouse anti-human DR5-AF647 (catalog number: 565498) was bought from BD Pharmingen. The stained cell samples were analyzed on BD FACS Canto II.

(1) MM cell lines RPM18226 and MM1.S were grown in RPM11640 medium (Sigma, St Louis, Mo., USA) supplemented with 2 mM L-glutamine, 10 mM HEPES, 24 mM sodium bicarbonate, 0.01% of antibiotics and 10% fetal bovine serum (Sigma, St Louis, Mo., USA), in 5% $CO_2$ atmosphere at 37° C.

(2) MM cells were seeded in 6-well plates at $1\times10^6$/mL, 2 mL/well.

(3) MM cells were then treated with different doses of Bortezomib for 24 hours.

Figure 18:
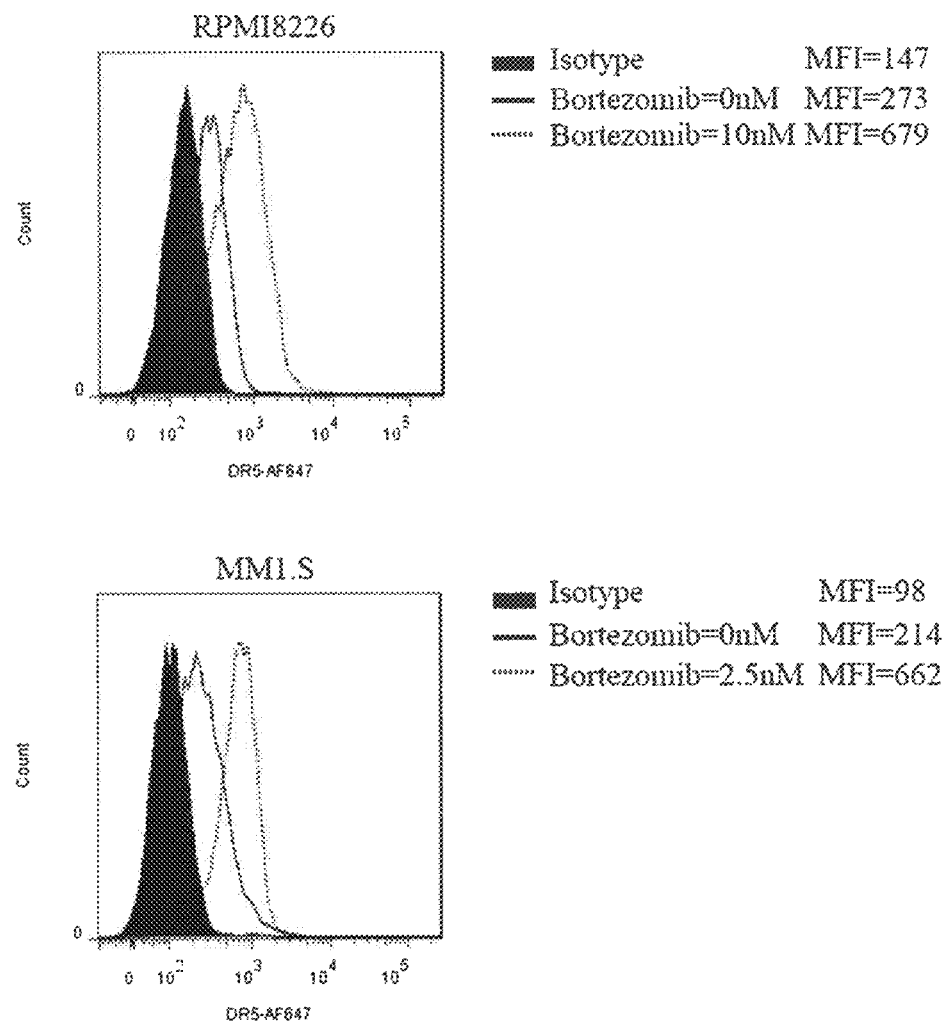
FIG. 18 shows two FACS plots of DR5 expression on RPM18226 cells and MM1.S cells, respectively, wherein the effects of Bortezomib treatment on DR5 expression are shown.

(4) DR5 expression in Bortezomib treated/untreated MM cells was then analyzed by flow cytometry (FIG. 18).

Low dose Bortezomib treatment was found to increase DR5 expression in both MM cell lines (FIG. 18). DR5 upregulation was associated with a minor induction of apoptosis (data not shown). It was found, however, that DR5 expression could not be upregulated by high doses of Bortezomib, due to high toxicity resulting in most of the MM cells dying.

Bortezomib-Induced Sensitization of Cancer Cells

KHYG-1 cells were transfected with the TRAIL variant (TRAIL D269H/E195R), as described above in Example 6.

(1) Bortezomib treated/untreated MM1.S cells were used as target cells. MM1.S cells were treated with 2.5 nM of Bortzeomib or vehicle (control) for 24 hours.

(2) 6 hours after electroporation of TRAIL variant mRNA, KHYG-1 cells were then cultured with MM cells in 12-well plate. After washing, cell concentrations were adjusted to $1\times10^6$/mL, before mixing KHYG-1 and MM1.S cells at 1:1 ratio to culture for 12 hours.

(3) Flow cytometric analysis of the cytotoxicity of KHYG-1 cells was carried out. The co-cultured cells were collected, washed and then stained with CD2-APC antibody (5 uL/test), AnnexinV-FITC (5 uL/test) and SYTOX-Green (5 uL/test) using AnnexinV binding buffer.

(4) Data were further analyzed using FlowJo 7.6.2 software. CD2-negative population represents MM1.S cells. KHYG-1 cells are strongly positive for CD2. Finally, the AnnexinV-FITC and SYTOX-Green positive cells in the CD2-negative population were analyzed.

Figure 19:
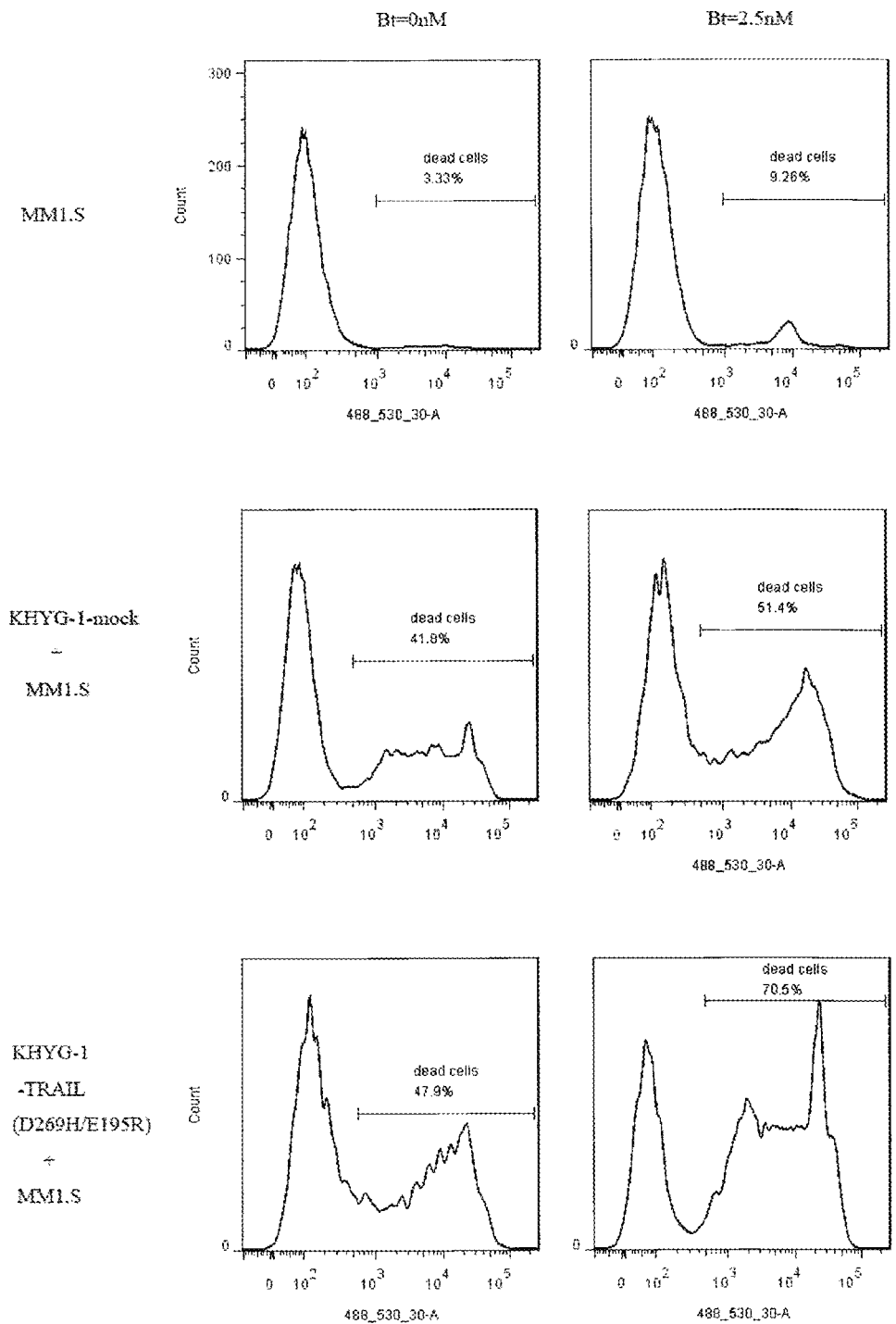
FIG. 19 shows FACS plots of apoptosis in Bortezomib-pretreated/untreated MM1.S cells co-cultured with KHYG-1 cells with/without the TRAIL variant.

Flow cytometric analysis of apoptosis was performed in Bortezomib-pretreated/untreated MM1.S cells co-cultured with KHYG-1 cells electroporated with/without TRAIL variant (FIG. 19).

It was found that Bortezomib induced sensitivity of MM cells to KHYG-1 cells expressing the TRAIL variant. The data therefore indicated that an agent that induced DR5 expression was effective in the model in increasing cytotoxicity against cancer cells, and hence may be useful in enhancing the cancer therapy of the present invention.

Example 9—Confirmation of Induced Apoptosis by the TRAIL Variant

Despite the conclusive evidence of increased NK cell cytotoxicity resulting from TRAIL variant expression in the previous Examples, we wished to confirm whether the increased cytotoxicity resulted from inducing cancer cell apoptosis (most likely) or by inadvertently activating the NK cells to exhibit a more cytotoxic phenotype and hence kill cancer cells via perforin secretion.

Concanamycin A (CMA) has been demonstrated to inhibit perforin-mediated cytotoxic activity of NK cells, mostly due to accelerated degradation of perforin by an increase in the pH of lytic granules. We investigated whether the cytotoxicity of KHYG-1 cells expressing the TRAIL variant could be highlighted when perforin-mediated cytotoxicity was partially abolished with CMA.

CMA-Induced Reduction of Perforin Expression

Mouse anti-human perforin-AF647 (catalog number: 563576) was bought from BD pharmingen. Concanamycin A (catalog number: SC-202111) was bought from Santa Cruz Biotechnology. The stained cell samples were analyzed using a BD FACS Canto II.

(1) KHYG-1 cells were cultured in RPM11640 medium containing 10% FBS (fetal bovine serum), 2 mM L-glutamine, penicillin (100 U/mL)/streptomycin (100 mg/mL), and IL-2 (10 ng/mL).

(2) KHYG-1 cells (6 hours after electroporation, cultured in penicillin/streptomycin free RPMI1640 medium) were further treated with 100 nM CMA or equal volume of vehicle (DMSO) for 2 hours.

(3) The cells were collected ($1 \times 10^6$ cells/test) by centrifugation (1500 rpm×5 minutes) and the supernatant was aspirated.

(4) The cells were fixed in 4% paraformaldehyde in PBS solution at room temperature for 15 minutes.

(5) The cells were washed with 4 mL of FACS Buffer (PBS, 0.5-1% BSA, 0.1% sodium azide) twice.

(6) The cells were permeabilized with 1 mL of PBS/0.1% saponin buffer for 30 minutes at room temperature.

(7) The cells were washed with 4 mL of PBS/0.1% saponin buffer.

(8) The cells were re-suspended in 100 uL of PBS/0.1% saponin buffer, before adding 5 uL of the antibody to each tube and incubating for 30 minutes on ice.

(9) The cells were washed with PBS/0.1% saponin buffer 3 times by centrifugation at 1500 rpm for 5 minutes.

(10) The cells were re-suspended in 500 uL of ice cold FACS Buffer and kept in the dark on ice or at 4° C. in a fridge briefly until analysis.

(11) The cells were analyzed on the flow cytometer (BD FACS Canto II). The data were processed using FlowJo 7.6.2 software.

Figure 20:
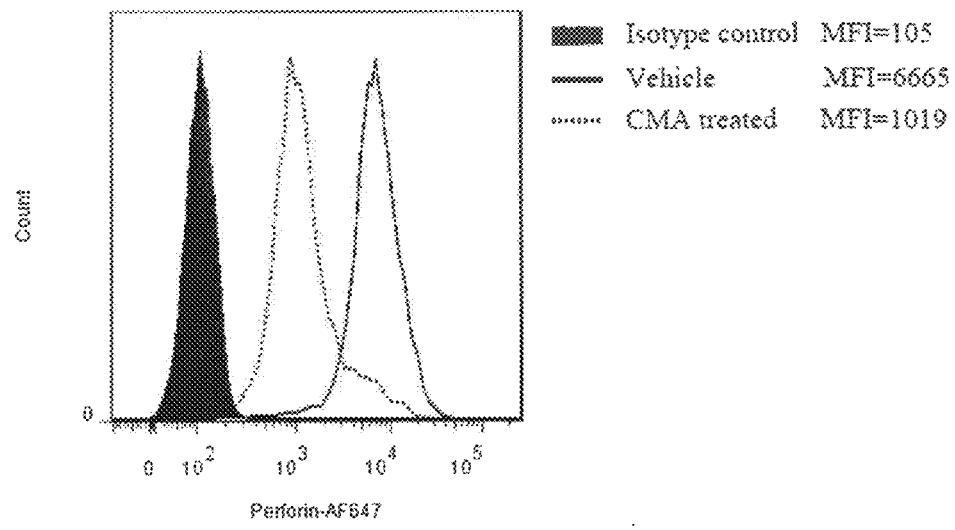
FIG. 20 shows a FACS plot of perforin expression levels in KHYG-1 cells treated with 100 nM CMA for 2 hours.
Figure 21:
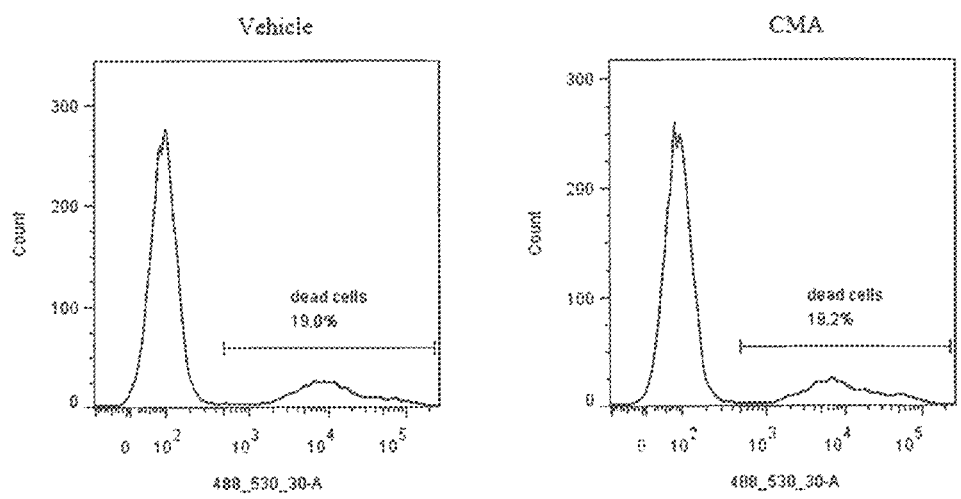
FIG. 21 shows FACS plots of KHYG-1 cell viability after treatment with 100 nM CMA or vehicle.

CMA treatment significantly decreased the perforin expression level in KHYG-1 cells (FIG. 20) and had no negative effects on the viability of KHYG-1 cells (FIG. 21).

Cytotoxicity of NK Cell TRAIL Variants in the Presence of CMA

KHYG-1 cells were transfected with the TRAIL variant (TRAIL D269H/E195R), as described above in Example 6.

(1) MM1.S cells were used as target cells.

(2) 6 hours after electroporation of TRAIL mRNA, KHYG-1 cells were treated with 100 mM CMA or an equal volume of vehicle for 2 hours.

(3) The KHYG-1 cells were washed with RPM11640 medium by centrifugation, and re-suspended in RPM11640 medium containing IL-2, adjusting cell concentrations to $1 \times 10^6$/mL.

(4) The MM1.S cells were re-suspended in RPM11640 medium containing IL-2 adjusting cell concentrations to $1 \times 10^6$/mL.

(5) The KHYG-1 and MM1.S cells were mixed at 1:1 ratio and co-cultured for 12 hours.

(6) Flow cytometric analysis of the cytotoxicity of KHYG-1 cells was carried out. The co-cultured cells were washed and stained with CD2-APC antibody (5 uL/test).

(7) After washing, further staining was performed with AnnexinV-FITC (5 uL/test) and SYTOX-Green (5 uL/test) using AnnexinV binding buffer.

(8) Data were further analyzed using FlowJo 7.6.2 software. CD2-negative population represents MM1.S cells. KHYG-1 cells are strongly positive for CD2. The AnnexinV-FITC and SYTOX-Green positive cells in CD2-negative population were then analyzed.

Figure 22:
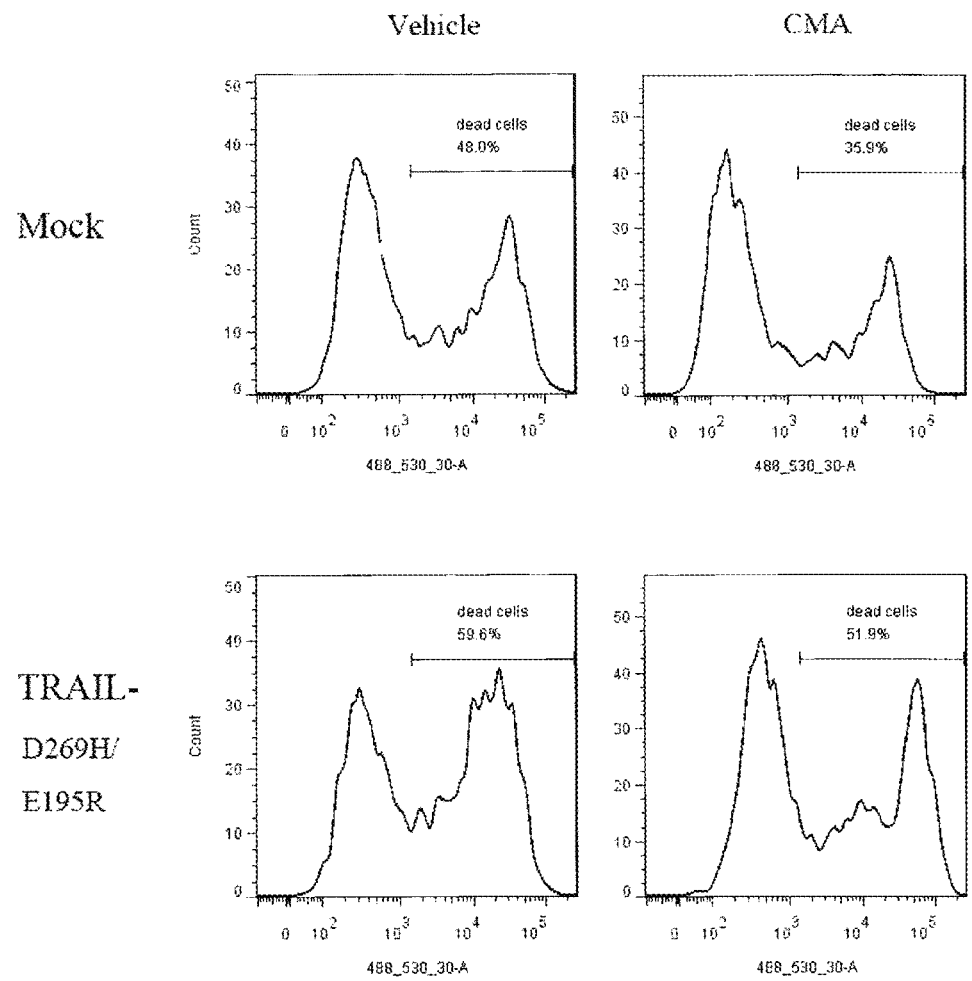
FIG. 22 shows FACS plots of apoptosis in MM1.S cells co-cultured with KHYG-1 cells with/without the TRAIL variant and pretreated with/without CMA.

It was again shown that NK cells expressing the TRAIL variant show higher cytotoxicity than control cells lacking expression of the TRAIL variant (FIG. 22). In this Example, however, it was further shown that CMA was unable to significantly diminish the cytotoxic activity of NK cells expressing TRAIL variant, in contrast to the finding for control NK cells treated with CMA.

NK cells without the TRAIL variant (control or mock NK cells) were shown to induce 48% cancer cell death in the absence CMA and 35.9% cancer cell death in the presence of CMA (FIG. 22). NK cells expressing the TRAIL variant were able to induce more cancer cell death than control NK cells both in the presence and absence of CMA. In fact, even with CMA present, NK cells expressing TRAIL variant induced more cancer cell death than control NK cells in the absence of CMA.

This data thus shows the importance of the TRAIL variant in increasing NK cell cytotoxicity against cancer cells via a mechanism less susceptible to perforin-related downregulation. Since perforin is used commonly by NK cells to kill target cells, and many cancer cells have developed mechanisms for reducing NK cell perforin expression, in order to evade cytotoxic attack, the NK cells of the invention represent a powerful alternative less susceptible to attenuation by cancer cells.

Example 10—Combined Expression of Mutant TRAIL Variant and Knockdown of Checkpoint Inhibitory Receptor CD96 in KHYG-1 Cells Increases in NK cell cytotoxicity were observed when knocking down checkpoint inhibitory receptor CD96 expression and also when expressing TRAIL variant. We also tested combining the two genetic modifications to provoke a synergistic effect on NK cell cytotoxicity.

CD96 expression was knocked down in KHYG-1 cells, as described in Example 2.

KHYG-1 cells were transfected with the TRAIL variant (TRAIL D269H/E195R), as described above in Example 6.

(1) 12 hours after electroporation KHYG-1 cells were co-cultured with target cells (K562 or MM1.S) at a concentration of $1 \times 10^6$/mL in 12-well plates (2 mL/well) for 12 hours. The E:T ratio was 1:1.

(2) 12 hours after co-culture, the cells were collected, washed, stained with CD2-APC, washed again and further stained with AnnexinV-FITC (5 uL/test) and SYTOX-Green (5 uL/test) using AnnexinV binding buffer.

(3) Cell samples were analyzed using a BD FACS canto II flow cytometer. Data were further analyzed using FlowJo 7.6.2 software. CD2-negative population represents MM1.S cells. KHYG-1 cells are strongly positive for CD2. The AnnexinV-FITC and SYTOX-Green positive cells in the CD2-negative population were then analyzed.

Figure 23:
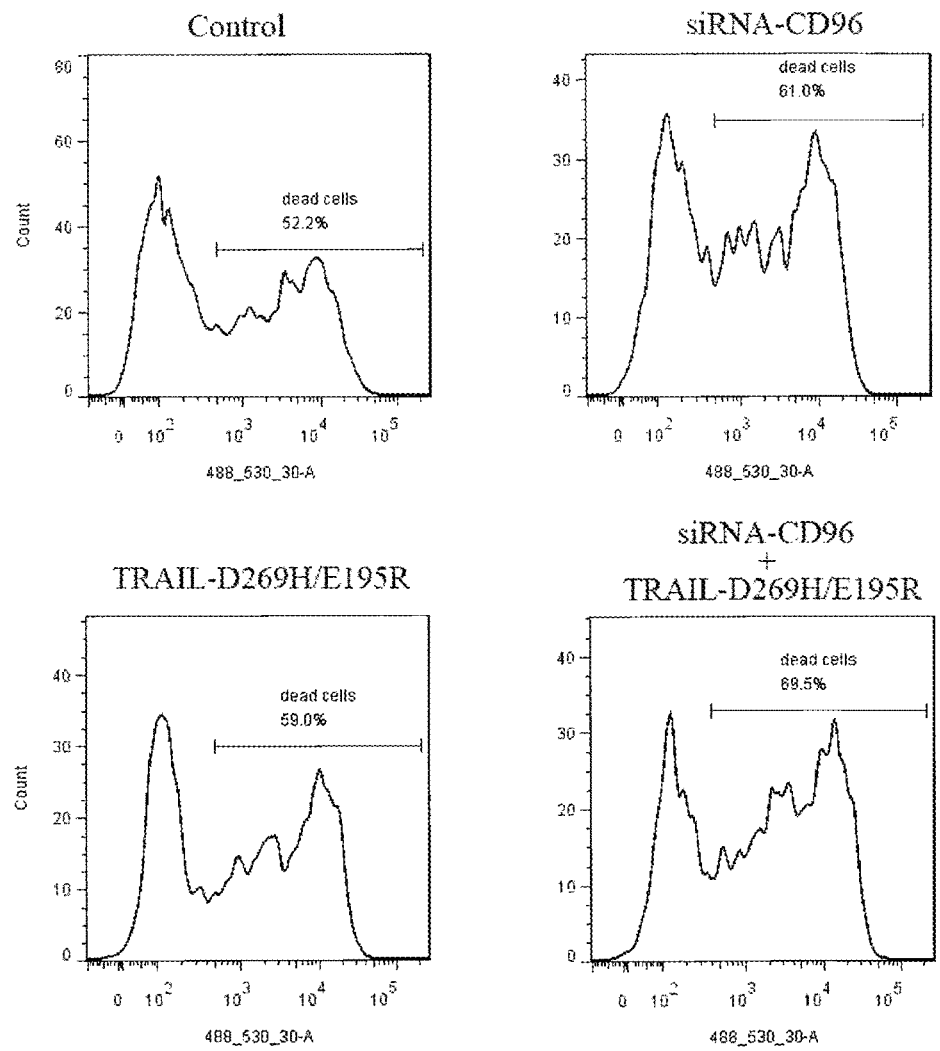
FIG. 23 shows FACS plots of apoptosis in K562 cells co-cultured with KHYG-1 cells with CD96-siRNA and/or TRAIL variant expression.
Figure 24:
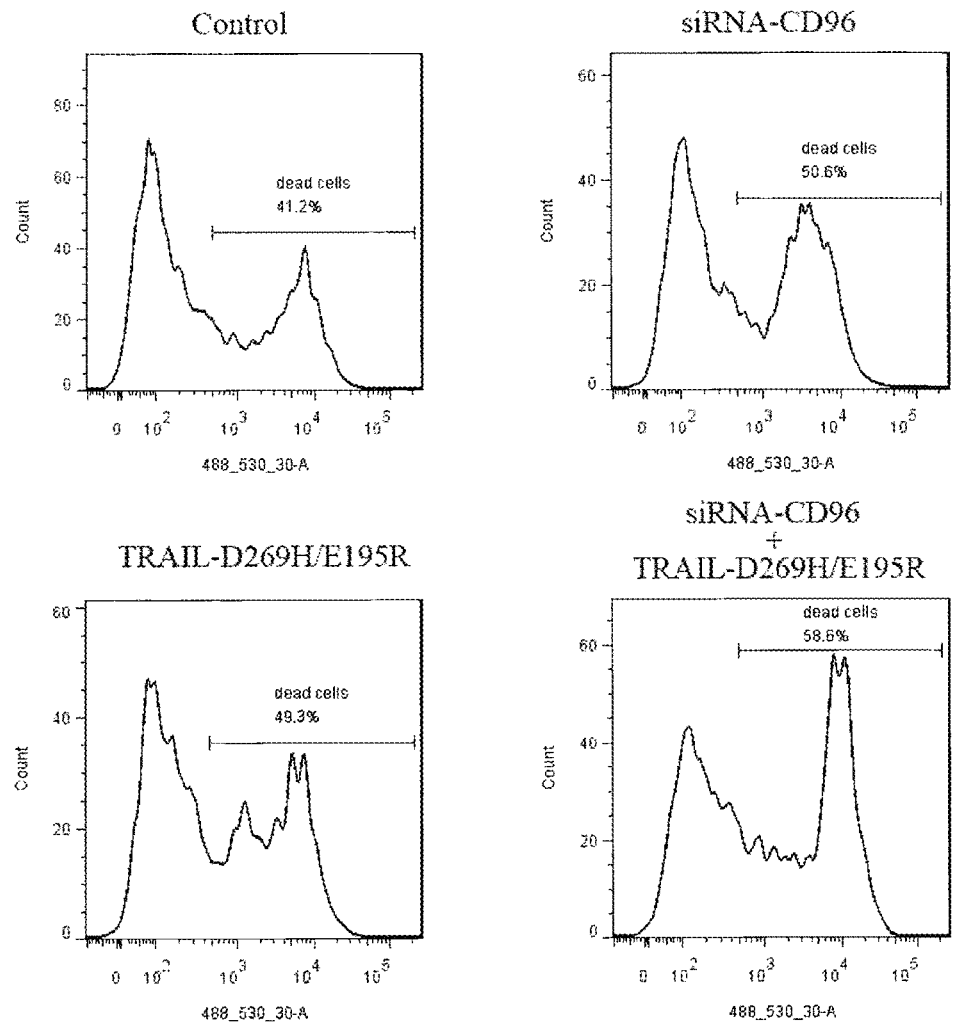
FIG. 24 shows FACS plots of apoptosis in MM1.S cells co-cultured with KHYG-1 cells with CD96-siRNA and/or TRAIL variant expression.

Simultaneously knocking down CD96 expression and expressing TRAIL variant in KHYG-1 cells was found to synergistically enhance the cells' cytotoxicity against both K562 target cells (FIG. 23) and MM1.S target cells (FIG. 24). This was indicated by the fact that in both target cell groups, more cell death resulted from the simultaneous genetic modification than resulted from the individual modifications in isolation.

At the same time, further evidence showing knockdown of CD96 increases NK cell cytotoxicity was obtained (FIGS. 23 & 24), in addition to further evidence showing expression of the TRAIL mutant/variant increases NK cell cytotoxicity (FIGS. 23 & 24).

Example 11—Further TRAIL Variants for NK Cell Therapies

Further to TRAIL mutants exemplified in above-mentioned Examples, there are a number of other known TRAIL mutations that give rise to an increased affinity for TRAIL death receptors and/or a decreased affinity for decoy receptors. Thus, in further embodiments of the invention all of these mutations are used to produce NK cells expressing TRAIL variants according to the invention.

Specifically, in embodiments of the invention NK cells are modified to express the TRAIL variants listed below, for example by the method described above in Example 6.

In addition to D269H/E195R, further TRAIL variants with increased affinity for DR5 are known from Van der sloot et al. "Designed tumor necrosis factor-related apoptosis-inducing ligand variants initiating apoptosis exclusively via the DR5 receptor" Proc Natl Acad Sci USA. 2006 Jun. 6; 103(23):8634-9. These include D269H, E195R, T214R, T214R/E195R and T214R/D269H.

Further TRAIL variants with increased affinity for DR5 (DR5 variants) are known from MacFarlane et al. CANCER RES., vol. 65, 2005, pages 11265-11270. These include N199V, Y189A/Q193S/N199V/K201R/Y213W/S215D and Y213W/S215D.

D269A and Y240A are further DR5 variants known from WO 01/00832.

Additionally, a number of TRAIL variants with increased affinity for DR4 (DR4 variants) are known from WO 2009/066174. These include G131R, G131K, R149I, R149M, R149N, R149K, S159R, Q193H, W193K, N199R, N199R/K201H, N199H/K201R, G131R/N199R/K201H, G131R/N199R/K201H, G131R/N199R/K201H/R149I/S159R/S215D, G131R/R149I/S159R/S215D, G131R/D218H, K201R, K201H, K204E, K204D, K204L, K204Y, K212R, S215E, S215H, S215K, S215D, D218H, K251D, K251E and K251Q.

Further DR4 variants are known from MacFarlane et al. 2005, e.g. Y189Q/R191K/Q193R/H264R/I266L/D267Q.

Moreover, a number of TRAIL variants with decreased affinity for TRAIL decoy receptors (DcR variants) are known from Leary et al. 2016 "Decoy receptors block TRAIL sensitivity at a supracellular level: the role of stromal cells in controlling tumour TRAIL sensitivity" Oncogene 35:1261-1270. These include T261L, H270D, T200H, T261L/G160E, T261L/H270D, T261L/G160E/H270D and T261L/G160E/H270D/T200H.

Further DcR variants are known from WO 01/00832, e.g. D203A and D218A.

It is important to note that a number of TRAIL mutations not listed above also have increased affinity for DR5 and/or DR4 and/or decreased affinity for TRAIL decoy receptors. Those listed above are provided as examples and are not intended to limit the invention. The disclosure comprises NK cells modified to express any TRAIL variant with increased affinity for DR5 and/or DR4 and/or decreased affinity for TRAIL decoy receptors.

Example 12

Wildtype TRAIL and 4C9 Plasmid Construction

Figure 25:
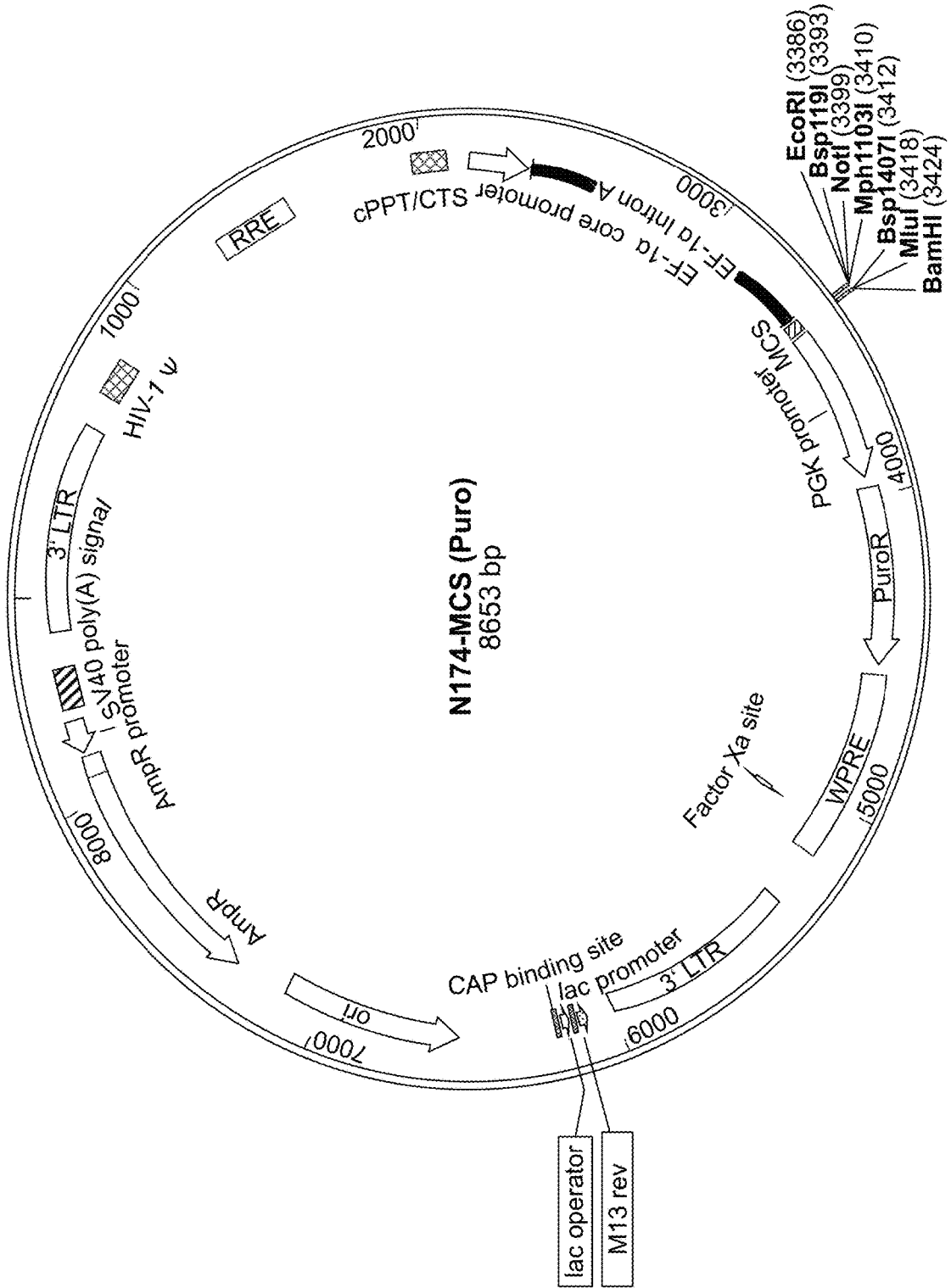
FIG. 25 shows the N174-MCS cloning vector.

DNA nucleotides coding for Wildtype (WT) TRAIL or the DR4 mutant (4C9) TRAIL protein were cloned into N174-MCS (Puro) vectors (Addgene cat: 81068) (see FIG. 25). The sequences were cloned between the NotI and BamHI restriction sites of the vectors. 4C9 is a DR4-specific TRAIL variant comprising amino acid substitutions G131R/R149I/S159R/S215D.

Competent *E. coli* bacteria were heat-shocked with 1 µl of the appropriate diluted plasmid solution (5 ng/µl) and plated onto agar plates containing ampicillin. Overnight, cultured bacterial single colonies were isolated and grown in LB broth containing ampicillin. Plasmid DNA was isolated by pelleting down the bacterial cultures in resuspension buffer containing RNase A followed by lysis and neutralization to each suspension. Endotoxin-free plasmid DNA was purified in NucleoBondXtra columns as per the manufacturer's protocol and reconstituted in 400 µl of H2O-EF.

Nucleofection of KHYG-1 Cells

KHYG-1 cells in the logarithmic growth phase were passaged at 1:1 (10 ml cell suspension+10 ml culture media) the day before nucleofection in T25 flasks. The Lonza Nucleofection kit T (Cat: VCA-1002) was used: one Nucleofection sample contained 100 µl of nucleofection solution (standard cuvette) and $2 \times 10^6$ cells. The nucleofection solution contained Supplement 18 µl and Nucleofector solution 82 µl (for each sample) prepared fresh and incubated at 37° C. for 10 minutes. The solution-T was warmed to room temperature. A fresh 12 ml aliquot of culture medium (CM) was prepared containing 2.4 ml FBS, 9.6 ml RPMI 1640 and supplements 1.2 µl IL-2 (RPM11640+20% FBS+100 IU/ml IL-2) at 37° C. in a 15 ml tube (no antibiotics). 4 ml of CM in T25 flasks, and plates were incubated in a humidified 37° C. incubator for 20 minutes. 10 ml cell culture was transferred into 15 ml tubes and the cells were counted to determine the cell density. $2 \times 10^6$/sample was dispensed into 15 ml tubes. The required number of cells $2 \times 10^6$ were centrifuged at 1200 RPM for 5 min (acc. 9/decc.7). The supernatant was completely discarded so that no residual medium covered the cell pellet. The cell pellet was re-suspended at room temperature in 100 µl Nucleofector Solution (see above) to a final concentration of $2 \times 10^6$ cells/100 µl. The cell suspension was not stored longer than 5 minutes in Nucleofector Solution, as this reduced cell viability and gene transfer efficiency.

1 µg of the respective plasmid DNA was added per tube excluding MOCK. The samples were as follows: Mock, Wild Type (WT) TRAIL, and DR4 (4C9) Mutant TRAIL. The sample was transferred into an Amaxa certified cuvette. The sample covered the bottom of the cuvette, and air bubbles were avoided while pipetting. The cuvette was closed with a blue cap. Nucleofector program (A-024) was selected. The cuvette was inserted into the cuvette holder before pressing the "x" button to start the program. To avoid damage to the cells, the samples were removed from the cuvette immediately after the program had finished (display showing "OK"). Pre-warmed culture medium was added into the cuvette and the sample transferred into one T25 flask. The "X" button was pressed to reset the Nucleofector. Cells were incubated in a humidified 37° C. incubator. Cell suspensions were incubated at 37° C. and 5% CO2. 2 ml fresh media (RPM11640+10% FBS+100 IU/ml IL-2) as per requirement was added. On day 3 post-nucleofection cells from each T25 were collected, and the dead cells were removed using a dead cell removal kit (Miltenyi Biotec, Cat: 130-090-101) as per the manufacturer's guidelines. The viable cell population was subsequently re-plated in T25 flasks and allowed to grow in suspension at 37° C. and 5% $CO_2$ for another 3 days. On day 6 post-nucleofection, cells from each flask were collected and the (TRAIL) CD253 expression was analyzed as described below.

Flow Cytometry Based Expression of TRAIL (CD253) KHYG1 Cells

FACS tubes were pre-filled with 200 µl FACS buffer. Cells were spun down at 2000 RPM for 3 minutes. The supernatant was discarded by inverting and then blotting on clean dry paper. Re-suspend cells in tubes were vortexed. For staining, 3 µl CD253-PE (Biolegend: Cat: 308205; clone—RIK2) was added in tubes for 60 µl cell suspension, before incubating for 25 minutes in a refrigerator. 200 µl FACS buffer was added and before spinning down at 2000 RPM for 3 minutes. The supernatant was discarded and the cells re-suspended in the tubes by vortexing. 200 µl FACS buffer was added to each tube and fluorescence was measured in FACS Canto II. The cells were analyzed in the flow cytometry using a 488 nm laser and detection filter of 585/42 on a FACS Canto II (see FIG. 26).

TRAIL (CD253) Expression in KHYG-1 Cells

Figure 26:
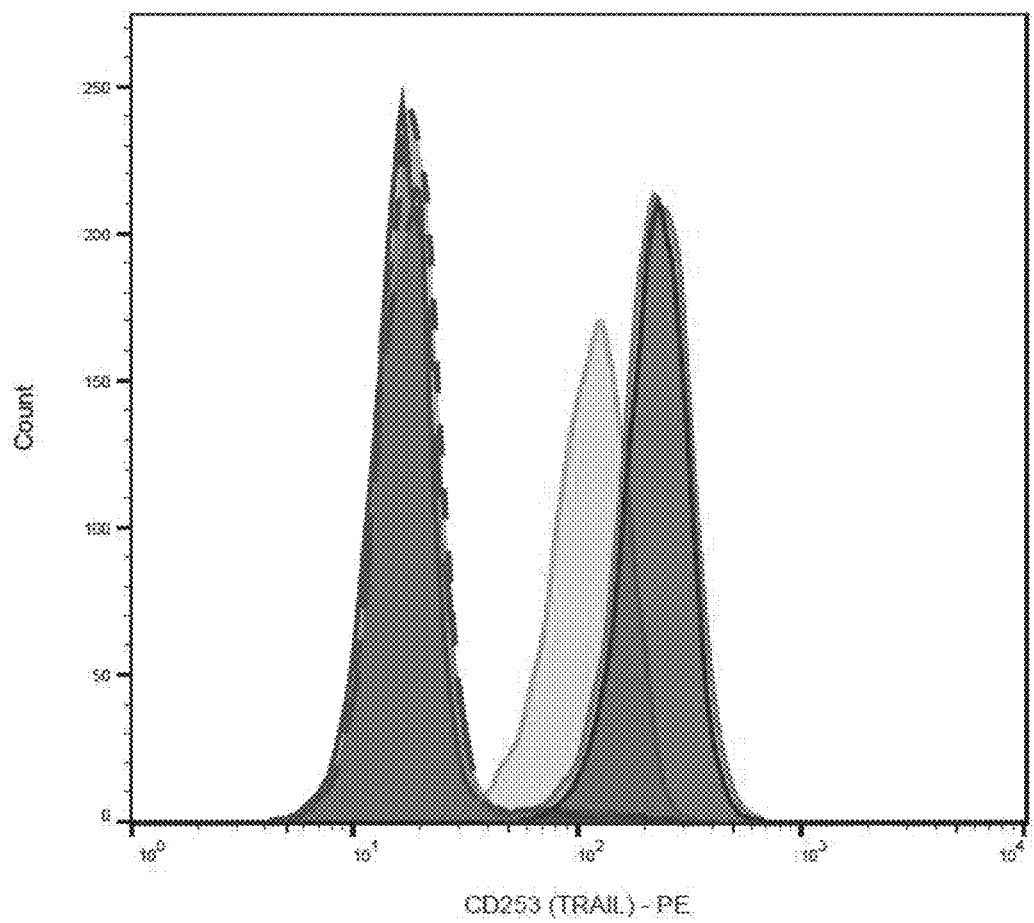
FIG. 26 shows a FACS plot of KHYG-1 TRAIL expression before and after transfection with wildtype TRAIL or 4C9 mutant TRAIL.

Nucleofection of KHYG-1 NK cells with wildtype TRAIL and the DR4 (4C9) mutant TRAIL cloned into an expression plasmid resulted in an increase in expression of TRAIL protein on the surface of KHYG-1 cells as seen in FIG. 26. The mean fluorescent intensity (MFI) as determined by analysis using FlowJo v10 software showed Mock nucleofected KHYG-1 cells had TRAIL expression of 121 MFI units (light blue histogram). The TRAIL (CD253) surface protein expression of KHYG-1 cells increased to 235 (red histogram), and 236 (dark blue histogram) MFI units upon nucleofection with wildtype TRAIL and DR4 (4C9) mutant TRAIL, respectively, 6-days post nucleofection. This 2-fold increase in protein expression was also clearly evident on overlaying the histograms of different samples (as seen in FIG. 26), by the distinct shift of the light green (WT TRAIL) and dark red-brown histogram (DR4 Mutant TRAIL) over and above the red histogram (Mock nucleofected KHYG1).

FIG. 26 confirmed expression of the DR4 mutant and hence the transfection method was successful, yielding a NK cell expressing the 4C9 mutant.

The invention thus provides NK cells and cell lines, and production thereof, for use in blood cancer therapy.

The invention claimed is:

1. A method of treating a TRAIL-expressing blood cancer in an individual in need thereof, comprising administering to the individual a natural killer (NK) cell or NK cell line modified to express a TRAIL mutant, wherein the TRAIL mutant has an increased affinity for a TRAIL receptor and/or a decreased affinity for a decoy TRAIL receptor, relative to wildtype TRAIL.

2. The method of claim 1, wherein the blood cancer is selected from acute lymphocytic leukemia (ALL), acute myeloid leukemia (AML), chronic lymphocytic leukemia (CLL), chronic myeloid leukemia (CML), Hodgkin's lymphoma, non-Hodgkin's lymphoma, T-cell lymphoma, B-cell lymphoma, asymptomatic myeloma, multiple myeloma, active myeloma, and light chain myeloma.

3. The method of claim 1, further comprising administering to the individual an effective amount of an agent that upregulates expression of DR5 and/or DR4.

4. The method of claim 3, wherein the agent is a proteasome inhibitor.

5. The method of claim 4, wherein the proteasome inhibitor is bortezomib.

6. The method of claim 1, wherein the NK cell or NK cell line further comprises a modification that reduces or abolishes expression of a checkpoint inhibitory receptor.

7. The method of claim 6, wherein the checkpoint inhibitory receptor is selected from CD96 (TACTILE), CD152 (CTLA4), CD223 (LAG-3), CD279 (PD-1), CD328 (SIGLEC7), SIGLEC9, TIGIT, and TIM-3.

8. A method of treating a DR4-expressing blood cancer in an individual in need thereof, comprising administering to the individual a natural killer (NK) cell or NK cell line modified to express a TRAIL mutant, wherein the TRAIL mutant has an increased affinity for a DR4 TRAIL receptor, relative to wildtype TRAIL, and wherein the TRAIL mutant comprises mutations G131R, R149I, S159R and S215D, wherein the blood cancer is a DR4-expressing blood cancer.

9. The method of claim 8, wherein the blood cancer is selected from acute lymphocytic leukemia (ALL), acute myeloid leukemia (AML), chronic lymphocytic leukemia (CLL), chronic myeloid leukemia (CML), Hodgkin's lymphoma, non-Hodgkin's lymphoma, T-cell lymphoma, B-cell lymphoma, asymptomatic myeloma, multiple myeloma, active myeloma, and light chain myeloma.

* * * * *